(12) United States Patent
Yadav et al.

(10) Patent No.: US 11,680,078 B2
(45) Date of Patent: Jun. 20, 2023

(54) ANTICANCER COMPOUNDS

(71) Applicant: GODAVARI BIOREFINERIES LIMITED, Maharashtra (IN)

(72) Inventors: Vitthal Yadav, Maharashtra (IN); Maithili Athavale, Maharashtra (IN); Prashant Kharkar, Maharashtra (IN); Sangeeta Srivastava, Maharashtra (IN); Samir Somaiya, Maharashtra (IN); Smera Satish, Maharashtra (IN); Sandip Gavade, Maharashtra (IN)

(73) Assignee: GODAVARI BIOREFINERIES LTD., Maharashtra (IN)

( * ) Notice: Subject to any disclaimer, the term of this patent is extended or adjusted under 35 U.S.C. 154(b) by 27 days.

(21) Appl. No.: 17/364,570

(22) Filed: Jun. 30, 2021

(65) Prior Publication Data
US 2022/0389046 A1    Dec. 8, 2022

Related U.S. Application Data

(63) Continuation of application No. 16/336,460, filed as application No. PCT/IN2018/050237 on Apr. 19, 2018, now Pat. No. 11,084,843.

(30) Foreign Application Priority Data

Apr. 20, 2017  (IN) .......................... 201621035967
Dec. 14, 2017  (IN) .......................... 201721045003

(51) Int. Cl.
| | | |
|---|---|---|
| *C07H 15/26* | (2006.01) | |
| *A61P 35/00* | (2006.01) | |
| *C07D 311/48* | (2006.01) | |
| *C07D 317/50* | (2006.01) | |
| *C07D 405/04* | (2006.01) | |
| *C07D 405/12* | (2006.01) | |
| *C07D 405/14* | (2006.01) | |
| *C07D 407/04* | (2006.01) | |
| *C07D 407/12* | (2006.01) | |
| *A61K 31/357* | (2006.01) | |
| *A61K 31/4709* | (2006.01) | |
| *C07C 1/00* | (2006.01) | |
| *A61K 31/7048* | (2006.01) | |
| *A61K 31/10* | (2006.01) | |
| *A61K 31/4025* | (2006.01) | |
| *C07D 317/56* | (2006.01) | |

(52) U.S. Cl.
CPC ............. *C07H 15/26* (2013.01); *A61K 31/10* (2013.01); *A61K 31/357* (2013.01); *A61K 31/4025* (2013.01); *A61K 31/4709* (2013.01); *A61K 31/7048* (2013.01); *A61P 35/00* (2018.01); *C07C 1/00* (2013.01); *C07D 311/48* (2013.01); *C07D 317/50* (2013.01); *C07D 317/56* (2013.01); *C07D 405/04* (2013.01); *C07D 405/12* (2013.01); *C07D 405/14* (2013.01); *C07D 407/04* (2013.01); *C07D 407/12* (2013.01)

(58) Field of Classification Search
None
See application file for complete search history.

(56) References Cited

FOREIGN PATENT DOCUMENTS

CN         101463055 A   *   6/2009   ............. C07H 15/24

OTHER PUBLICATIONS

Subbaraju, G. V., Rajasekhar, D., Kavitha, J., & Jimenez, J. I. (2001). Justicia lignans: Part 7—Two new diphyllin glycosides from Justicia neesii Ramamoorthy. (Year: 2001).*
Govindachari, T. R., Sathe, S. S., Viswanathan, N., Pai, B. R., & Srinivasan, M. (1969). Chemical constituents of Cleistanthus collinus (Roxb.). Tetrahedron, 25(14), 2815-2821. (Year: 1969).*
Satyanarayana, P., Ramu, K. S., Ward, R. S., & Pelter, A. (1995). Characterization of a New Series of Diphyllin Esters from Sauropus quadrangularis Muell-Arg. ChemInform, 26(42), no-no. (Year: 1995).*
Zhao Yu, Lu Yapeng, & Zhu Li. (2008). Synthesis of Ether and Arylacylester Derivatives of Diphyllin. Applied Chemistry, 25(11), 1315-1319. (Year: 2008).*

* cited by examiner

*Primary Examiner* — Dale R Miller
(74) *Attorney, Agent, or Firm* — Intellectual Property Law Group LLP

(57) ABSTRACT

The present invention discloses compounds for inhibition of uncontrolled cell proliferation particularly in cancer stem cells. Particularly, the invention relates to compounds of Formula III to XIV for the treatment of cancer, such as breast and prostate cancer.

11 Claims, 19 Drawing Sheets

ANTICANCER COMPOUNDS

CROSS-REFERENCE TO RELATED APPLICATIONS

This application is a continuation of co-pending U.S. patent application Ser. No. 16/336,460 filed on Mar. 25, 2019, which is hereby incorporated herein by reference in its entirety. The application Ser. No. 16/336,460 is a U.S. National Phase application, under 35 U.S.C. § 371, of International Application no. PCT/IN2018/050237, with an international filing date of Apr. 19, 2018 and claims benefit of India Application no. 201621035967 filed on Apr. 20, 2017, and India Application no. 201721045003 filed on Dec. 14, 2017; and each of which is hereby incorporated by reference for all purposes.

FIELD OF THE INVENTION

The present invention relates to compounds for inhibition of uncontrolled cell proliferation, particularly cancer stem cells. The present invention also relates to the compounds for use in the treatment of cancer.

BACKGROUND OF THE INVENTION

Cancer is a condition in which abnormal cells proliferate and spread at any place in the body. In other words, cancer is an uncontrolled growth of abnormal cells. Cancer is a leading cause of death worldwide. It remains the second most dreadful disease in India, killing more than three million patients each year. It is of major concern in India and is reported to be one of the ten leading causes of deaths in India.

While molecularly-targeted therapies are available for treatment of cancer for a high price, majority of the world population rely on standard chemotherapy. The standard anticancer regiment targets most of the dividing cancer cells and not quiescent or slow-dividing cancer stem cells (CSCs). Even though, CSCs have been identified a while ago, scientists around the globe are still looking to find CSC-targeted agents and unfortunately, until today, there is none available in the market to specifically target CSCs.

CSCs and work either alone or in combination with the standard therapies to provide effective treatment option for the cancer patients.

SUMMARY OF INVENTION

The present invention provides compounds for the treatment of cancer, particularly—cancer stem cells that show preferential toxicity towards malignant cells, particularly in cancer cell lines such as breast cancer, and/or prostate cancer cell lines.

In one aspect of the present invention, compound of Formula III is provided:

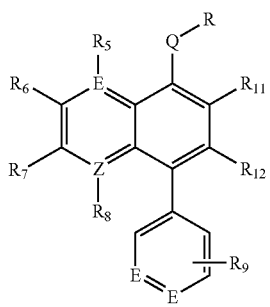

where E and Z is selected from C, O, N, S, salts of N such as N, HCl; Q is O, S, —$CH_2O$—, —NY', wherein Y' is selected from —H, alkyl, $SOOCH_3$; $R^5$ is —H, —Cl, when E and/or Z is —C; $R^6$ and $R^7$ each independently is selected from —H, alkoxy, alkyl, substituted or unsubstituted aromatic group, —$NH_2$, —$NO_2$, $NHCOCH_3$, —CN, —O—, halogen, —$OCF_3$ or $R^6$ and $R^7$ together form a heterocyclic ring; $R^8$ is —H, -Cl, when E and/or Z is —C; $R_9$ is —CH2-O—CH2, —COOH, —X where X can be F, Cl, Br, alkyl such as —$CH_3$, —OH, alkoxy such as —OMe, $NHCOCH_3$, H, $NH_2$; $R^{11}$ and $R^{12}$ each independently is selected from —H, or $R^{11}$ and $R^{12}$ can be substituted or unsubstituted 5- or 6-membered ring, such as lactone, —C(O)O-alkyl such as —$C(O)OC_2H_5$; R is selected from

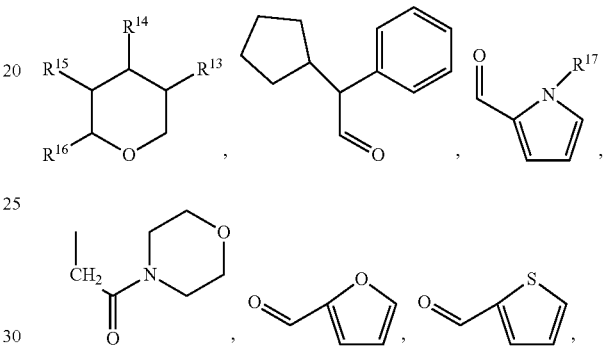

—H, —$C(O)CH_2Cl$, —SOO—$CH_3$, —SOOPh, —$CH_2C(O)N(CH_3)_2$, —C(O)NHPh, —C(O)NHPhOH, —C(S)NHPh, —$CH_2Ph$, —COAr, —SOOAr, —CONHAr, —$CH_2Ar$, —CSNHAr, wherein, $R^{13}$ is selected from —OH, —$NH_2$, —$NHCOCH_3$, X=F, Cl, Br, alkyl, acetyl, $C_3$-$C_8$ acyl group; $R^{14}$ is selected from alkoxy, —OMe, —OH, $NH_2$, —$NHCOCH_3$, X=F, Cl, Br, alkyl, acetyl, $C_3$-$C_8$ acyl group; $R^{15}$ is selected from alkoxy, —OMe, —OH, —H, Br, $NH_2$, X=F, Cl, Br, alkyl, acetyl, $C_3$-$C_8$ acyl group; $R^{16}$ is selected from —H, —$CH_2OH$, —OH, alkyl, alkoxy; $R^{17}$ is selected from alkyl.

In another aspect of the present invention, compound of Formula IV is provided:

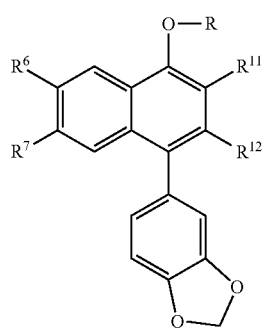

where $R^6$ and $R^7$ each independently is selected from —H, alkoxy, alkyl, substituted or unsubstituted aromatic group, —$NH_2$, —$NO_2$, —$NHCOCH_3$, —CN, —O—, halogen, —$OCF_3$ or $R^6$ and $R^7$ together form a heterocyclic ring; R is selected from:

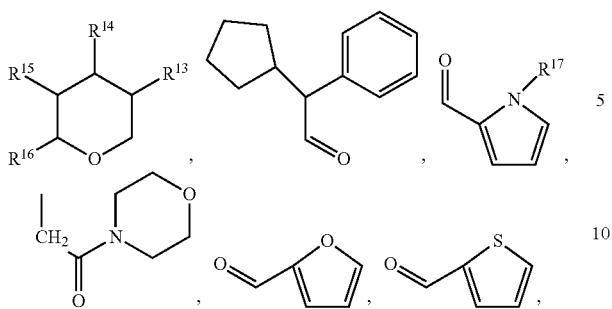

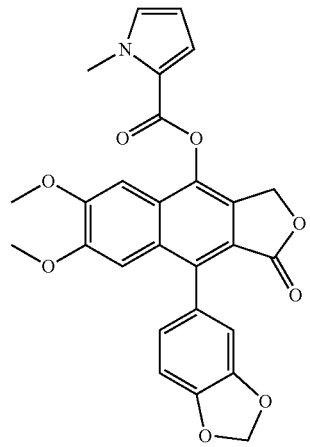 [SMILES: COc1cc2c(OC(=O)c3cccn3C)c3c(c(-c4ccc5c(c4)OCO5)c2cc1OC)C(=O)OC3]

—H, —C(O)CH$_2$Cl, SOO—CH$_3$, —SOOPh, —CH$_2$C(O)N(CH$_3$)$_2$, —C(O)NHPh, —C(O)NHPhOH, —C(S)NHPh, —CH$_2$Ph, —COAr, —SOOAr, —CONHAr, —CH$_2$Ar, —CSNHAr; R$^{11}$ and R$^{12}$ each independently is selected from —H, or R$^{11}$ and R$^{12}$ can be substituted or unsubstituted 5- or 6-membered ring such as lactone, —C(O)O-alkyl such as —C(O)OC$_2$H$_5$;

In a preferred aspect of the invention, compound of Formula V is provided:

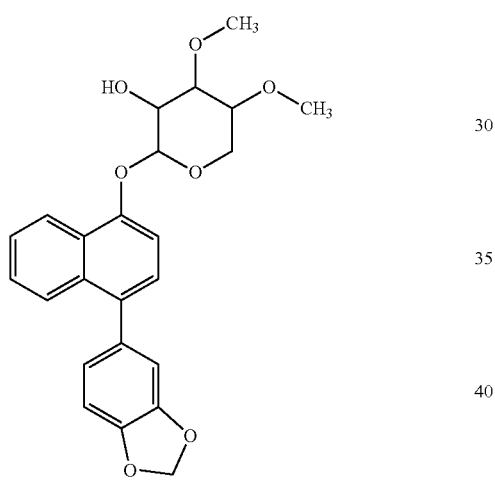

In another preferred aspect, compound of Formula VI is provided:

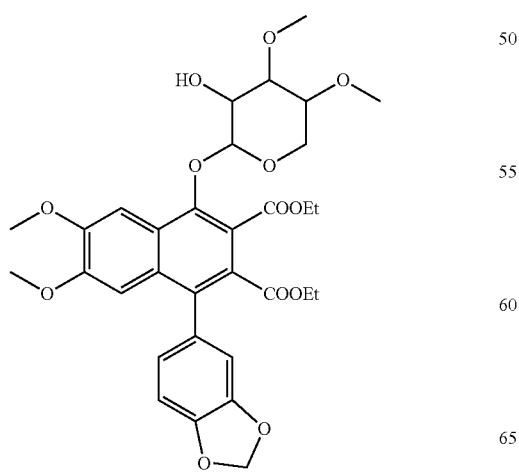

In another aspect, compound of Formula VII is provided:

In another aspect, compound of Formula VIII is provided:

In a further aspect, compound of Formula IX is provided:

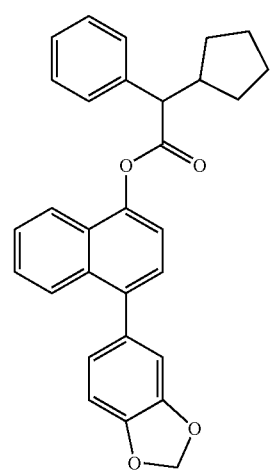 [SMILES: O=C(Oc1ccc(-c2ccc3c(c2)OCO3)c2ccccc12)C(c1ccccc1)C1CCCC1]

In a further aspect, a compound of Formula X is provided:

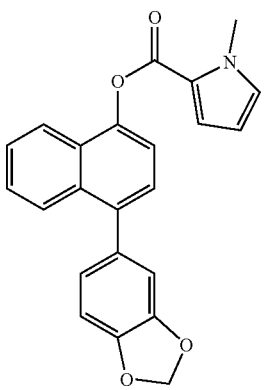 [SMILES: Cn1cccc1C(=O)Oc1ccc(-c2ccc3c(c2)OCO3)c2ccccc12]

In a further aspect, a compound of Formula XI is provided:

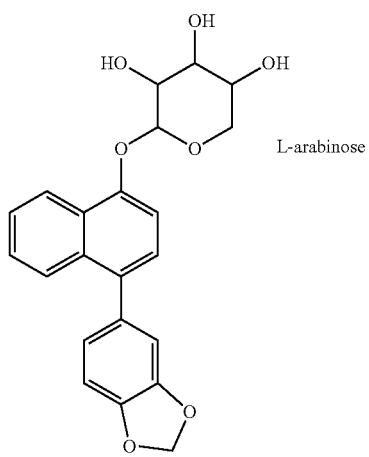 [SMILES: OC1COC(Oc2ccc(-c3ccc4c(c3)OCO4)c3ccccc23)C(O)C1O]

In a further aspect, a compound of Formula XII is provided:

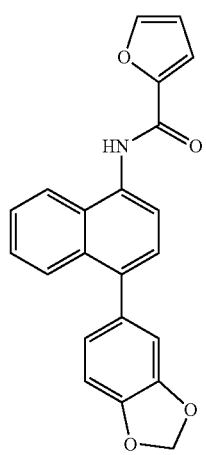 [SMILES: O=C(Nc1ccc(-c2ccc3c(c2)OCO3)c2ccccc12)c1ccco1]

In a further aspect, a compound of Formula XIII is provided:

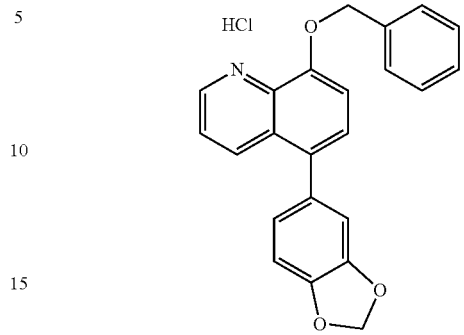

In a further aspect, a compound of Formula XIV is provided:

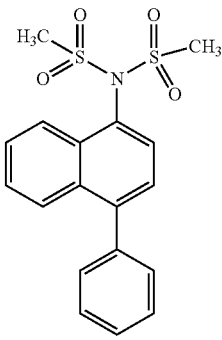 [SMILES: CS(=O)(=O)N(c1ccc(-c2ccccc2)c2ccccc12)S(C)(=O)=O]

The present invention provides compounds V to XIV for use in treatment of cancer.

In further aspect of the present invention, compounds of Formula V to XIV for use in the treatment of cancer is provided. The cancer can be breast, oral, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, or stomach cancer.

In a preferred aspect of the present invention, the compounds of Formula V or VI can be for use in the treatment of breast and/or prostate cancer.

In yet another aspect of the present invention, a pharmaceutical composition having a compound of Formula V to Formula XIV and pharmaceutically acceptable excipient including carrier, adjuvant, vehicle or mixtures thereof is provided. The composition of the present invention can be used in the treatment of cancer. The cancer includes breast, oral, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, or stomach cancer.

In a preferred aspect, the composition can be used for the treatment of breast and/or prostate cancer.

In a further aspect of the present invention, a method of treating cancer by administering an effective amount of at least one of compounds of present invention is provided. In a preferred aspect, a method of treating cancer including administering an effective amount of compound of formula V or VI is provided. The method of treatment including administering an effective amount of compound of formula V or VI, can be for treating breast cancer and/or a prostate cancer.

DESCRIPTION OF THE INVENTION

Figure 1:
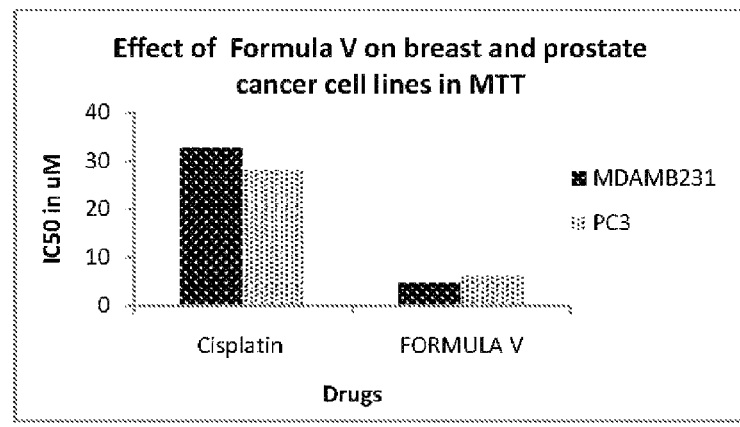
FIG. 1. Shows effect of compound of Formula V on cancer cell lines MDAMB231 and PC3 compared to standard chemo therapeutic drug Cisplatin in MTT assay.
Figure 2:
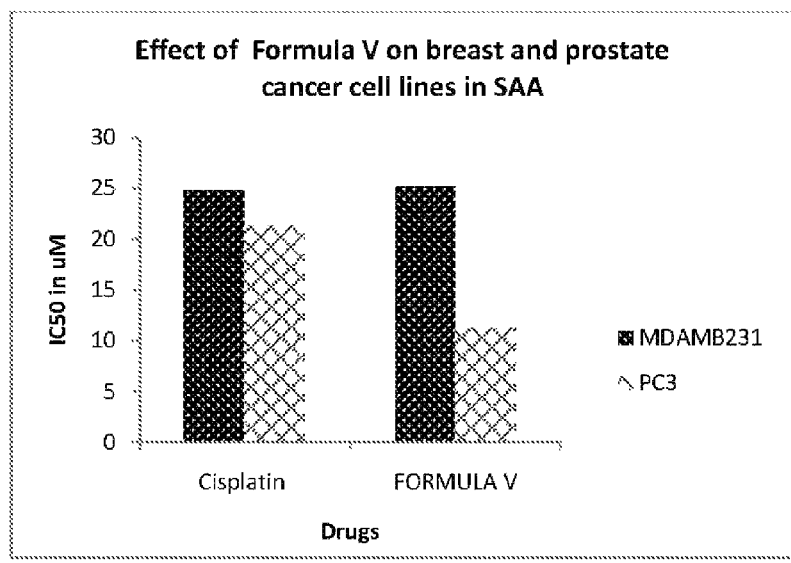
FIG. 2. Shows effect of compound of Formula V on cancer cell lines MDAMB231 and PC3 compared to standard chemo therapeutic drug Cisplatin in soft Agar Assay.
Figure 3:
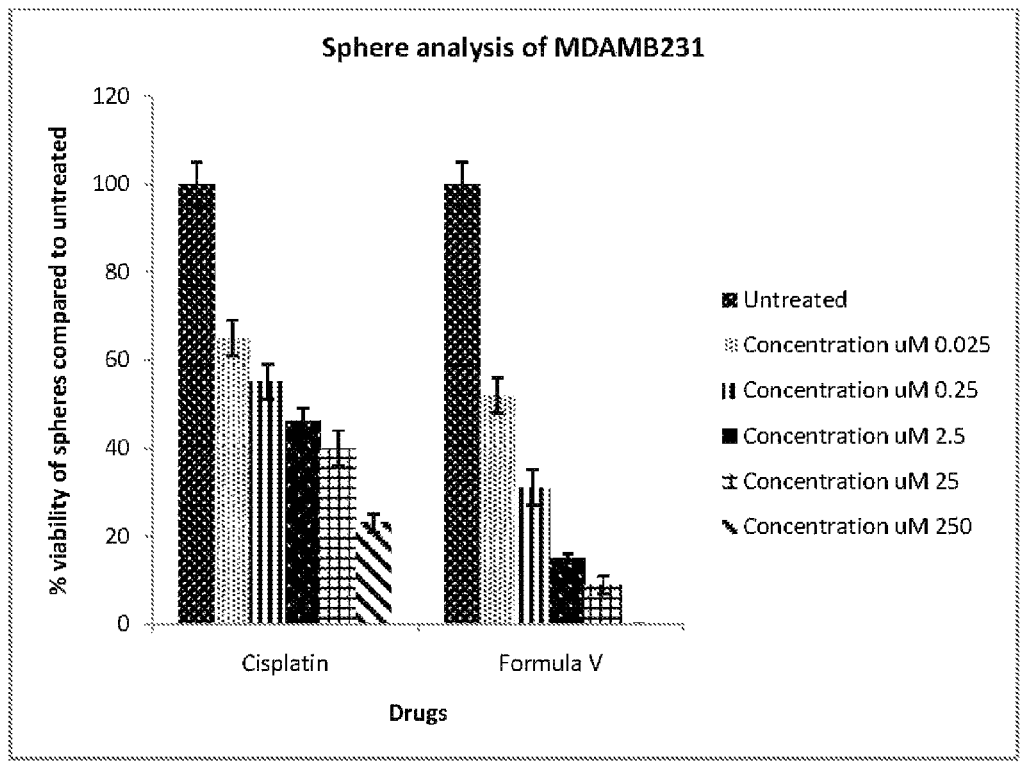
FIG. 3 Shows the percentage viability of spheres of MDAMB231 in the presence of compound of Formula V compared to standard chemo therapeutic drug FIG. 4 Shows that there is decrease in percentage viability of spheres of PC3 in presence of Formula V compared to standard chemotherapeutic drug Cisplatin.
Figure 4:
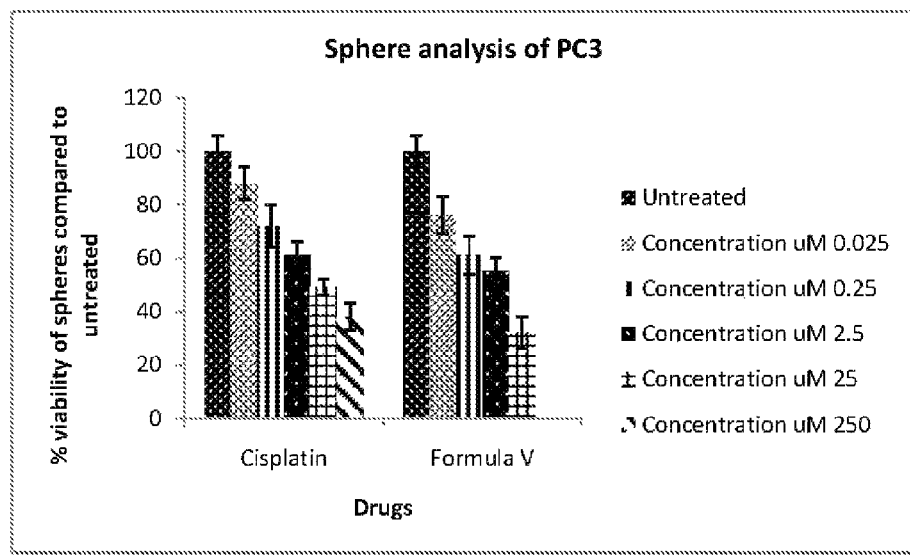
Figure 5:
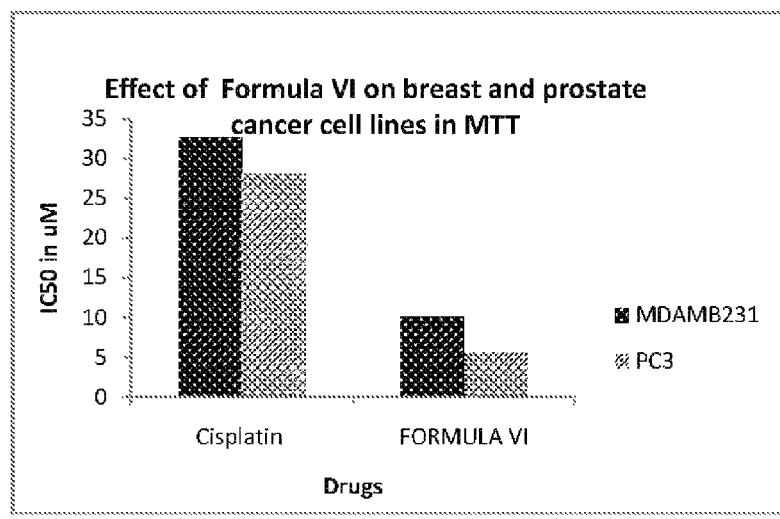
FIG. 5 Shows the effect of compound of Formula VI on MDAMB231 and PC3 cancer cell lines compared to standard chemo therapeutic drug Cisplatin in MTT assay.
Figure 6:
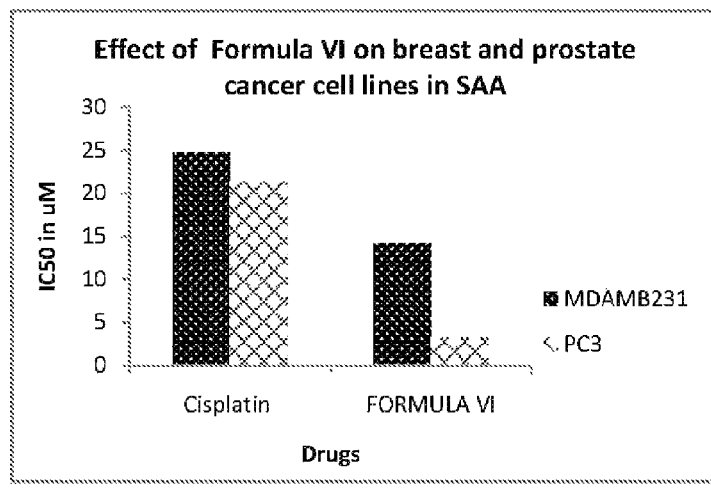
FIG. 6 Shows the effect of compound of Formula VI on MDAMB231 and PC3 cancer cell lines compared to standard chemo therapeutic drug Cisplatin in Soft Agar Assay.
Figure 7:
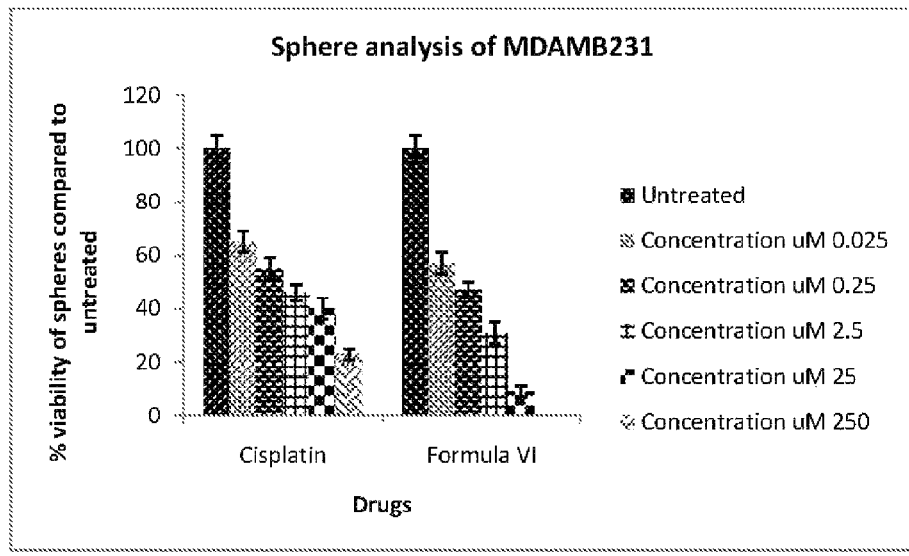
FIG. 7 Shows that there is decrease in percentage viability of spheres of MDAMB231 in presence of compound of Formula VI compared to standard chemo therapeutic drug Cisplatin
Figure 8:
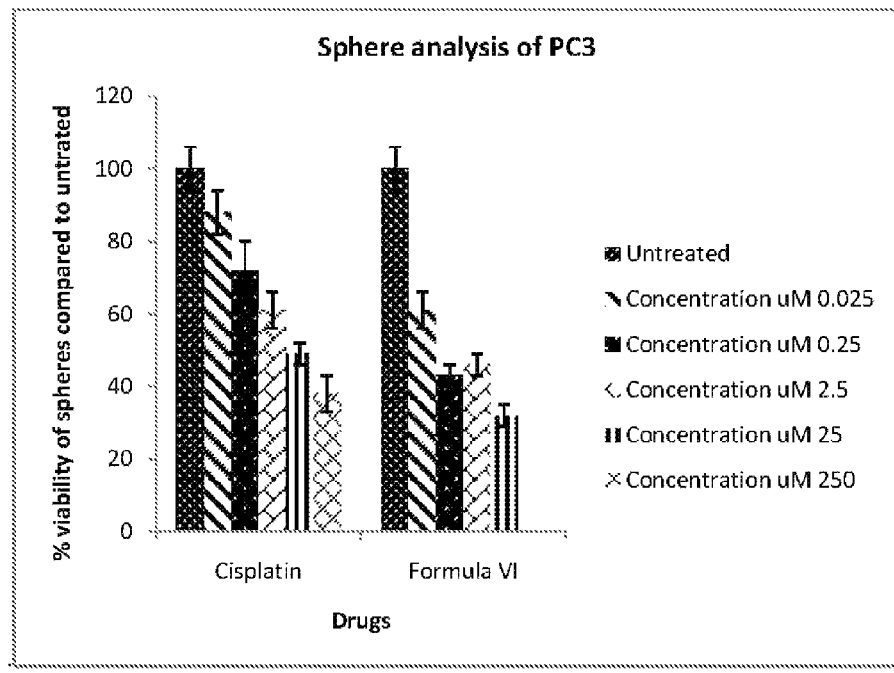
FIG. 8 shows that there is decrease in percentage viability of spheres of PC3 in presence of compound of Formula VI compared to standard chemotherapeutic drug Cisplatin.
Figure 9:
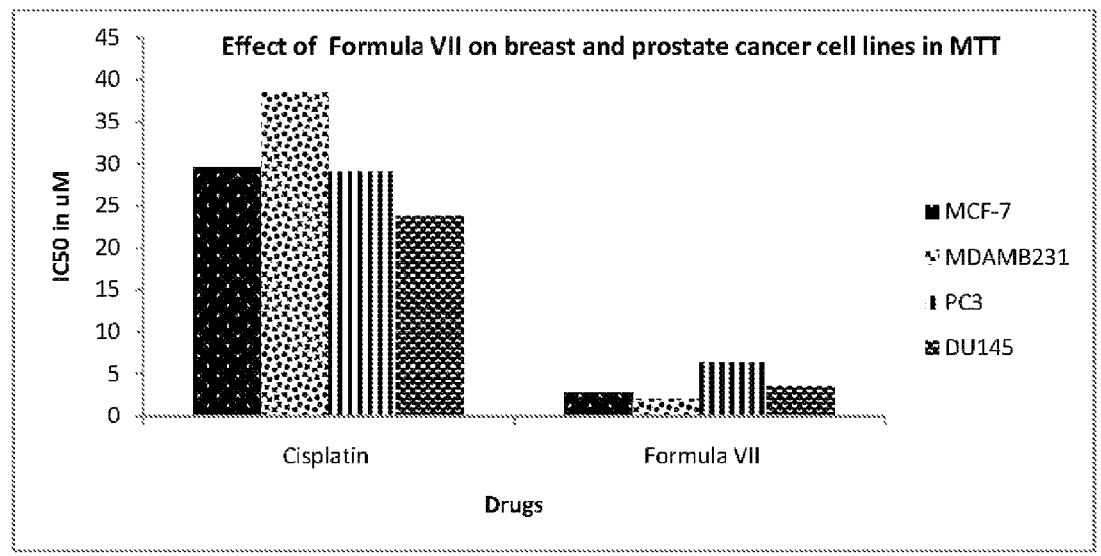
FIG. 9. Shows compound of Formula VII exhibits higher anticancer activity on MCF7, MDAMB231, PC3 and DU145 cell lines compared to standard chemo therapeutic drug Cisplatin in MTT assay.
Figure 10:
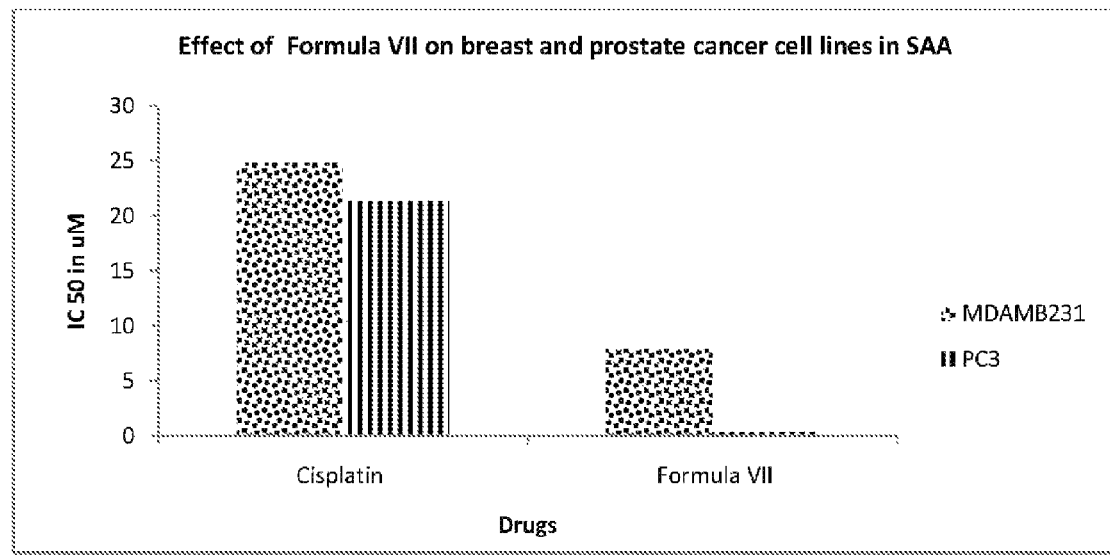
FIG. 10. Shows that compound of Formula VII exhibits higher anticancer activity on MDAMB231. PC3 cell lines compared to standard chemotherapeutic drug Cisplatin in Soft Agar Assay.
Figure 11:
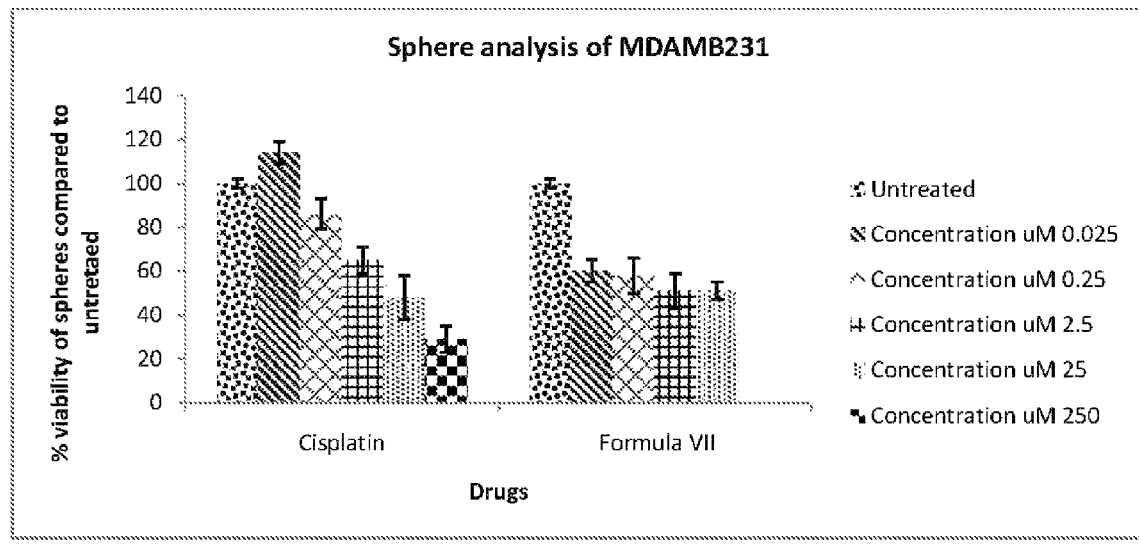
FIG. 11 Shows there is decrease in percentage viability of spheres of MDAMB231 in presence of compound of Formula VII compared to standard chemo therapeutic drug Cisplatin.
Figure 12:
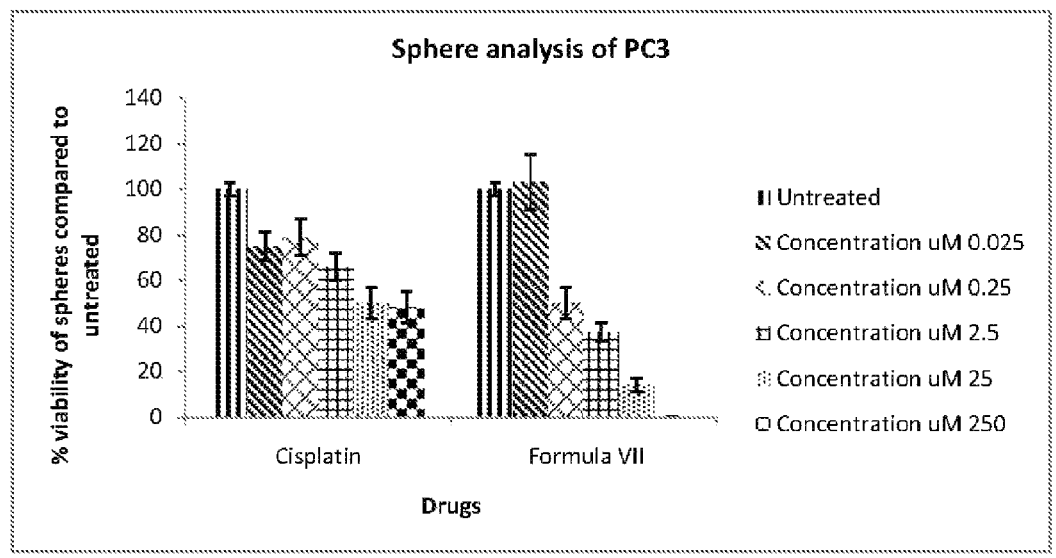
FIG. 12 Shows that there is decrease in percentage viability of spheres of PC3 in presence of compound of Formula VII compared to standard chemotherapeutic drug Cisplatin.
Figure 13:
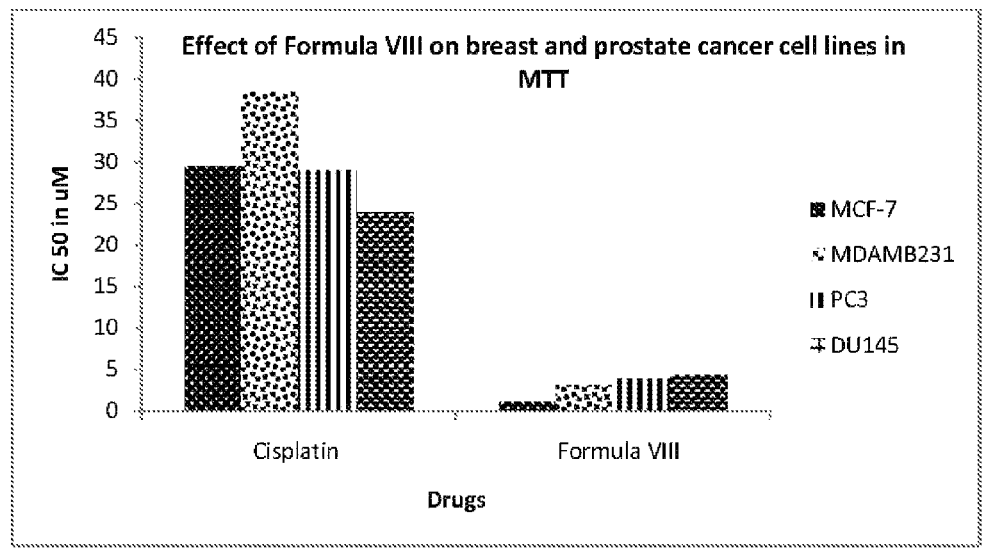
FIG. 13 Shows that compound of Formula VIII exhibits higher anticancer activity on MCF7, MDAMB231, PC3 and DU145 cell lines compared to standard chemotherapeutic drug Cisplatin in MTT assay.
Figure 14:
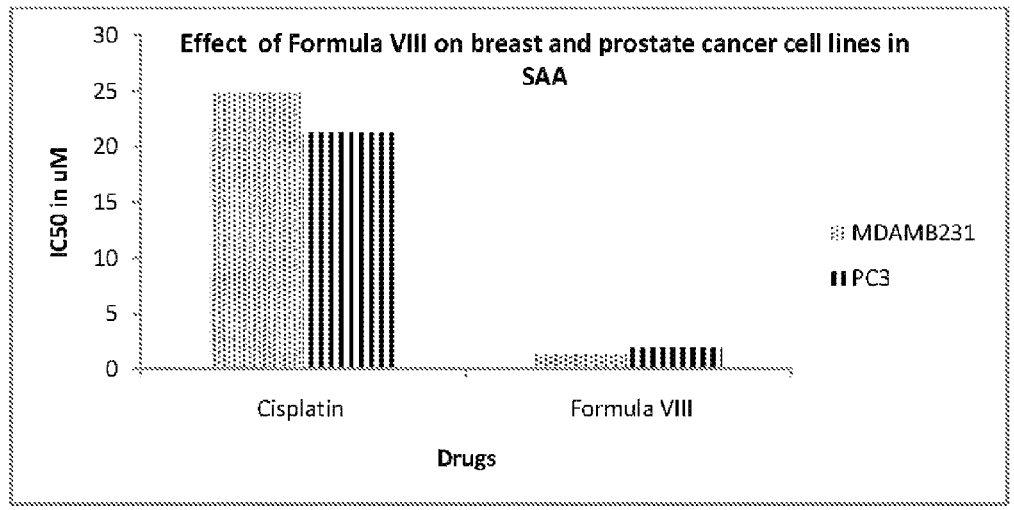
FIG. 14 Shows that compound of Formula VIII exhibits higher anticancer activity on MDAMB231, PC3 cell lines compared to standard chemotherapeutic drug Cisplatin in Soft Agar Assay.
Figure 15:
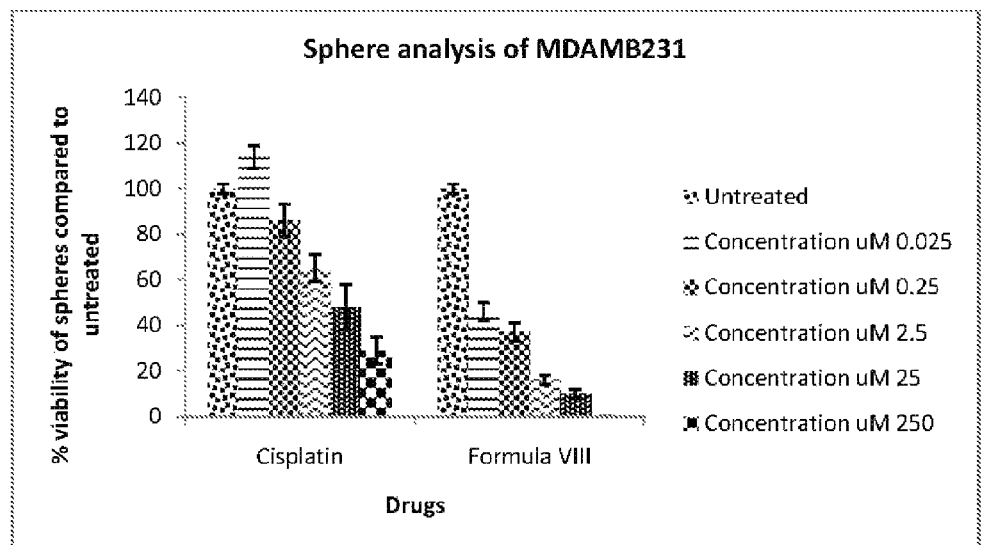
FIG. 15 shows that there is decrease in percentage viability of spheres of MDAMB231 in presence of compound of Formula VIII compared to standard chemo therapeutic drug Cisplatin.
Figure 16:
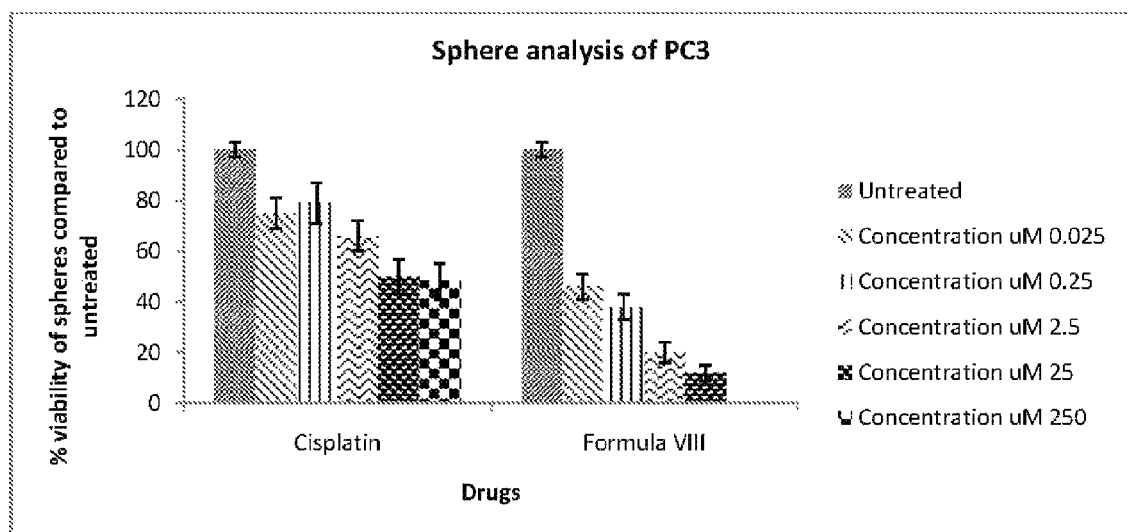
FIG. 16 shows that there is decrease in percentage viability of spheres of PC3 in presence of compound of Formula VIII compared to standard chemotherapeutic drug Cisplatin.
Figure 17:
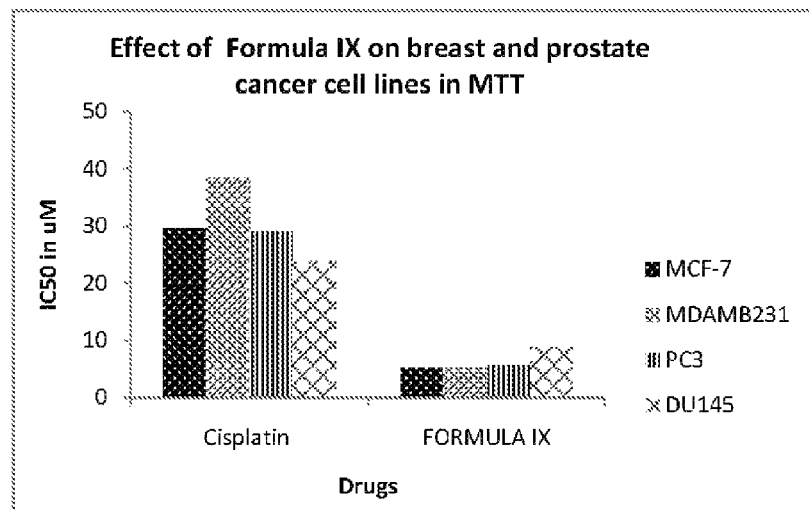
FIG. 17 Shows that compound of Formula IX exhibits higher anticancer activity on MCF7, MDAMB231, PC3, DC145 cell lines compared to standard chemotherapeutic drug Cisplatin in MTT assay.
Figure 18:
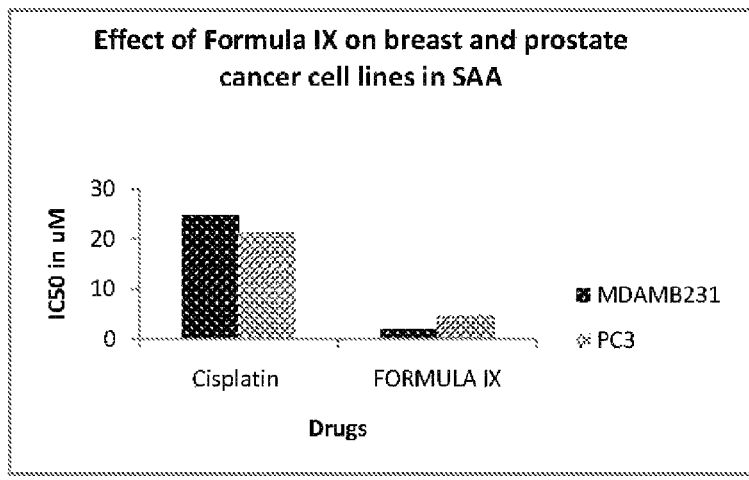
FIG. 18 Shows compound of Formula IX exhibits higher anticancer activity on MDAMB231, PC3 cell lines compared to standard therapeutic drug Cisplatin in Soft Agar Assay.
Figure 19:
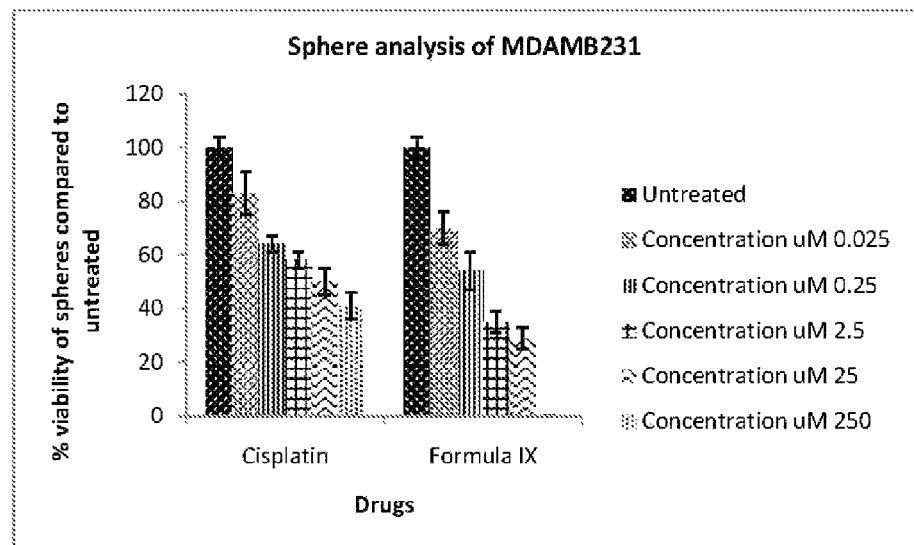
FIG. 19 Shows that there is decrease in percentage viability of spheres of MDAMB231 in presence of compound of Formula IX compared to standard chemo therapeutic drug Cisplatin.
Figure 20:
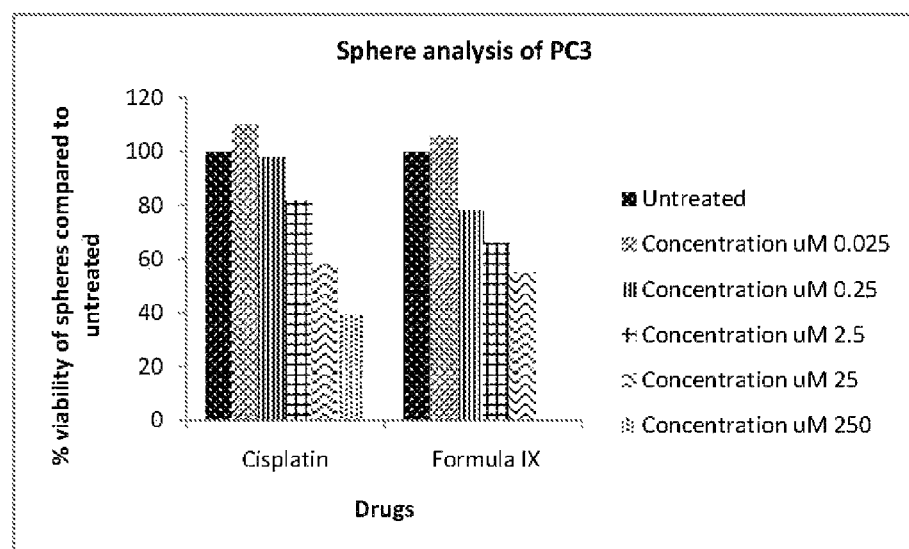
FIG. 20 indicates that there is decrease in percentage viability of spheres of PC3 in presence of compound of Formula IX compared to standard chemotherapeutic drug Cisplatin.
Figure 21:
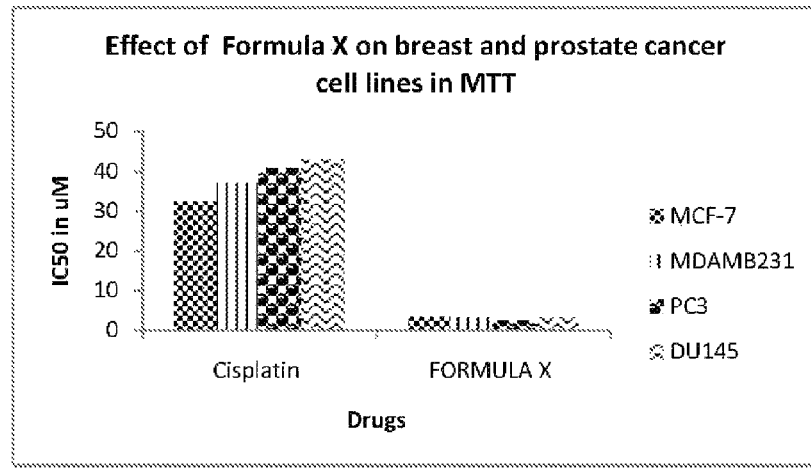
FIG. 21. Shows that compound of Formula X exhibits higher anticancer activity on MCF7, MDMB231, PC3, DU145 cell lines compared to standard chemo therapeutic drug Cisplatin in MTT assay.
Figure 22:
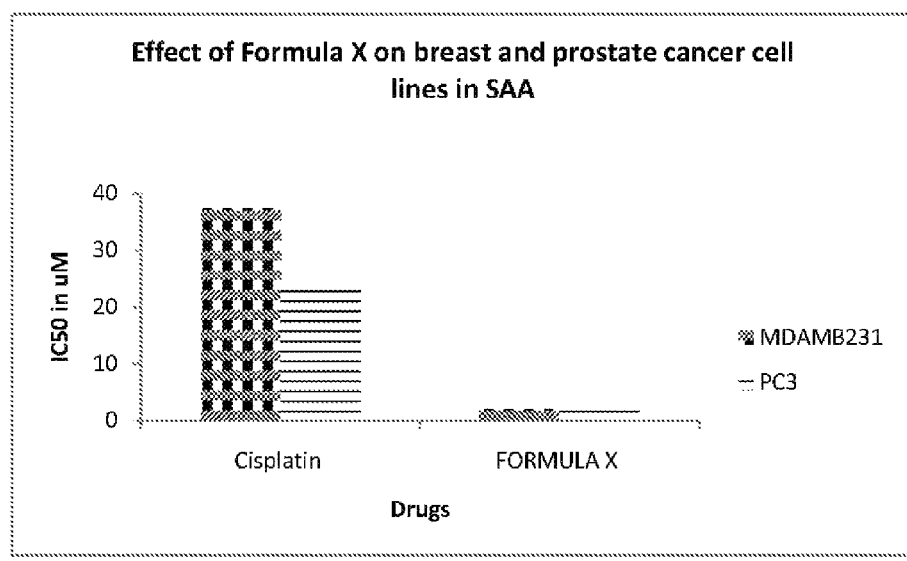
FIG. 22. Shows that compound of Formula X exhibits higher anticancer activity on MDMB231, PC3 cell lines compared to standard chemotherapeutic drug Cisplatin in Soft Agar Assay.
Figure 23:
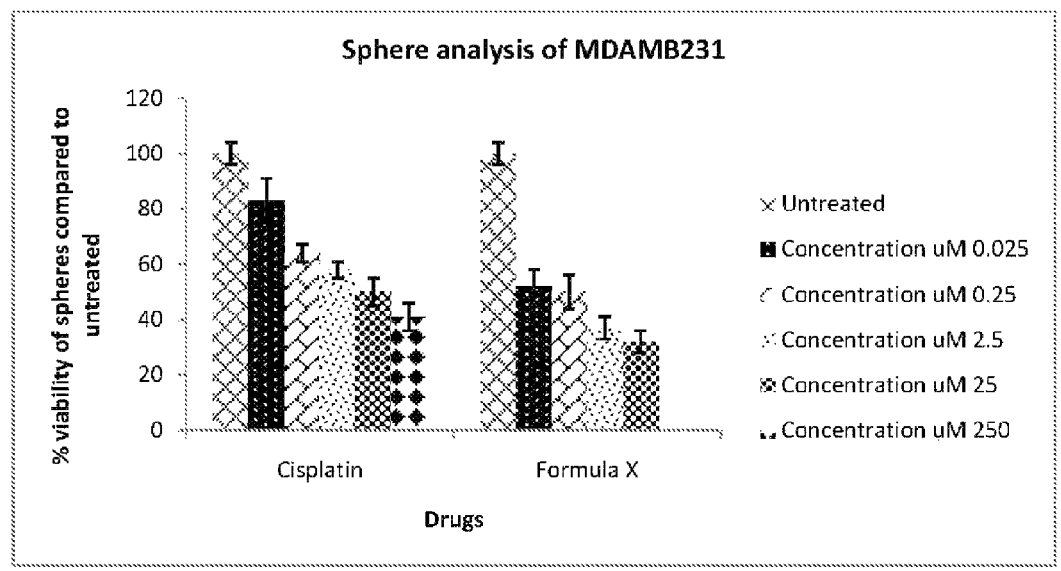
FIG. 23 Shows that there is decrease in percentage viability of spheres of MDAMB231 in presence of compound of Formula X compared to standard chemo therapeutic drug Cisplatin.
Figure 24:
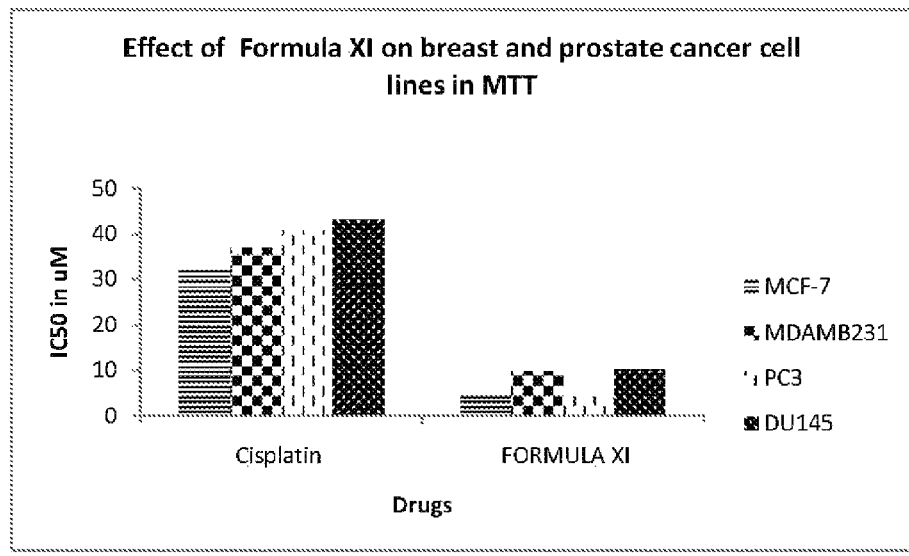
FIG. 24 Shows that compound of Formula XI exhibits higher anticancer activity on MCF7, MDMB231, PC3, DU145 cell lines compared to standard chemo therapeutic drug Cisplatin in MTT Assay.
Figure 25:
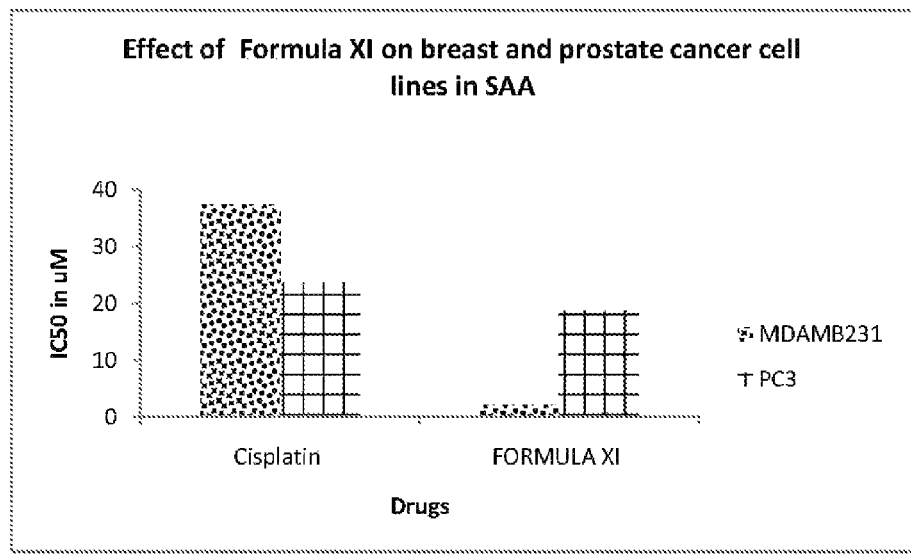
FIG. 25 Shows that compound of Formula XI exhibits higher anticancer activity MDMB231, PC3 cell lines compared to standard chemotherapeutic drug Cisplatin in Soft Agar Assay.
Figure 26:
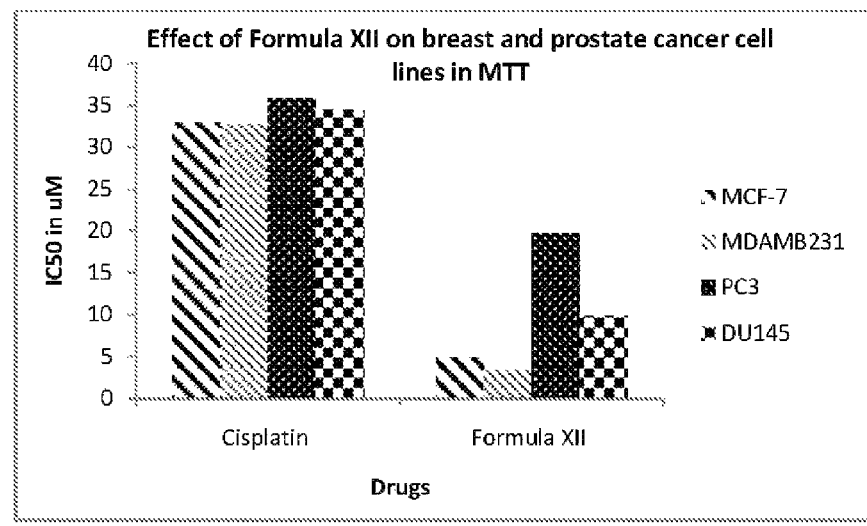
FIG. 26 Shows that compound of Formula XII exhibits higher anticancer activity on MCF7, MDMB231, PC3, DU145 cell lines compared to standard chemo therapeutic drug Cisplatin in MTT Assay FIG. 27 Shows that compound of Formula XII exhibits higher anticancer activity on MDMB231. PC3 cell lines compared to standard chemotherapeutic drug Cisplatin in Soft Agar Assay.
Figure 27:
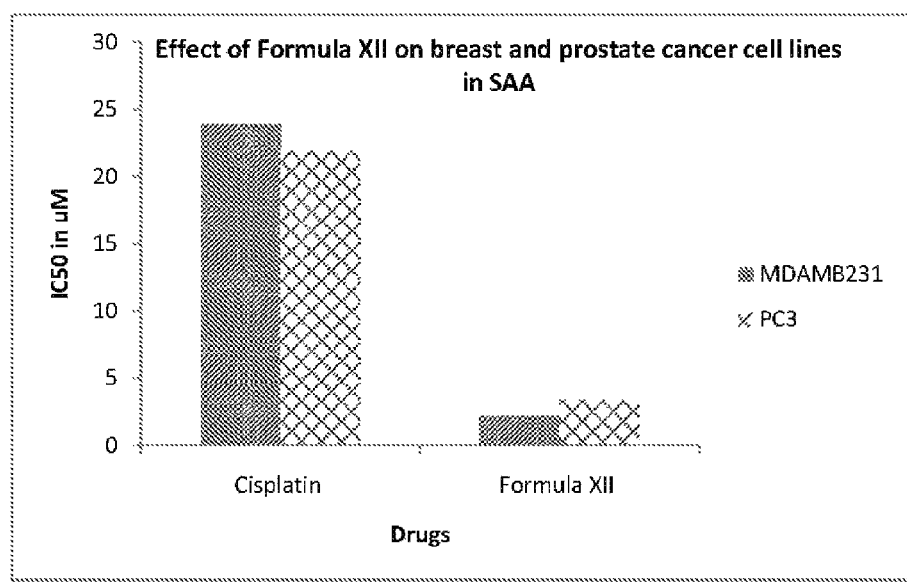
Figure 28:
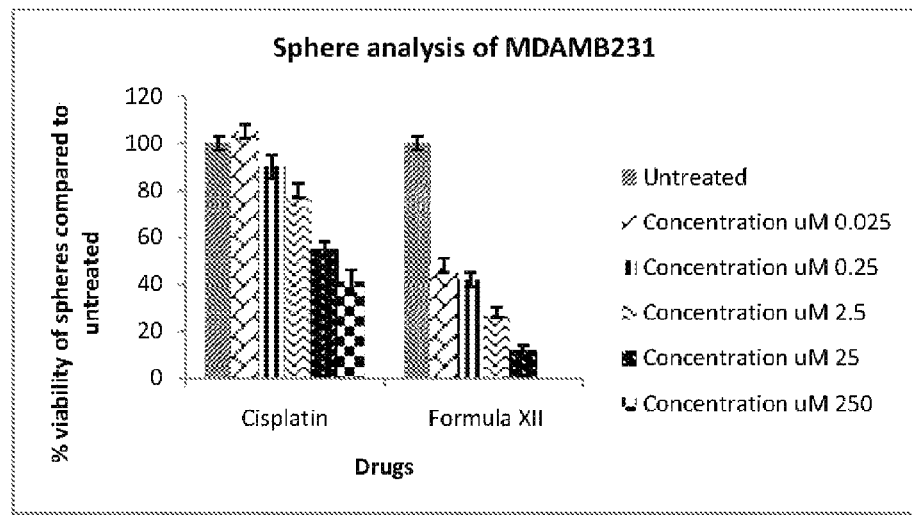
FIG. 28 Shows that percentage viability of spheres of MDAMB231 in presence of compound of Formula XII is similar compared to standard chemo therapeutic drug Cisplatin.
Figure 29:
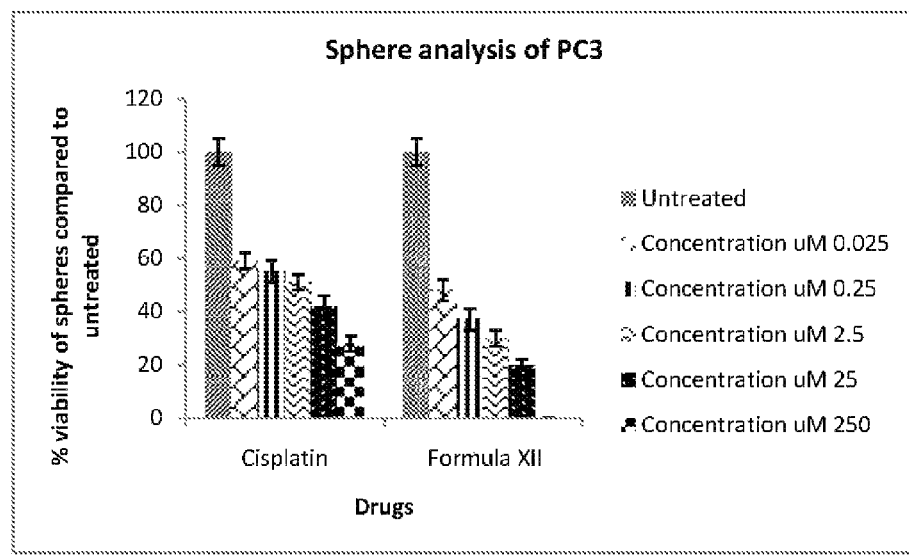
FIG. 29 Shows that percentage viability of spheres of PC3 in presence compound of Formula XII is higher compared to standard chemotherapeutic drug Cisplatin.
Figure 30:
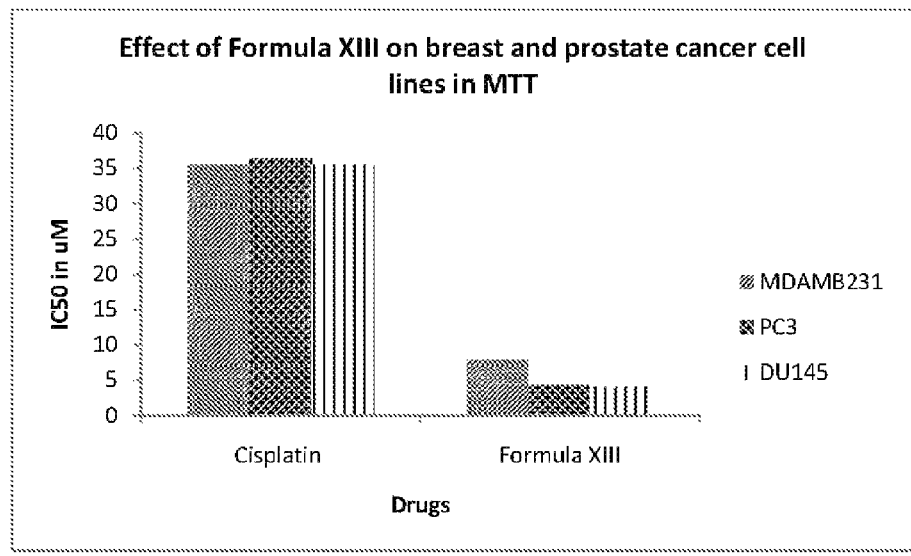
FIG. 30 Shows that compound of Formula XIII exhibits higher anticancer activity on MDMB231, PC3, DU145 cell lines compared to standard chemo therapeutic drug Cisplatin in MTT assay FIG. 31 Shows that compound of Formula XIII exhibits higher anticancer activity on MDMB231, PC3 cell lines compared to standard chemotherapeutic drug Cisplatin in Soft Agar Assay.
Figure 31:
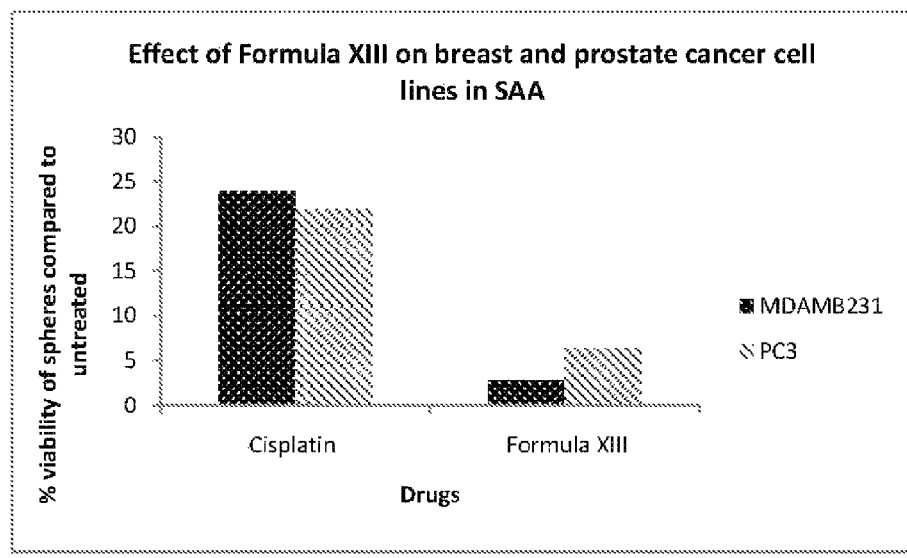
Figure 32:
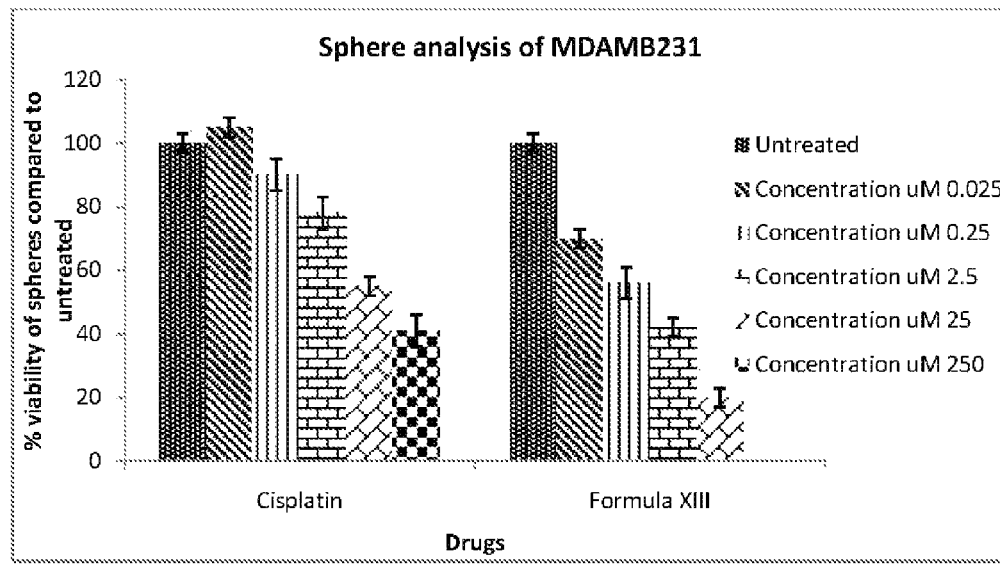
FIG. 32 Shows there is decrease in percentage viability of spheres of MDAMB231 in presence of compound of Formula XIII compared to standard chemo therapeutic drug Cisplatin.
Figure 33:
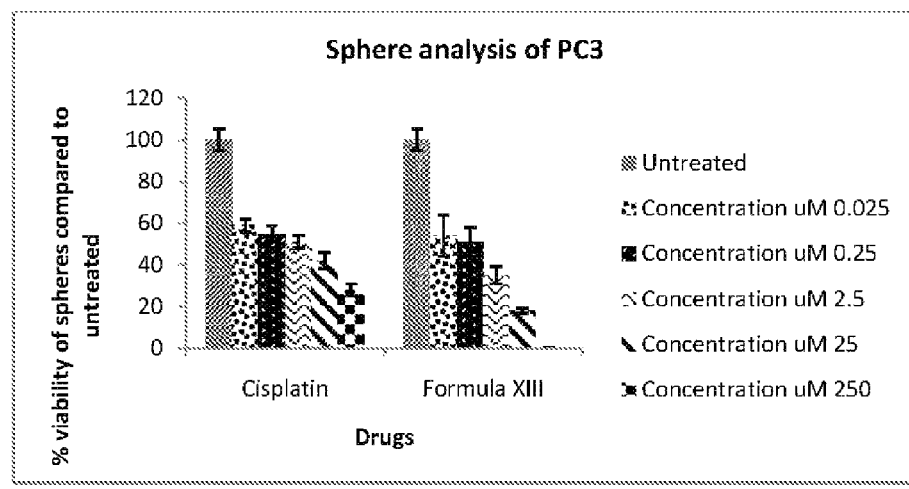
FIG. 33 Shows that there is decrease in percentage viability of spheres of PC3 in presence of compound of Formula XIII compared to standard chemotherapeutic drug Cisplatin.
Figure 34:
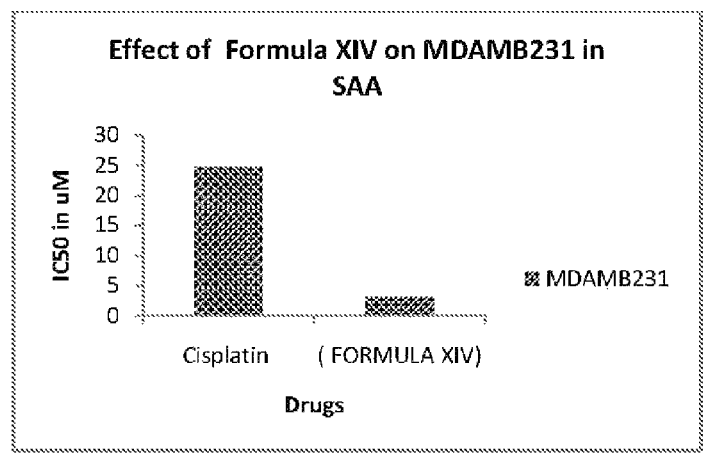
FIG. 34. Shows that compound of Formula XIV exhibits higher anticancer activity on MDMB231 cell line compared to standard chemo therapeutic drug Cisplatin in Soft Agar Assay.
Figure 35:
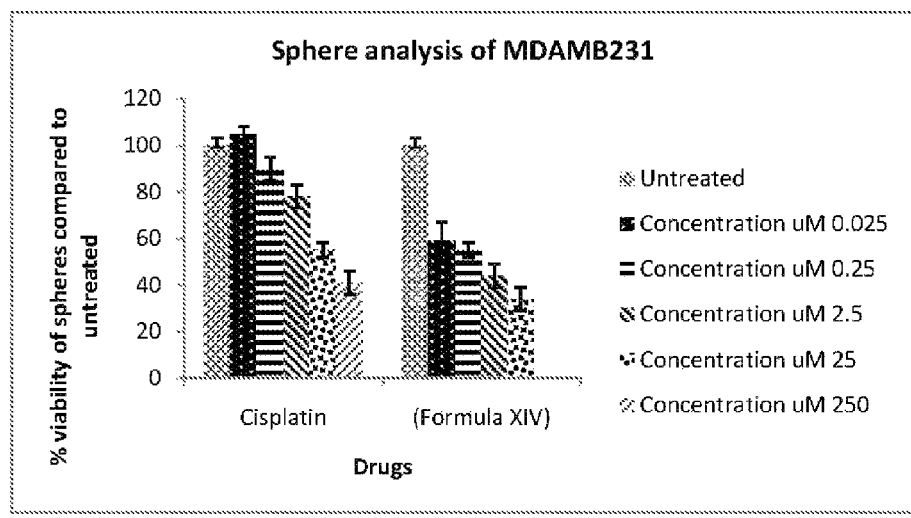
FIG. 35 Shows that there is decrease in percentage viability of spheres of MDAMB231 in presence of compound of Formula XIV compared to standard chemotherapeutic drug Cisplatm.
Figure 36:
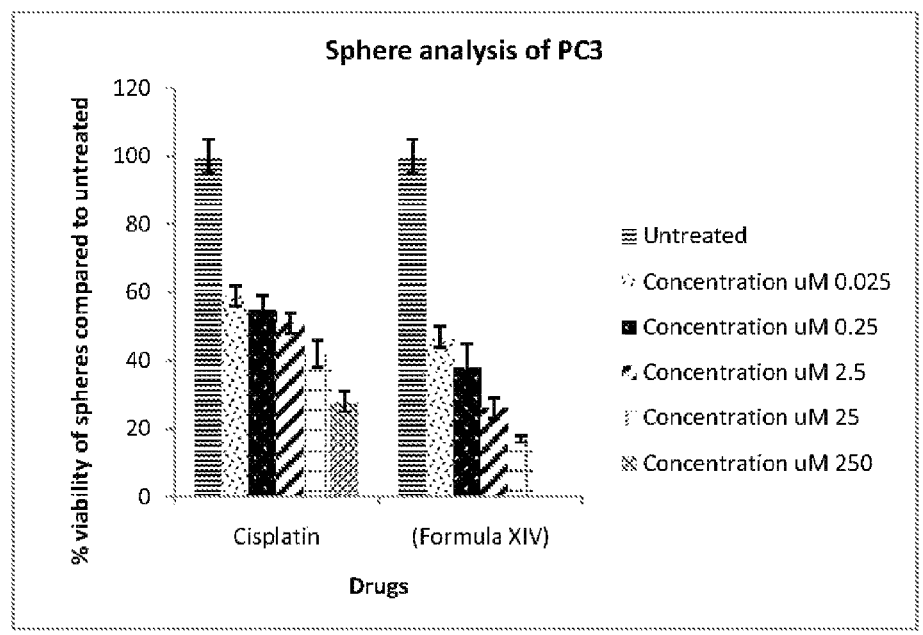
FIG. 36 Shows that there is decrease in percentage viability of spheres of PC3 in presence of compound of Formula XIV compared to standard chemotherapeutic drug Cisplatin.

The present invention relates to compounds for treating various conditions, particularly for inhibition, of uncontrolled cell proliferation. Particularly the compounds are effective against cancer stem cells and treating cancer.

The present invention relates to compound of Formula 1:

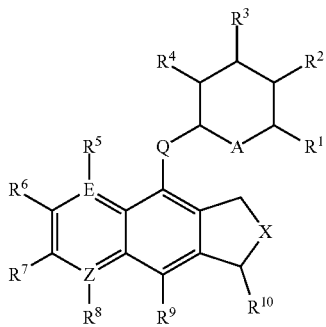

wherein, $R^1$ is selected from —H, —CH$_2$OH; $R^2$ is selected from —H, alkoxy, alkyl, acetyl, $C_3$-$C_8$ acyl group; $R^3$ is selected from alkoxy, alkyl, acetyl, $C_3$-$C_8$ acyl group; $R^4$ is selected from —OH, F, —NH$_2$, —NHCOCH$_3$, alkyl, acetyl, $C_3$-$C_8$ acyl group; $R^5$ is H, Cl; $R^6$ and $R^7$ each independently is selected from H, alkyl, substituted or unsubstituted aromatic group, alkoxy, NH$_2$, NO$_2$, —NHCOCH$_3$, —CN, —O—, halogen, —OCF$_3$ or $R^6$ and $R^7$ together form a heterocyclic ring; $R^8$ is H, Cl; $R^9$ is selected from a substituted or unsubstituted 5- or 6-membered ring, —CH$_2$—O—CH$_2$—COOH $R^{10}$ is =O or H; A is O, —NH, —N-alkyl; Q is O, S, —CH$_2$O—; X is selected from CH$_2$, O, N, S; E is selected from CH, O, N, S; and Z is selected from CH, O, N, S. In one embodiment, the $R^9$ group is

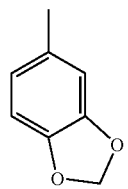

In another embodiment of the present invention, a compound of formula II is provided:

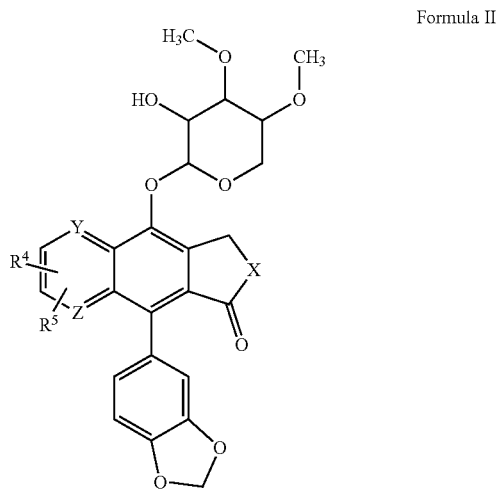

In an embodiment, the present invention provides compounds of Formula III or salts thereof for treating various conditions, particularly for inhibition of uncontrolled cell proliferation. Particularly, the compounds are effective against cancer stem cells.

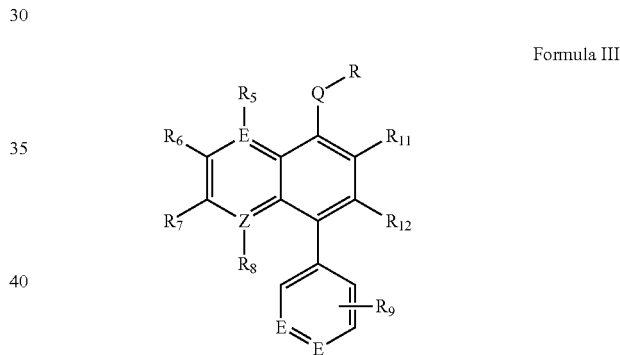

wherein, E and Z is selected from C, O, N, S, salts of N such as N. HCl; Q is O, S, —CH$_2$O—, wherein Y' is selected from —H, alkyl; SOOCH3; $R^5$ is —H, —Cl, when E and/or Z is —C; $R^6$ and $R^7$ each independently is selected from —H, alkoxy, alkyl, substituted or unsubstituted aromatic group, —NH$_2$, —NO$_2$, —NHCOCH$_3$, —CN, —O—, halogen, —OCF$_3$ or $R^6$ and $R^7$ together form a heterocyclic ring; $R^8$ is —H, —Cl, when E and/or Z is —C; $R_9$ is —CH2-O—CH2, —COOH, —X where X can be F, Cl, Br, alkyl such as —CH$_3$, —OH, alkoxy such as —OMe, NHCOCH$_3$, H, NH$_2$; $R^{11}$ and $R^{12}$ each independently is selected from —H. $R^{11}$ and $R^{12}$ can be substituted or unsubstituted 5- or 6-membered ring such as lactone, —C(O)O-alkyl such as —C(O)OC$_2$H$_5$; R is selected from:

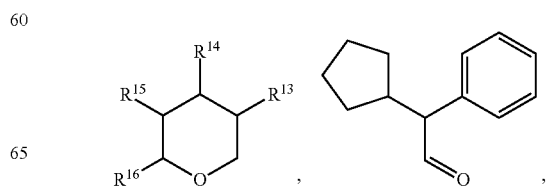

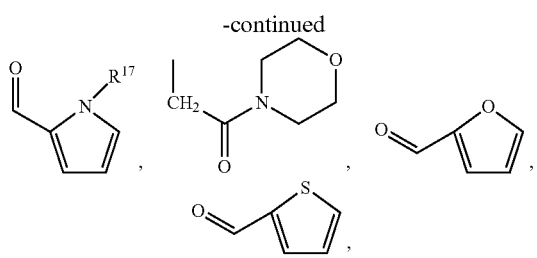

—H, —C(O)CH₂Cl, —SOO—CH₃, —SOOPh, —CH₂C(O)N(CH₃)₂, —C(O)NHPh, —C(O)NHPhOH, —C(S)NHPh, —CH₂Ph, —COAr, —SOOAr, —CONHAr, —CH₂Ar, —CSNHAr, wherein, $R^{13}$ is selected from —OH, —NH₂, —NHCOCH₃, X=F, Cl, Br, alkyl, acetyl, C₃-C₈ acyl group; $R^{14}$ is, selected from alkoxy, —OMe, —OH, NH₂, —NHCOCH₃, X=F, Cl, Br, alkyl, acetyl, C₃-C₈ acyl group; $R^{15}$ is selected from alkoxy, —OMe, —OH, —H, Br, NH₂, N=F, Cl, Br alkyl, acetyl, C₃-C₅ acyl group; $R^{16}$ is selected from —H, —CH₂OH, —OH, alkyl, alkoxy; $R^{17}$ is selected from alkyl. According to an embodiment of the present invention, a compound of Formula IV or salts thereof is provided to prevent cell proliferation:

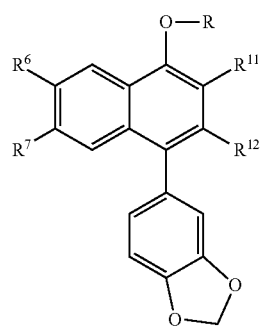

Formula IV wherein, R, $R^6$, $R^7$, $R^{11}$ and $R^{12}$ have the meaning as assigned above. In a preferred embodiment of the present invention, a compound of Formula V or salts thereof is provided to prevent cell proliferation:

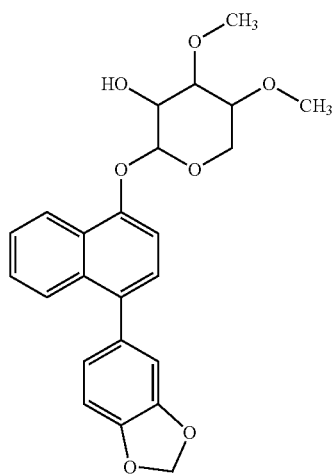

Formula V

The compound of Formula V of the present invention are active on Breast and prostate cancer cell lines. Further, compound of Formula V is potent compared to standard chemotherapeutic drug Cisplatin. The compound of Formula V does not show activity on normal lymphocytes.

In another preferred embodiment of the present invention, a compound of Formula VI or salts thereof is provided to prevent cell proliferation:

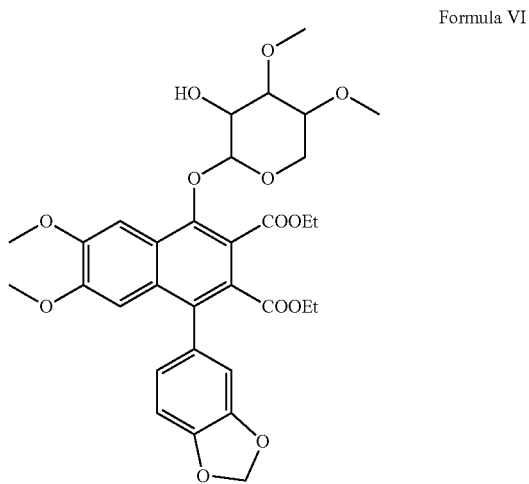

Formula VI

Compound of Formula VI shows activity in breast and prostate cancer cell lines. Further, compound of Formula VI is potent compared to standard chemotherapeutic drug Cisplatin. The compound of Formula VI does not show activity on normal lymphocytes.

In an embodiment, the present invention provides compounds that demonstrate anticancer and anti-cancer stem cell activity particularly in breast and prostate cancer cell lines. In an embodiment, compound of formula VII is provided:

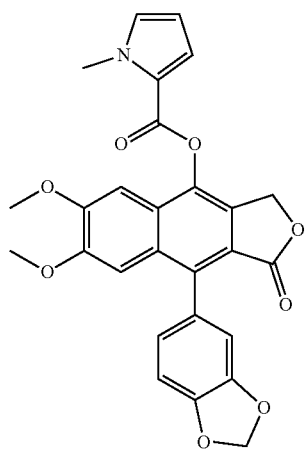

Formula VII

Compound of Formula VII shows activity in breast and prostate cancer cell lines. The compound of Formula VII does not show activity on normal lymphocytes.

In another embodiment, the present invention provides compound of Formula VIII that prevents cell proliferation.

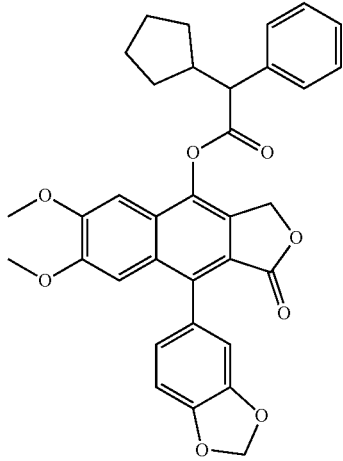

Formula VIII

Compound of Formula VIII shows activity in breast and prostate cancer cell lines and does not show activity on normal lymphocytes.

In a further embodiment of the present invention compound of Formula IX is provided that prevents cell proliferation:

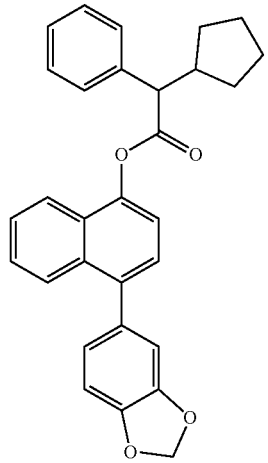

Formula IX

Compound IX of the present invention shows activity in breast and prostate cancer cell lines.

In yet another embodiment of the present invention, compound of Formula X is provided that prevents cell proliferation:

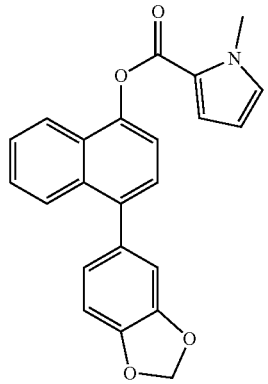

Formula X

Compound of formula X shows activity in breast and prostate cancer cell lines and does not show activity in normal lymphocytes.

In yet another embodiment, the present invention provides compound of Formula XI that prevents cell proliferation:

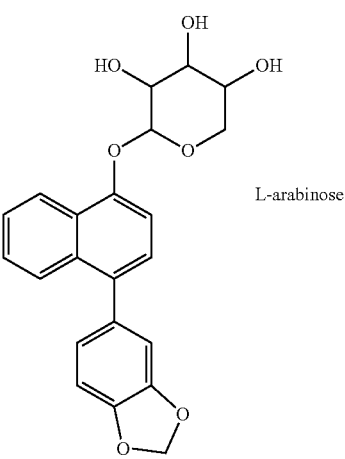

Formula XI

L-arabinose

Compound of formula XI shows activity in breast and prostate cancer cell lines

In yet another embodiment, the present invention provides compound of Formula XII that prevents cell proliferation:

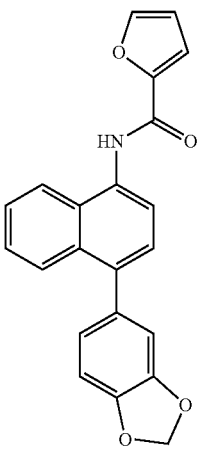

Formula XII

Compound of formula XII shows activity in breast and prostate cancer cell lines. In a further embodiment, the present invention provides compound of Formula XIII that prevents cell proliferation:

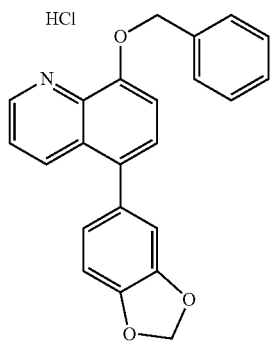

Formula XIII

Compound of formula XIII shows activity in breast and prostate cancer cell lines.

In a further aspect, a compound of Formula XIV is provided:

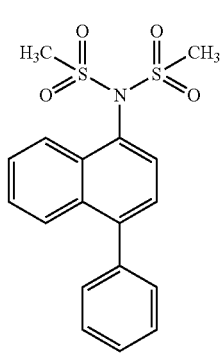

Formula XIV

Compound of formula XIV shows activity in breast cancer cell lines

In an embodiment of the present invention, compounds of formula V to XIV of the present invention for use in the treatment of cancer is provided. Preferably, the compound of Formula V and VI are provided for use in the treatment of cancer. The cancer can be the cancer is breast, oral, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, or stomach cancer. In a preferred embodiment, the compounds of Formula V and VI for use in the treatment of breast and/or prostate cancer is provided.

In a further embodiment, pharmaceutical compositions including the compounds of the present invention, pharmaceutically acceptable excipient including carrier, adjuvant, vehicle or mixtures thereof are provided. Preferably, pharmaceutical compositions including compounds of Formula V and VI pharmaceutically acceptable excipient including carrier, adjuvant, vehicle or mixtures thereof are provided. The pharmaceutical excipient can further include one or more binders, diluents, disintegrants, glidants, lubricants, stabilizers, surface active agents or pH-adjusting agents.

In certain embodiments, the amount of compound in compositions may be such that it is effective to treat cancer in a subject in the need thereof. In certain embodiments, the composition may comprise between the biologically effective dose and the maximum tolerated dose of the compound of the invention or it's pharmaceutically acceptable salt, ester, or salt of an ester.

In certain embodiments, a composition of this invention may be formulated for administration to a subject in the need thereof. The pharmaceutical compositions of the present invention may be formulated into a suitable dosage form to be administered orally, parenterally, by inhalation spray, topically, rectally, nasally, buccally, vaginally or via an implanted reservoir. Compositions of the present invention may be formulated into dosage forms including liquid, solid, and semisolid dosage forms. The term "parenteral" as used herein includes subcutaneous, intravenous, intraperitoneal, intramuscular, intra-articular, intrasynovial, intrastemal, intrathecal, intrahepatic, intralesional and intracranial injection or infusion techniques. Preferably, the compositions are administered orally, intravenously or intraperitoneally.

The present invention also includes the composition including the compounds of the present invention of Formula V to XIV, preferably compound of Formula V or VI for use in the treatment of cancer including cancer is breast, oral, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, or stomach cancer. In a preferred embodiment, the composition of the present invention is for the treatment of breast, and/or prostate cancer.

In certain embodiments of the present invention disclose a formulation comprising the compounds of the present invention along with other active agents or pharmaceutically acceptable excipients, etc.

In an embodiment, a pharmaceutical composition comprises the aforesaid compounds with another active agent such as but are not limited to imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorclbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane, Actinomycin-D, Adriamycin, Adrucil, Afinitor, Agrylin, Ala-Cort, Aldesleukin, Alemtuzumab, ALIMTA, Alitretinoin, Alkaban-AQ, Alkeran, All-transretinoic Acid, Alpha Interferon, Altretamine, Amethopterin, Amifostine, Aminoglutethimide, Anagrelide, Anandron, Anastrozole, Arabinosylcytosine, Ara-C, Aranesp, Aredia, Arimidex, Aromasin, Arranon, Arsenic Trioxide, Arzerra, Asparaginase, ATRA, Avastin, Azacitidine, BCG, BCNU, Bendamustine, Bevacizumab, Bexarotene, BEXXAR, Bicalutamide, BiCNU Aromasin, Blenoxane. Bleomycin, Bortezomib, Busulfan, Busulfex, C225, Calcium Leucovorin, Campath, Camptosar, Camptothecin-11, Capecitabine, Carac, Carboplatin, Carmustine, Carmustine Wafer, Casodex, CC-5013, CCI-779, CCNU, CDDP, CeeNU, Cerubidine, Cetuximab, Chlorambucil, Citrovorum Factor, Cladribine, Cortisone, Cosmegen, CPT-11, Cytadren, Cytosar-U, Cytoxan, Dacarbazine, Dacogen, Dactinomycin, Darbepoetin Alfa, Dasatinib, Daunomycin, Daunorubicin Hydrochloride, Daunorubicin Liposomal, DaunoXome, Decadron, Decitabine, Delta-Cortef, Deltasone, Denileukin, Diftitox, DepoCyt, Dexamethasone, Dexamethasone Acetate, Dexamethasone Sodium Phosphate, Dexasone, Dexrazoxane, DHAD, DIC, Diodex, Docetaxel, Doxil, Doxorubicin, Doxorubicin Liposomal, Droxia, DTIC, DTIC-Dome, Duralone, Efudex, Eligard, Ellence, Eloxatin, Elspar, Emcyt, Epirubicin, Epoetin Alfa, Erbitux, Erlotinib, Erwinia L-asparaginase, Estramustine, Ethyol, Etopophos, Etoposide, Etoposide Phosphate, Eulexin, Everolimus, E vista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab, ozogamicin, Gemzar Gleevec, Gliadel Wafer, GM-CSF, Goserelin, Granulocyte—Colony Stimulating Factor, Granulocyte Macrophage Colony Stimulating Factor, Halotestin, Herceptin, Hexadrol, Hexalen, Hexamethylmelamine, HMM, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibritumomab, Tiuxetan, Idamycin, Idarubicin Ifex, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A (interferon alfa-2b), Iressa, Irinotecan, Isotretinoin, Ixabepilone, Ixempra, Kidrolase, Lanacort, Lapatinib, L-asparaginase, LCR, Lenalidomide, Letrozole, Leucovorin, Leukeran, Leukine, Leuprolide, Leurocristine, Leustatin, Liposomal Ara-C, Liquid Pred, Lomustine, L-PAM, L-Sarcolysin, Lupron, Lupron Depot, Matulane, Maxidex, Mechlorethamine, Mechlorethamine Hydrochloride, Medralone, Medrol, Megace Megestrol, Megestrol Acetate, Melphalan, Mercaptopurine, Mesna, Mesnex, Methotrexate, Methotrexate Sodium, Methylprednisolone, Meticorten, Mitomycin, Mitomycin-C, Mitoxantrone, MTC, MTX, Mustargen, Mustine, Mutamycin, Myleran, Mylocel, Mylotarg, Navelbine, Nelarabine, Neosar, Neulasta, Neumega, Neupogen, Nexavar, Nilandron, Nilotinib, Nilutamide, Nipent, Nitrogen Mustard, Novaldex, Novantrone, Nplate, Octreotide, Octreotide acetate, Ofatumumab, Oncospar, Oncovin, Ontak, Onxal, Oprelvekin, Orapred, Orasone, Oxaliplatin, Paclitaxel, Paclitaxel Protein-bound, Pamidronate, Panitumumab, Panretin, Paraplatin, Pazopanib, Pediapred, PEG Interferon, Pegaspargase, Pegfilgrastim, PEG-INTRON, PEG-L-asparaginase, PEMETREXED, Pentostatin, Phenylalanine Mustard, Platinol, Platinol-AQ, Prednisolone, Prednisone, Prelone, Procarbazine, PROCRIT, Proleukin, Prolifeprospan 20 with Carmustine Implant, Purinethol, Raloxifene, Revlimid, Rheumatrex, Rituxan, Rituximab, Roferon-A (Interferon Alfa-2a), Romiplostim, Rubex, Rubidomycin hydrochloride, Sandostatin, Sandostatin LAR, Sargramostim, Solu-Cortef, Solu-Medrol, Sorafenib, SPRYCEL, STI-571, Streptozocin, SU11248, Sunitinib, Sutent, Tamoxifen, Tarceva, Targetin, Tasigna, Taxol, Taxotere, Temodar, Temozolomide, Temsirolimus, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Torisel, Tositumomab, Trastuzumab, Treanda, Tretinoin, Trexall, Trisenox, TSPA, TYKERB, VCR, Vectibix, Velban, Velcade, VePesid, Vesanoid, Viadur, Vidaza, Vinblastine, Vinblastine Sulfate, Vincasar Pfs, Vincristine, Vinorelbine, Vinorelbine tartrate, VLB, VM-26, Vorinostat, Votrient, VP-16, Vumon, Xeloda, Zanosar, Zevalin, Zinecard, Zoladcx, Zoledronic acid, Zolinza, Zometa, or combinations of any of the above.

In yet another embodiment, a method of treating cancer by administering an effective amount of compounds V to XIV of present invention is provided. In a preferred embodiment, a method of treating cancer comprising administering an effective amount of compound of formula V or VI is provided. The cancer can be breast, oral, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, or stomach cancer. In a preferred embodiment, the method of treatment of the present invention comprising administering an effective amount of compound of Formula V or VI can be for the treatment of breast and/or prostate cancer.

In an embodiment, a method of inhibition of unregulated cell growth by administering effective amount of the compounds of the present invention is provided.

In a further embodiment, the method of treating cancer by administering compounds of the present invention along with standard therapies or in combination with other drugs available for the treatment of cancer.

Another embodiment of the invention provides for the use of the compounds in the treatment of unregulated cell growth, malaria, dengue.

The foregoing description of the invention has been set merely to illustrate the invention and is not intended to be limiting. Since modifications of the disclosed embodiments incorporating the spirit and substance of the invention may occur to person skilled in the art, the invention should be construed to include everything within the scope of the disclosure. Following are the illustrative and non-limiting examples, including the best mode, for practicing the present invention.

Example 1

Synthetic Scheme for Diphyllin Derivatives

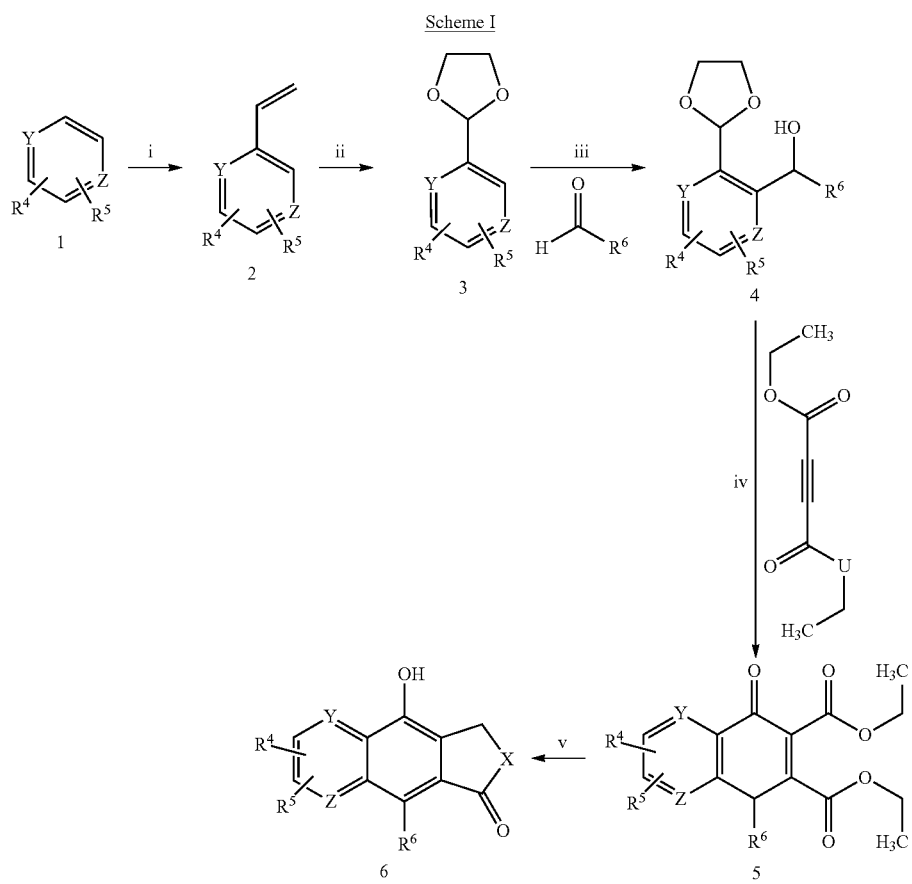

Scheme I):
i) Br$_2$, AcOH at room temperature,
ii) Ethylene glycol, Toluene, p-Toluenesulphonic acid (PTSA), reflux,
iii) n-BuLi, Aldehyde, -78° C.,
iv) Diethylacetylenedicarboxylate (DEADC), methylene dichloride (MDC0, 140°C.,
v) LiAlH$_4$, Tetrahydrofuran (THF).

Procedure:

Synthesis of 2:

Substituted aromatic aldehyde (0.3 mole) was taken in AcOH (200 mL) and Br$_2$ (0.6 mole) was added slowly from addition funnel. The mixture was stirred for 3 h at room temperature and then poured over ice (100 g) and stirred vigorously for 30 min. Slurry was filtered and residue was washed with cold methanol and suction dried under vacuum to obtain pure product 2. Yield, 0.25 mole (85%).

Synthesis of 3:

Compound 2 (0.11 mole) was dispersed in 350 mL of toluene. Ethylene glycol 70 mL and p-Toluenesulphonic acid (0.5 g) were added and mixture was refluxed using Dean-stark assembly for 5 h. Reaction was monitored with TLC (3:7, Ethyl acetate:Hexane). After completion of reaction, saturated NaHCO$_3$ solution was added into the reaction and layers were separated. Toluene layer was washed with brine and dried over anhydrous Na2SO4. Dried toluene layer was evaporated in vacuum to afford pure product 3 (0.11 mole, 97%).

Synthesis of 4:

In an inert reaction assembly charged with nitrogen compound 3 (0.034 mole) was dissolved in Dry THF (150 mL). Mixture was then cooled in a dry ice/acetone bath till −65° C. Through transfer needle 50 ml n-BuLi (1.6M solution in hexane) was added carefully and slowly into the above solution over 30 min. Mixture was stirred for 1 h at −65° C. In a separate addition funnel, the solution of R$^6$—CHO in THF was added drop wise in to the lithiated solution at −65° C. Mixture was stirred for 30 min at same temperature and left at room temperature for 2 h. Mixture was quenched with 10 mL sat. NH$_4$Cl solution and extracted with ethyl acetate (200 mL×2). Ethyl acetate layer was washed with brine solution (100 mL×2), dried over anhydrous Na$_2$SO$_4$ and evaporated in vacuum to isolate crude product. Purification by column chromatography (in silica gel, Ethyl acetate: hexane) gave pure product 4 (0.008 mole, 24%).

Synthesis of 5:

Compound 4 (0.012 mole), acetic acid (6.7 mL), DEADC (0.016 mole) and MDC (100 mL) were taken into the high pressure closed vessel. Mixture was heated at 140° C. for 2 h. Heating stopped and mixture was washed with saturated NaHCO$_3$. MDC layer was dried with anhydrous Na$_2$SO$_4$ and solvents were evaporated in vacuum and crude product was purified by silica gel column chromatography in ethyl acetate:hexane as a mobile phase. Pure product 5 obtained as an off white solid (0.016 mole, 93%).

Synthesis of 6:

Ester 5 (0.0021 mole) was dissolved in dry THF and slowly added into the dispersion of LiAlH$_4$ (0.0042 mole) in THF at 0° C. Mixture was stirred at 0° C. for 2 h and then at room temperature for overnight. Reaction was quenched with saturated NH$_4$Cl and product was extracted with MDC. Crude product was purified by column chromatography to obtain pure product 6 (0.0011 mole).

Synthesis of Glycoside Portion

MDC extract was washed with brine solution (100 mL×2) and 10% aq. CuSO$_4$ solution until original CuSO4 solution color persists. MDC layer was dried over anhydrous Na$_2$SO$_4$ and evaporated in vacuum on rotary evaporator to obtain the syrupy product 7 (0.129 mole, 97%).

Synthesis of 8:

In a clean and dry round bottom flask, with nitrogen inlet, compound 7 (0.129 mole) was dissolved in 200 mL dry MDC. Mixture cooled to 0° C. in an ice bath and 100 mL HBr/AcOH (33% solution) was added drop wise over a period of 30 min. Material stirred for 2 h at 0° C. and quenched with 50 g ice and stirred for 10 min. MDC layer was separated and washed with sat. NaHCO$_3$ (100 mL×3), brine (100 mL) and dried over anhydrous Na$_2$SO$_4$ and

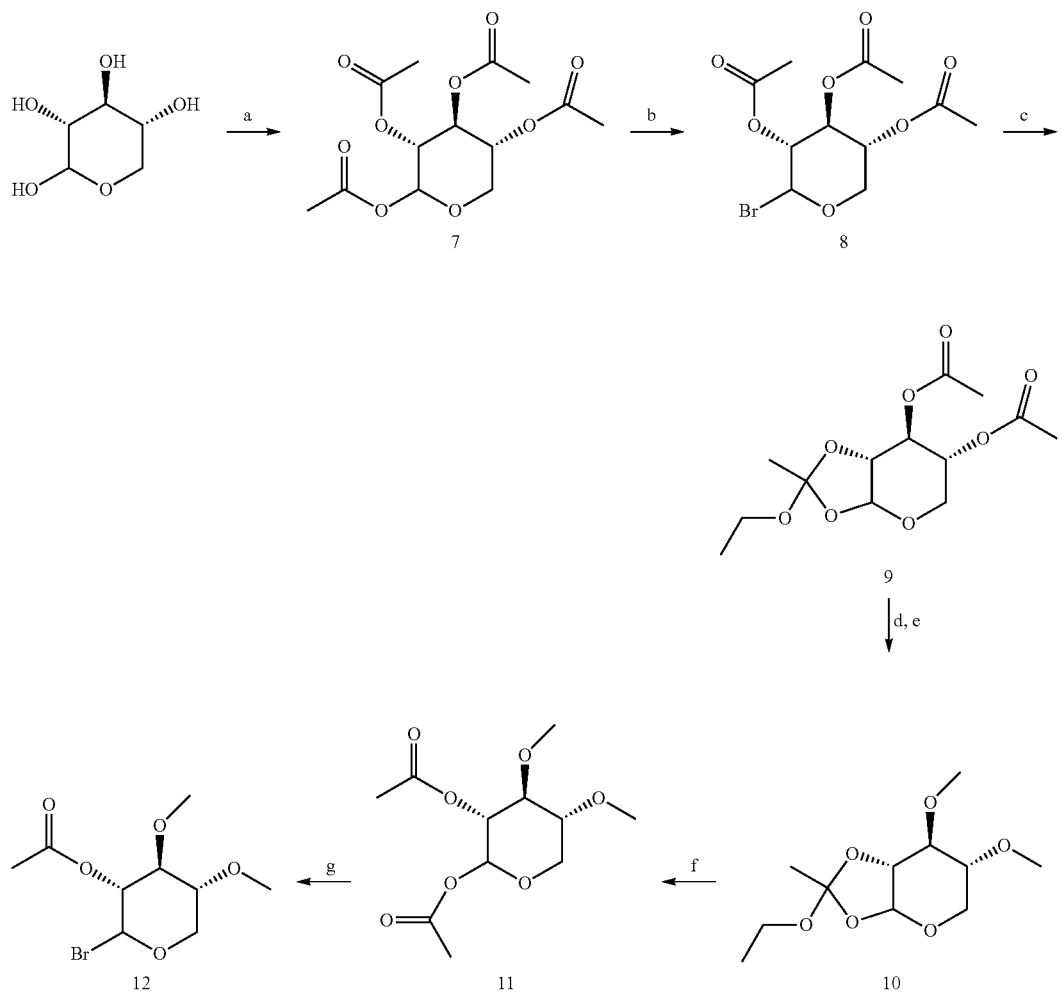

Scheme II, Synthesis of Glycoside: a) Ac—Cl, Pyridine, room temperature, b) HBr/AcOH, 0° C., c) TBAB, 2,6-lutidine, EtOH, d) NaOME, MeOH, e) NaH, DMF, MeI, f) i) AcOH ii) AcCl, Pyridine, g) HBr/AcOH, MDC Synthesis of tetra-acylated d-xylose (7):

D-xylose (0.13 mole) was mixed in MDC (100 mL) and pyridine at room temperature. Mixture cooled to 0° C. and acetyl chloride (0.78 mole) was added slowly under vigorous stirring. Mixture stirred for 1 h at 0° and then at room temperature for 3 h. 50 gm crushed ice was added into the mixture and then 200 mL MDC. Layers were separated and evaporated in vacuum on rotary evaporator to obtain the off-white solid product 8 (0.097 mole, 76%).

Synthesis of 9:

Above compound 8 was taken directly into another round bottom flask containing TBAB (0.040 mole), 2, 6-Lutidine (0.129 mole) and MDC 200 mL and stirred at room temperature for 1 h. After 1 h stirring 6.5 mL EtOH was added slowly and stirring continued for overnight. Solvent removed on rotary evaporator and residue triturated in ethyl acetate (200 mL). Solids were removed by filtration and filtrate was evaporated. Syrupy crude product was purified by silica gel column chromatography in ethyl acetate:hexane to obtain semisolid pure product 9 (0.049 mole, 51%).

Synthesis of 10:

In a single neck round bottom flask compound 9 (0.049 mole) was dissolved in MeOH at room temperature. This mixture cooled between 15-10° C. and NaOMe (600 mg) was added in small portions over 10 min and then stirred for 2 h at room temperature. Thin Later Chromatography (TLC) confirmed the de-acylated product formation. Methanol evaporated on rotary evaporator and residue was dissolved in dry DMF (100 mL). DMF solution chilled to 0° C. and NaH (6 g, 60% suspension) was added portion wise under vigorous stirring under nitrogen atmosphere. Suspension stirred for 15 min at same temperature and methyl iodide was added slowly. Whole suspension was stirred overnight at RT. When TLC confirmed the product formation, 2 mL MeOH and crushed ice, (150 g) were added slowly. Reaction mixture was extracted with ethyl acetate (200 mL×2). Combined ethyl acetate extract was washed with saturated brine solution (50 mL×4) dried over an. Na2SO4 and evaporated on rotary evaporator to obtain oily liquid product 10 (0.048 mole, 98%).

Synthesis of 11:

Compound 10 (0.048 mole) was dissolved in gl. AcOH (50 mL) at 0° C. and stirred for 1 h at room temperature. Acetic acid was evaporated and obtained syrupy residue was dissolved in pyridine (100 mL) and cooled up to 0° C. Ac—Cl was slowly charged into the chilled solution and stirred at room temperature for overnight. Into the reaction mixture 50 mL chilled water was added and extracted with diethyl ether (100 ml×2). Ether extract was washed with sat. CuSO4 solution (50 ml×4) and brine (50 ml) dried over An. Na2SO4 and evaporated on rotary evaporator to isolate product 11 (0.038 mole, 79%)

Synthesis of 12:

In 100 ml dry MDC 11 (0.015 mole) was added and chilled up to 0° C. 10 mL HBr/AcOH (33% solution) was added slowly and mixture was stirred for 1 h at 0° C. Crushed ice (20 g) was added in to the reaction stirred for 5 min. MDC layer was washed with sat. NaHCO3 solution (50 mL×4), brine (50 ml) and dried over Na2SO4 and resulting solution used as such for the synthesis of 13 (see scheme III).

Coupling of Diphyllin Derivative (6) and Glycoside Moiety (12)

Scheme III

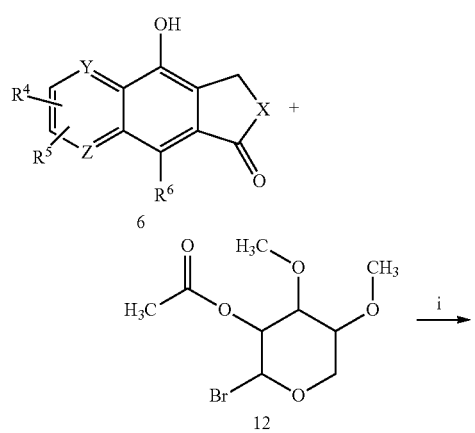

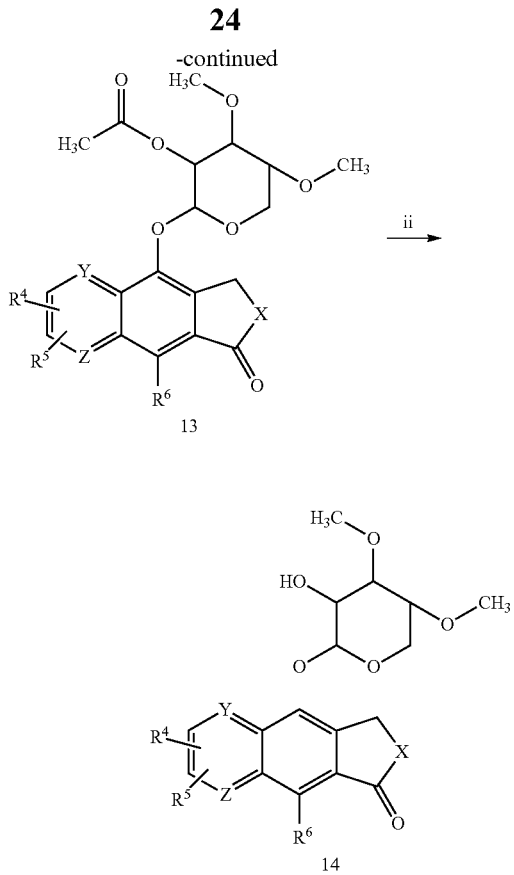

Scheme III:
i) 2N NaOH, TBAB, MDC
ii) MeOH, K2CO3

Synthesis of 13:

Diphyllin derivative (6, 0.0065 mole), TBAB (0.006 mole) and 2N NaOH (25 mL) were mixed in MDC (50 mL) at 0° C. To this, above prepared solution of 13 in MDC was added slowly. Reaction was stirred for 1.5 h and TLC confirmed the product formation. Into the reaction, 25 mL ice cold water was added and stirred vigorously, and then organic phase was separated. MDC layer was washed with 2N NaOH, water, brine and dried over Na2SO4, evaporated on rotary evaporator to obtain crude 13 (2.3 g). Crude product was purified by silica gel column chromatography in Ethyl acetate:Hexane from which pure compound 13 (0.0020 mole) was isolated.

Synthesis of 14:

Condensation product 13 (0.0020 mole) from Glycoside and diphyllin derivative was dissolved in MeOH and chilled the solution till 0°. To this solution anhydrous K2CO3 was added and stirred for 1 h at room temperature. TLC shows complete conversion of 13 into the product 14. Aq. HCl (1N) was added to adjust the neutral pH and MDC was added to extract the product. MDC layer was washed with brine and dried over Na2SO4 and evaporation of MDC on rotary evaporator afforded crude product, which was purified by silica gel column chromatography in Ethyl acetate:Hexane. Pure product 14 (0.00092 mole, 46%) was obtained with >98% purity.

Example 2

Synthesis of Compound of Formula V (Numbered as 14 in Scheme 3)

Step I: Synthesis of 4-(benzo[d][1,3]dioxol-5-yl)naphthalen-1-ol

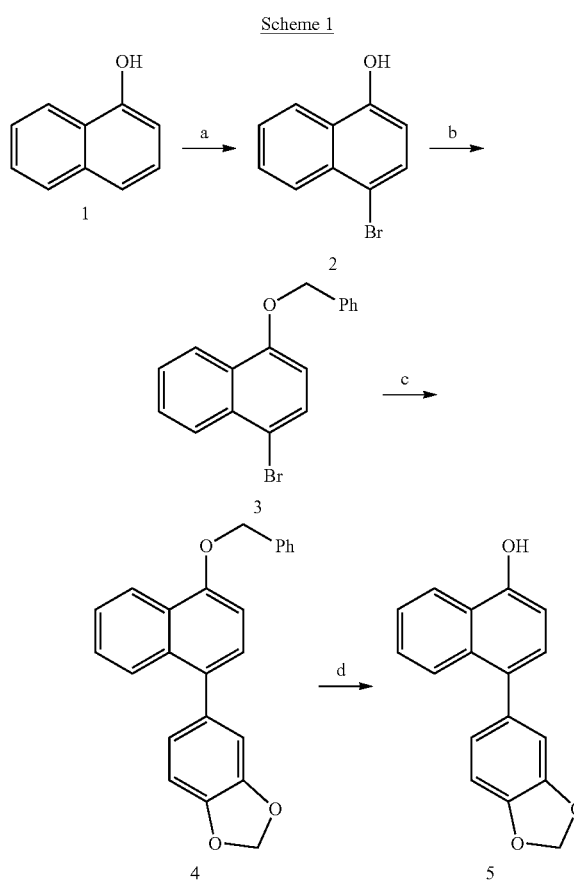

Reagents and conditions: a) NBS (N-Bromosuccinimide), ACN (Acetonitrile, RT, 1.5 hr; b) PhCH$_2$Br, K$_2$CO$_3$, DMF (Dimethylformamide); c) Pd(PPh$_3$)$_4$, 3,4-(methylenedioxy) phenylboronic acid, Na$_2$CO$_3$, DME (Dimethoxyethane); d) 10% Pd/C, EtOH:EtOAc (1:1), 60° C., 60-80 psi.

Experiments

Synthesis of 4-bromonaphthalen-1-ol (2)

To a solution of 1 (5 g, 34.7 mmol) in 180 mL of ACN, NBS (6.18 g, 34.7 mmol); as added over a period of 1 hr. The reaction mixture was stirred at RT for additional 30 min and monitored using TLC. The solvent was evaporated and the residue was partitioned I; n diethyl ether and water. The ethereal layer was dried over anhydrous sodium sulfate and concentrated reduces pressure.

Synthesis of 1-(benzyloxy)-4-bromonaphthalene (3)

To a solution of 2 (7 g, 31.4 mmol) in DMF, K$_2$, CO$_3$ (8.9 g, 64.44 mmol) was added followed by slow-addition of benzyl bromide (3.98 mL, 33.5 mmol). The reaction mixture was stirred at RT and monitored using TLC. After completion, reaction was quenched with brine and the residue was extracted using ethyl acetate and washed with water. The combined organic layer was dried over anhydrous sodium sulfate and concentrated under reduced pressure. The obtained solid was purified by column chromatography (Hex:EtOAc, 98:2).

Synthesis of 5-(4-(benzyloxy)naphthalen-1-yl)benzo[d][1,3]dioxole (4)

To a solution of 3 (1 g, 3.2 mmol) in DME, Pd(PPh$_3$)$_4$ (0.184 g, 5 mol %) was added and stirred for 30 min at RT. The suspension of 3,4-(methylenedioxy)phenylboronic acid (0.635 g, 3.82 mmol) in DME was added to the above solution followed by addition of 2M Na$_2$CO$_3$ (0.676 g) solution. The reaction mixture was refluxed overnight, and monitored using TLC after completion, cooled to RT and solvent was distilled off. The residue was treated with aq. NH$_4$Cl solution and extracted in ethyl acetate. The combined organic layer was dried over anhydrous sodium sulfate and concentrated under reduced pressure. The obtained solid was purified by column chromatography (Hexane:DCM, 95:5)

Synthesis of 4-(benzo[d][1,3]dioxol-5-yl)naphthalen-1-ol (5)

A mixture of 4 (1 g, 2.82 mmol), 10% Pd/C in 50 mL of mixture of EtOH:EtOAc (1:1) was placed in shaker hydrogenation apparatus at 60° C. and 60-80 psi. The reaction was monitored using TLC. After completion, Pd/C was filtered off and the filtrate was evaporated. The obtained solid was purified by column chromatography (DCM:MeOH, 99:1)

Step II: Synthesis of 2-O-Acetyl-3,4-dimethoxy-α-D-bromoxylopyranose (12)

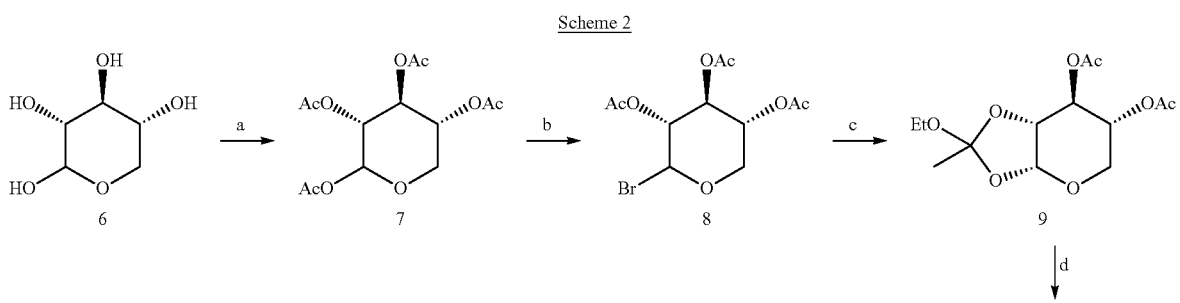

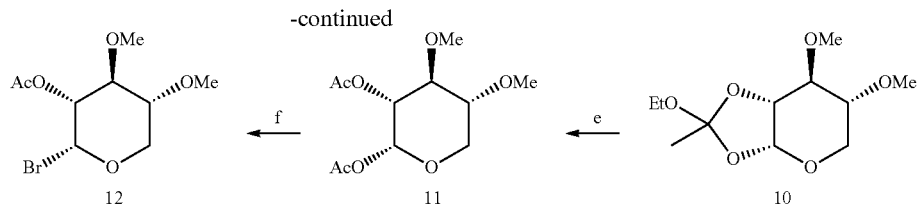

Reagents and conditions: a) Ac₂O, pyridine; b) HBr•AcOH, DCM (Dichloromethane); c) 2,6-lutidine, Bu₄NBr, EtOH, DCM; d) 1. MeONa, MeOH; 2. NaH, MeI, DMF (Dimethylformamide); e) AcOH, Ac₂O, Pyridine; f) HBr•AcOH, DCM Synthesis of Tetra-O-acetyl-D-xylopyranose (7)

To a 500-mL three-neck RBF equipped with guard-tube and stopper, were added 6 (40.0 g. 0.266 mol), pyridine (200 mL) and cooled at 0° C. Acetic anhydride (200 mL) was added dropwise to the above mixture at 0° C. The resulting reaction mixture was stirred at 0° C. for 5 h. After consumption of starting materials, as judged by TLC (5:5, EtOAc: Hexane), reaction mixture was poured into ice water (500 mL) and ether was added (200 mL). Organic layer was separated, and aqueous layer was extracted with ether (2×250 mL). Organic layers were combined and washed with saturated cupric salt solution till free from pyridine. The organic layer was dried over anhydrous sodium sulfate, filtered and concentrated to give sticky solid compound 7.

¹H-NMR (300 MHz, CDCl₃): δ=6.27 (d, 1H, J=3.6 Hz), 5.70 (t, 1H, J=9 Hz), 5.06 (m, 2H), 3.97 (dd, 1H, J=6.0, 1 1.1 Hz), 3.72 (t, 1H, J=1 1.0 Hz), 2.18 (s, 3H), 2.07 (s, 6H), 2.03 (s, 3H).

Synthesis of 2,3,4-Tri-O-acetyl-a-D-bromoxylopyranose (8)

1 L-RBF with guard tube was charged with 7 (25.0 g, 78.54 mol) and dichloromethane (500 mL) and the mixture was cooled to 0° C. in ice bath. To the above cold solution was added hydrogen bromide (33% in acetic acid; 56 mL) with constant stirring during 1 h and reaction mixture was further stirred at room temperature for 1 h. After completion of reaction as judged by TLC (4:6, EtOAc:Hexane), reaction mixture was washed with ice water (1×500 mL), 1% NaHCO₃ solution (1×500 mL), 10% NaHCO₃ solution (2×500 mL) and finally by brine solution (1×500 mL). Organic layer was dried over anhydrous sodium sulfate, filtered and concentrated under reduced pressure to obtained white solid of 8.

¹H-NMR (300 MHz, CDCl₃): δ=6.59 (d, 1H, J=3.9 Hz), 5.60 (t, 1H, J=9.9 Hz), 5.05-5.03 (m, 1H), 4.77 (dd, 1H, J=3.9, 9.6 Hz), 4.07 (dd, 1H, J=6.3, 11.4 Hz), 3.88 (t, 1H, J=11.1 Hz), 2.10 (s, 3H), 2.06 (s, 6H).

Synthesis of 3,4-Di-O-acetyl-1,2-O-(1-ethoxyethylidene)-D-xylopyranose (9)

1. Two necked RBF were charged with 8 (25.0 g, 73.71 mmol), 2,6-lutidine (11.07 mL, 95.82 mmol), tetrabutyl ammonium bromide (9.50 g, 29.48 mmol) and anhydrous dichloromethane (147 mL). To the above mixture was added absolute ethanol (4.7 mL, 81.08 mmol) and reaction mixture was stirred at room temperature under nitrogen atmosphere for overnight. After completion of reaction as judged by TLC (5:5, EtOAc:Hexane), the reaction mixture was concentrated under reduced pressure. The residue was purified by column chromatography over silica gel using EtOAc: Hexane as eluent to afford 9 as a pale yellow colored liquid.

¹H-NMR (300 MHz, CDCl3): δ=5.57 (d, 1H, J=4.2 Hz), 5.24 (t, 1H, J=3.6 Hz), 4.84-4.82 (m, 1H), 4.20 (t, 1H J=1.8 Hz), 3.89 (dd, 1H, J=5.1, 12.3 Hz), 3.71 (dd, III, J=6.9, 12.3 Hz), 3.59 (q, 2H, J=6.9 Hz), 2.10 (s, 311), 2.08 (s, 3H), 1.19 (t, 3H, J=6.9 Hz).

2. In a dried RBF (250 mL) was charged with 9 (10 g, 32.86 mmol) and anhydrous methanol (157 mL) was added. To the above solution was added catalytic amount of sodium methoxide (300 mg) and stirred at room temperature for 1 h. After the completion of reaction as judged by TLC, reaction mixture was concentrated under reduced pressure and residue was dried under high vacuum. The resulting residue was dissolved in anhydrous DMF (100 mL) and cooled to 0° C. in ice-bath. To the above cold solution, sodium hydride (3.94 g, 60% dispersion in oil. 164.3 mmol) was added and resulting suspension was with stirring for 1 h. Methyl iodide (12.4 mL, 197.6 mmol) was added dropwise at 0° C., the reaction mixture was then slowly brought to room temperature during 1 h and further stirred at room temperature for 12 h. After completion of reaction, reaction was quenched by addition of methanol (10 mL), diluted with ethyl acetate (100 mL), washed with water (2×50 mL), brine solution (1×50 mL) and dried over anhydrous sodium sulfate. The inorganic salts were filtered off, filtrate was concentrated under reduced pressure and residue was purified by column chromatography using EtOAc:Hexane (10:90) to afford 10 as a light yellow colored liquid.

¹H-NMR (300 MHz, CDCl3): δ=5.56 (d, 1H, J=4.8 Hz), 4.29-4.26 (m, 1H), 3.89 (dd. 1H J=3.3, 12.1 Hz), 3.82-3.69 (m, 5H), 3.54 (s, 3H), 3.44 (s, 3H), 3.26 (m, 1H), 1.19 (t, 3H, 6.9 Hz).

Synthesis of 1,2-Di-0-acetyl-3,4-dimethoxy-D-xylopyranose (11)

10 (7.5 g, 30.20 mmol) was dissolved in acetic acid (55 mL) and resulting solution was stirred at 0° C. for 1 h. Reaction mixture was concentrated under reduced pressure and the residue was treated with acetic anhydride (26 mL) and pyridine (26 mL). The resulting solution was maintained at room temperature with stirring for overnight. After completion of reaction as judged by TLC (3:7, EtOAc: Hexane), reaction mixture was poured into cold water (100 mL) and extracted with ether (4×100 mL). The organic layers were combined, washed with saturated cupric sulfate solution till the pyridine was removed and then dried over anhydrous sodium sulfate. The inorganic solids were filtered off, filtrate was concentrated under reduced pressure and residue was purified by column chromatography over silica gel using EtOAc:Hexane (20:80) as eluent to afford 11 as a light yellow color.

$^1$H-NMR (300 MHz, CDCl3): δ=5.62 (d, 1H, J=12 Hz), 4.95 (t, 1H J=7.8 Hz), 4.1 1 (m, 1H), 3.57 (s, 3H), 3.48 (s, 3H), 3.39-3.31 (m, 3H), 2.10 (s, 3H), 2.09 (s, 3H).

Synthesis of 2-O-Acetyl-3,4-dimethoxy-α-D-bromoxylopyranose (12)

In a clean and dry 50 mL RBF, 11 (1.0 g, 3.81 nmol) was dissolved in dichloromethane (25 mL) and cooled to 0° C. in ice bath. To the above cooled solution was added hydrogen bromide in AcOH (33% solution; 2.5 mL) with constant stirring for 1 h and further stirred at room temperature for another 1 h. After completion of reaction as judged by TLC (3:7, EtOAc:Hexane), reaction mixture was diluted with dichloromethane (50 ML), washed with ice water (50 mL) followed by saturated NaHCO$_3$ solution (50 mL) and finally with brine solution (50 mL). Organic layer was dried over anhydrous sodium sulfate, filtered and concentrated to give yellow colored liquid 12 as a product.

$^1$H-NMR (300 MHz, CDCl3): δ=6.56 (d, 1H, J=3.9 Hz), 4.56 (dd, 1H, J=3.9, 9.6 Hz), 4.00 (dd, 1H, J=6.3, 1 1.7. Hz), 3.72 (m, 1H), 3.56 (s, 3H), 3.54 (s, 3H), 3.38 (m, 2H), 2.13 (s, 3H).

Step III: Synthesis of (3R,4R,5R)-2-(4-(benzo[d][1,3]dioxol-5-yl)napthalen-1-yloxy)-4,5-dimethoxytetrahydro-2H-pyran-3-ol (14)

Scheme 3

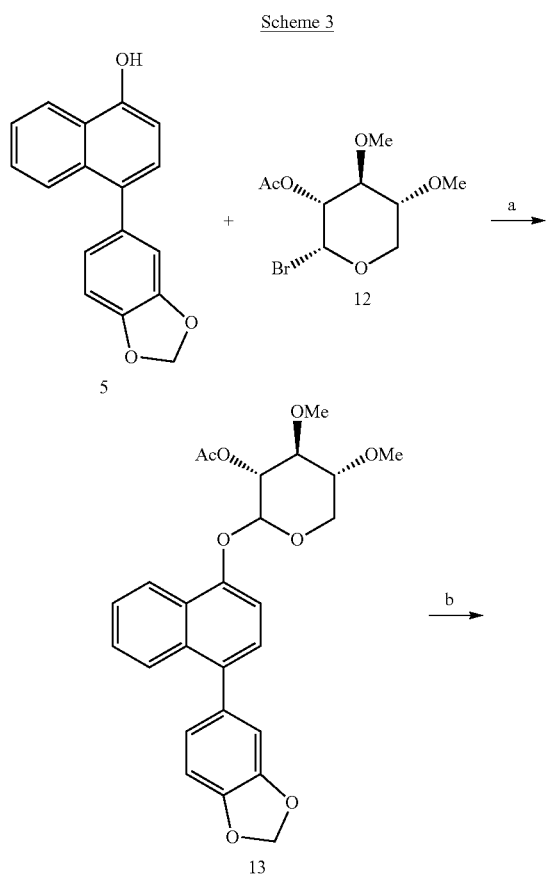

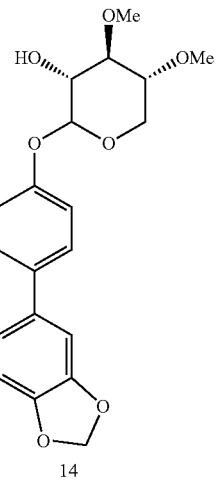

Reagents and conditions: a) Bu$_4$NBr, 2M NaOH, DCM (Dichloromethane), RT; b) K$_2$CO$_3$ MeOH, RT. b) K$_2$CO$_3$ MeOH, RT.

Synthesis of (3R,4R,5R)-2-(4-(benzo[d][1,3]dioxol-5-yl)naphthalen-1-yloxy)-4,5-dimethoxy-tetrahydro-2H-pyran-3-yl acetate (13)

To a 50 mL RBF, 5 (0.208 g, 0.788 mmol), 12 (0.446 g, 1.576 mmol) and tetrabutyl ammonium bromide (0.254 g, 0.788 mmol) were taken in dichloromethane (20 mL) with stirring. To this suspension was added 2M NaOH (3 mL) solution and stirring was continued for 2 h at room temperature. After the completion of reaction as judged by TLC (1:9, EtOAc:DCM), the reaction mixture was extracted with dichloromethane (4×20 mL). The combined organic layer was washed with 10% NaOH solution (3×15 mL) followed by water (2×10 mL) and dried over anhydrous sodium sulfate. Inorganic salts were filtered off; filtrate was concentrated under reduced pressure and crude mass which was purified by column chromatography using EtOAc:dichloromethane (4:96) as eluent to obtain 13 as white solid.

Synthesis of (3R,4R,5R)-2-(4-(benzo[d][1,3]dioxol-5-yl)naphthalen-1-yloxy)-4,5-dimethoxy-tetrahydro-2H-pyran-3-ol (14)

To a solution of 13 (0.160 g, 0.343 mmol) in methanol (7.5 mL) was added solid anhydrous K$_2$CO$_3$ (0.0925 g 0.675 mmol) and reaction mixture was stirred at room temperature for 30 min. After completion of reaction as judged by TLC (5:5, EtOAc:Hexane), methanol was removed under reduced pressure, water was added and extracted with CH$_2$Cl$_2$ (2×25 mL). Organic layer was dried over anhydrous sodium sulfate, filtered and concentrated to get 14 as white fluffy solid.

% Purity: 99%; LC-MS (ESI) m/z: 425 [M+H]$^+$ $^1$H-NMR (400 MHz, CDCl3): δ=8.35 (d, 1H, J=8 Hz), 7.89 (d, 1H, J=8 Hz), 7.51-7.46 (m, 2H), 7.31 (d, 1H, J=7.6 Hz), 7.14 (d, 1H, J=8.0 Hz), 6.94 (m, 3H), 6.03 (s, 2H), 5.52 (d, 1H, J=3.6 Hz), 4.18 (dd, 1H, J=6.3, 1 1.7. Hz), 4.05 (m, 1H), 3.69 (s, 3H), 3.61 (m, 2H), 3.51 (s, 3H), 3.45 (m, 1H), 3.38 (m, 1H).

Example 3

Synthesis of Compound of Formula VI (Numbered as 26 in Scheme 4)

Synthesis of diethyl 1-(benzo[d][1,3]dioxol-5-yl)-4-((3R,4R,5R)-3-hydroxy-4,5-dimethoxy-tetrahydro-2H-pyran-2-yloxy)-6,7-dimethoxynaphthalene-2,3-dicarboxylate (26)

Scheme 4

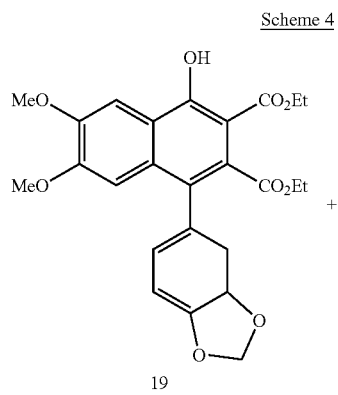

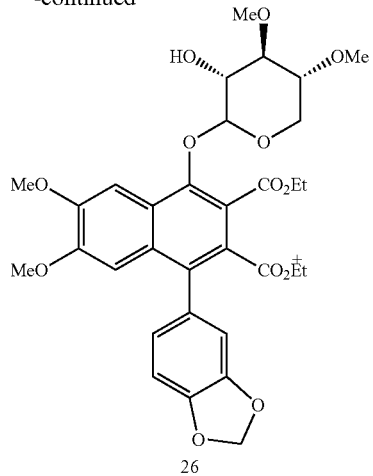

Reagents and conditions: a) Bu₄NBr, 2M NaOH, DCM (Dichloromethane), RT; b) K₂CO₃, MeOH, RT.

Experimental:

Cleyacetate (25):

To a 50-mL round bottom flask, diethyl 1-(benzo[d][1,3]dioxol-5-yl)-4-hydroxy-6,7-dimethoxynaphthalene-2,3-dicarboxylate (19; 0.30 g, 0.638 mmole), 2-O-Acetyl-3,4-dimethoxy-α-D-bromoxylopyranose (12, 0.446 g, 1.276 mmole) and tetrabutyl ammonium bromide (0.254 g, 0.638 mmole) were taken in dichloromethane (20 mL) with stirring. To this suspension was added 2M NaOH (3 mL) solution and stirring was continued for 2 h at room temperature. After the completion of reaction as judged by TLC (1:9, EtOAc:DCM), the reaction mixture was extracted with dichloromethane (4×20 mL). The combined organic layer was washed with 10% NaOH solution (3×15 mL) followed by water (2×10 mL) and dried over anhydrous sodium sulfate. Inorganic salts were filtered off filtrate was concentrated under reduced pressure and crude mass which was purified by column chromatography 4 using EtOAc:dichloromethane (04:96) as eluent to obtain Cleyacetate (25) as an oil.

Synthesis of diethyl 1-(benzo[d][1,3]dioxol-5-yl)-4-((3R,4R,5R)-3-hydroxy-4,5-dimethoxy-tetrahydro-2H-pyran-2-yloxy)-6,7-dimethoxynaphthalene-2,3-dicarboxylate (26)

To a solution of 25 (0.20 g, 0.298 mmole) in methanol (7.5 mL) was added solid anhydrous K₂CO₃ (0.0825 g 0.597 mmol) and reaction mixture was stirred at room temperature for 30 min. After completion of reaction as judged by TLC (5:5, EtOAc:Hexane), methanol was removed under reduced pressure, water was added and extracted with CH₂Cl₂ (2×25 mL). Organic layer was dried over anhydrous sodium sulfate, filtered and concentrated to get 26 as off white fluffy solid.

Yield: 179 mg (96%); % Purity: 99%; LC-MS (ESI) m/z: 629 [M+H]⁺

¹HNMR (CDCl3, 400 MHz): □=8.17 (s, 1H), 7.05 (d, 1H, J=1.5 Hz), 6.94 (dd, 1H, J=1.2, 7.8 Hz), 6.98 (d, 2H, J=1.6 Hz), 6.92 (d, 1H, J=1.2 Hz), 6.80 (d, 1H, J=8 Hz), 6.12 (s, 2H), 5.73 (m, 1H), 5.50 (q, 2H, J=3.6 Hz), 5.00 (d, 1H, J=5.2 Hz), 4.80 (t, 1H, J=6.8 Hz, 4.72 (d, 1H, J=4.4 Hz) 3.94 (s, 3H), 3.86-3.81 (m, 31H), 3.70 (s, 3H), 3.51 (m, 1H), 3.46 (m, 1H).

Example 4

Synthesis of Compound of Formula VII (Numbered as 21 in Scheme 6) and Compound of Formula VIII (Referred as 22 in Scheme 7)

Step I: Synthesis of Diphyllin

Scheme 5

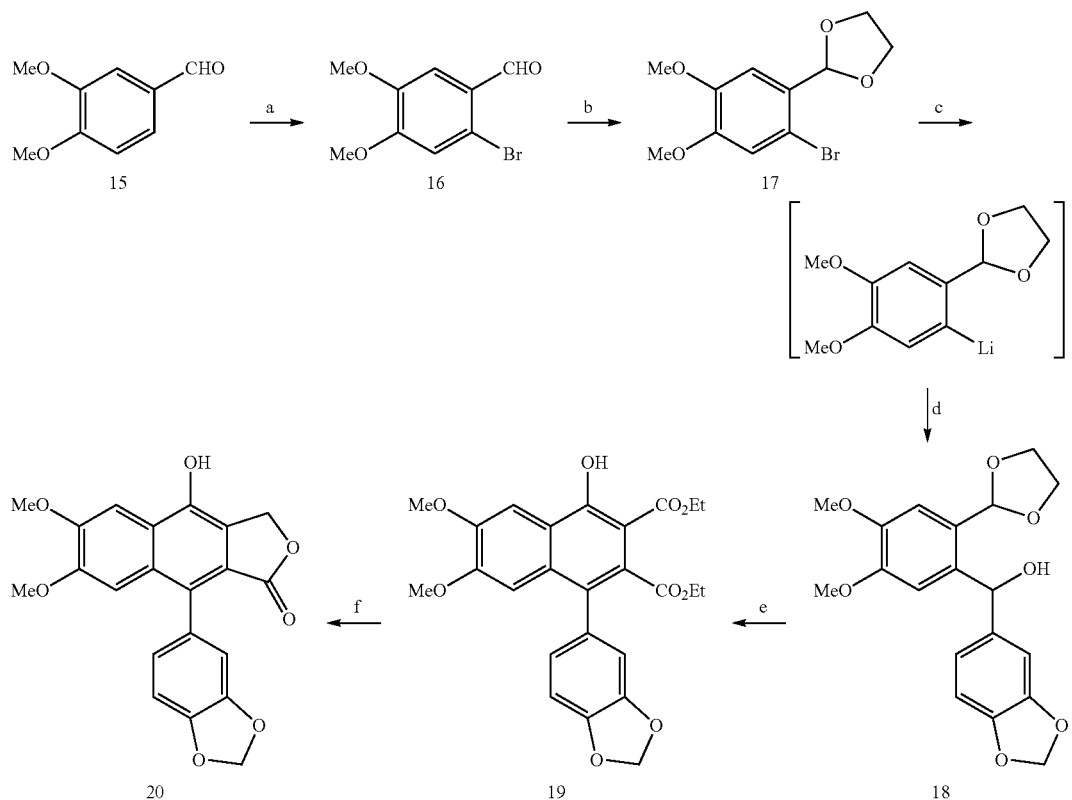

Reagents and conditions: a) Br2, AcOH, 3 h; b) ethylene glycol, p-TSA (toluene sulfonic acid), toluene; c) n-BuLi, THF (tetrahydrofuran); d) piperinol, THF; e) diethyl acetylinedicarboxylate, AcOH, DCM; f) LiAlH$_4$, THF.

Experimental:

Synthesis of 2-Bromo-4,5-dimethoxybenzaldehyde (16)

Three necked RBF (500 mL) equipped with dropping funnel, magnetic stirrer, and stopper was charged with veratraldehyde or 4,5-dimethoxybenzaldehyde (15, 15 g, 0.090 mol) and acetic acid (210 mL). To this solution was added bromine (9.67 mL) in acetic acid (60 mL) dropwise with constant stirring over half an hour and stirring was further continued for 3 h at room temperature. During this time all the starting materials was consumed as confirmed by TLC (3:7, EtOAc:Hexane). Water (250 mL) was added to the reaction mixture and cooled to 0° C. The precipitated solid was filtered off, washed with cold water and dried under vacuum to get a white solid 16.

$^1$H-NMR (CDCl3, 300 MHz): δ=10.19 (s, 1H), 7.43 (s, 1H), 7.07 (s, 1H), 3.97 (s, 3H). 3.93 (s, 3H).

Synthesis of 2-(2-Bromo-4,5-dimethoxyphenyl)-1,3-dioxolane (17)

Three necked RBF (250 mL) was equipped with Dean-Stark apparatus and reflux condenser, was charged with 16 (19.0 g, 0.07 mol), toluene (200 mL), ethylene glycol (1.8 mL, 0.21 mol) and catalytic amount of p-toluene sulphonic acid. The reaction flask was immersed in oil bath and heated (90-95° C.) under reflux for 9 h (till all the water removed). After completion of reaction as judged by TLC (2:8, EtOAc: Hexane), reaction mixture was allowed to cool to room temperature, neutralized by sodium bicarbonate solution and extracted with ethyl acetate (3×100 mL). All the organic layers were combined, dried over anhydrous sodium sulfate, filtered and concentrated under reduced pressure. The crude mass was purified by column chromatography over silica gel using ethyl acetate (5-10%) in hexane as eluent to afford 17 as a white solid.

$^1$H-NMR (300 MHz, CDCl3): δ=7.1 1 (s, 1H), 7.01 (s, 1H), 5.99 (s, 1H), 4.18 (t, 2H, J=6.9 Hz), 4.08 (t, 2H, J=6.9 Hz), 3.89 (s, 3H), 3.88 (s, 3H).

Synthesis of (2-(1,3-Dioxolan-2-yl)-4,5-dimethoxyphenyl)(benzo[d][1,3]dioxol-5-yl)-meth-anol (18)

To a flame dried three necked RBF (100 mL) were added 16 (1.0 g, 0.0034 mole) and anhydrous THF (25 mL) under nitrogen atmosphere. The flask was cooling to −78° C. in dry ice-acetone bath, n-BuLi (5.3 mL, 0.005 mol) was added dropwise with stirring at −78° C. and stirred for 15 min. A separate flame dried flask was charged with piperonal (0.517 g, 0.0034 mol) and dry THF (6 mL). The piperonal solution was cannulated to the reaction mixture during 30 min and after the addition; reaction mixture was slowly warmed to room temperature and further stirred for 2.5 h. After the consumption of all bromo compound, as confirmed by TLC (5:5, EtOAc:Hexane), reaction mixture was quenched by the addition of saturated ammonium chloride solution and extracted with ethyl acetate (3×20 mL). All the organic layers were combined, dried over anhydrous sodium sulfate, filtered and concentrated. The crude product was purified by titration with heptane and 18 is sufficiently pure to proceed to next step.

$^1$H-NMR (300 MHz, CDCl3): δ=7.14 (s, 1H), 6.90-6.78 (m, 4H), 6.11 (s, 1H), 5.96 (s, 2H), 5.90 (s, 1H), 4.19 (t, 2H, J=6.6 Hz), 4.16 (t, 2H, J=6.8 Hz), 4.02 (s, 3H), 3.81 (s, 3H), 3.17 (s, 1H). 13C-NMR (300 MHz, CDCl3): δ=149.42, 148.11, 147.57, 146.58, 136.95, 135.43, 126.83, 121.04, 119.69, 1 1 1.48, 109.50, 107.92, 107.26, 101.65, 100.93, 71.34, 65.05, 55.94, 55.89.

Synthesis of Diethyl 1-(3',4'-methylenedioxypheny)-4-hydroxy-6,7-dimethoxy-naphthalene-2,3-dicarboxylate (19)

Sealed tube was charged with 18 (0.30 g, 0.833 mmol), diethyl acetylinedicarboxylate (0.141 g, 0.833 mol), dichloromethane (0.4 mL) and glacial acetic acid (0.242 mL) and mixture was heated at 140° C. for 1 h. After completion of reaction as judged by TLC (5:5, EtOAc:Hexane), reaction mixture was cooled to room temperature, diluted with dichloromethane (10 mL), washed with 5% sodium bicarbonate solution (3×10 mL), organic layer was dried over anhydrous sodium sulfate, filtered and concentrated. The crude reaction mass was purified by flash column chromatography over silica gel using EtOAc:Hexane (15:85) to afford 19 as white solid.

$^1$H-NMR (300 MHz, CDCl3): δ=7.73 (s, 1H), 6.89 (d, 1H, J=7.8 Hz), 6.81-6.75 (m, 3H), 6.05 (d, 2H, J=14.4 Hz), 4.44 (q, 2H. J=7.2 Hz), 4.07 (q, 2H, J=6.9 Hz), 4.05 (s, 3H), 3.77 (s, 3H), 1.38 (t, 3H, J=7.2 Hz), 1.08 (t, 3H, J=6.9 Hz). 13C-NMR (300 MHz, CDCl3): δ=170.30, 168.74, 159.62, 152.37, 149.68, 147.22, 147.06, 132.21, 130.60, 128.99, 127.48, 124.37, 119.81, 1 1 1.42, 107.97, 105.73, 102.76, 101.09, 61.95, 60.81, 56.08, 55.79, 13.87, 13.82.

Synthesis of 9-(3',4'-Methylenedioxyphenyl)-4-hydroxy-6,7-dimethoxynaphtho[2,3-c]furan-l(3H)-one (20)

Two necked RBF (25 mL) was charged with LAH (0.032 g, 0.852 mmol) and anhydrous THF (4 mL) and the mixture was cooled to 0° C. with stirring. To this suspension, a solution of 19 (0.200 g, 0.426 mmol) in THF (4 mL) was added dropwise at 0° C. and stirring was continued for 2 h at same temperature. After completion of reaction as judged by TLC (1:9, MeOH:DCM), reaction mixture was quenched with saturated sodium sulfate solution and extracted with t-butanol (4×20 mL). Organic layer was dried over anhydrous sodium sulfate, filtered and concentrated under reduced pressure. The crude residue was purified by flash column chromatography over silica gel to give yellow solid 20.

$^1$H-NMR (300 MHz, DMSOd6) δ=10.39 (s, 1H), 7.61 (s, 1H), 7.00 (d, 1H, J=8.1 Hz), 6.94 (s, 1H), 6.85 (d, 1H, J=1.5 Hz), 6.75 (dd, 1H J=1.5, 8.4 Hz), 6.10 (s, 2H), 5.35 (s, 2H), 3.93 (s, 3H), 3.64 (s, 3H). 13C-NMR (300 MHz, DMSOd6): δ=169.81, 150.66, 149.89, 147.01, 146.76, 145.05, 129.71, 129.65, 128.95, 123.94, 123.45, 121.85, 1 18.86, 11 1.22, 108.02, 105.63, 101.19, 100.92, 66.71, 55.78, 55.29.

LC-MS (ESI) m/z: 381 [M+H]+

Step II: Synthesis of Diphyllin Esters

General Procedure for Ester Derivatives:

To a 50 mL RBF, 20 (1 eq.), corresponding carboxylic acid (1 eq.), DMAP (10 eq.) in 20 mL of DCM was cooled (at 0° C.). The reaction mixture was stirred for 30 min. and then DCC (1.1 eq. dissolved in cold DCM) was added dropwise.

The reaction was stirred at RT overnight. The reaction as monitored using TLC (2:98, MeOH:DCM). After completion, the solid obtained was filtered off and the filtrate was diluted with DCM and washed with water twice. The combined organic layer was dried over Na$_2$SO$_4$ and concentrated under reduced pressure. The obtained solid s purified by column chromatography (DCM:MeOH, 98:2).

Synthesis of 9-(benzo[d][1,3]dioxol-5-yl)-6,7-dimethoxy-1-oxo-1,3-dihydronaphtho[2,3-c] furan-4-yl 1-methyl-1H-pyrrole-2-carboxylate (21)

Scheme 6

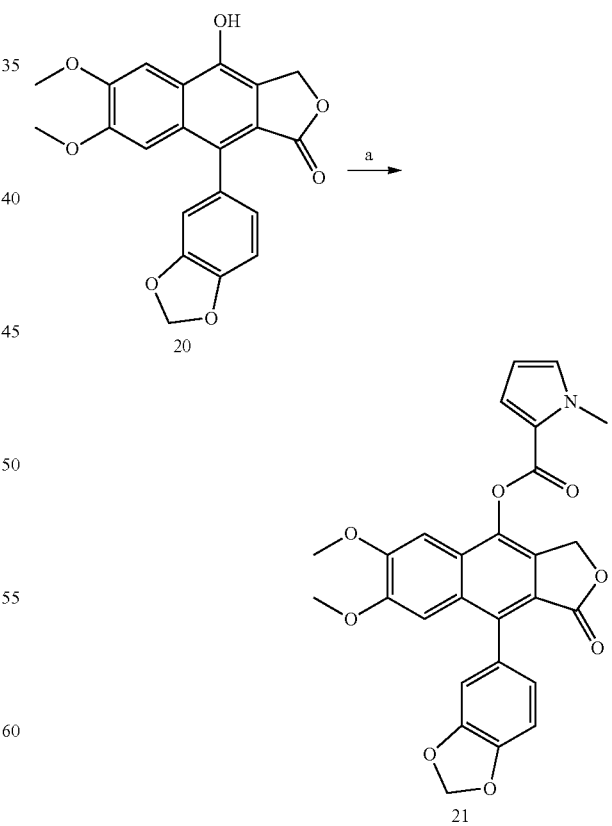

Reagents and conditions: a) 1-methyl-2-pyrrolecarboxylic acid, DMAP (4-Dimethylaminopyridine), DCC (N,N'-Dicyclohexylcarbodiimide), DCM (Dichloromethane), 0° C. overnight.

Synthesis of 9-(benzo[d][1,3]dioxol-5-yl)-6,7-dimethoxy-1-oxo-1,3-dihydronaphtho[2,3-c]furan-4-yl 1-methyl-1H-pyrrole-2-carboxylate (21)

To a 50 mL RBF, Diphyllin (200 mg, 5.26 mmol), 1-methyl-1H-pyrrole-2-carboxylic acid (65.78 mg, 5.26 mmol), DMAP (642 mg, 52.6 mmol) in 1.0 mL of DCM was cooled (at 0° C.). The reaction mixture was stirred for 30 min. and then DCC (119 mg, 5.78 mmol dissolved in cold DCM) was added dropwise. The reaction was stirred at RT overnight. The reaction was monitored using TLC (98:2, DCM:MeOH). After completion, the solid obtained was filtered off and the filtrate was diluted with DCM and washed with water twice. The combined organic layer was dried over Na2SO4 and concentrated under reduced pressure. The obtained solid was purified by column chromatography (DCM:MeOH, 98:2).

% Purity: 99%; LC-MS (ESI) m/z: 488 [M+H]$^+$ $^1$H-NMR (400 MHz, CDCl3): δ=7.41-7.39 (m, 1H), 7.32 (s, 1H), 7.26 (s, 1H), 7.13 (s, 1H), 6.99 (m, 2H), 6.86 (m, 2H), 6.30 (m, 1H), 6.10 (d, 2H, J=17.6 Hz), 5.32 (s, 2H), 4.01 (s, 3H), 3.98 (s, 3H), 3.81 (s, 3H).

Synthesis of 9-(benzo[d][1,3]dioxol-5-yl)-6,7-dimethoxy-1-oxo-1,3-dihydronaphtho[2,3-c]furan-4-yl 2-cyclopentyl-2-phenylacetate (22)

Scheme 7

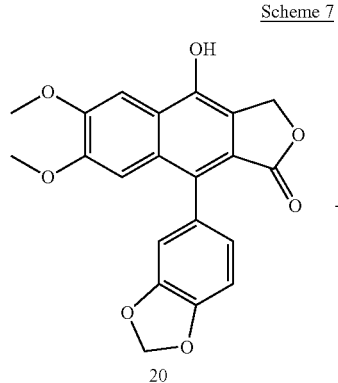

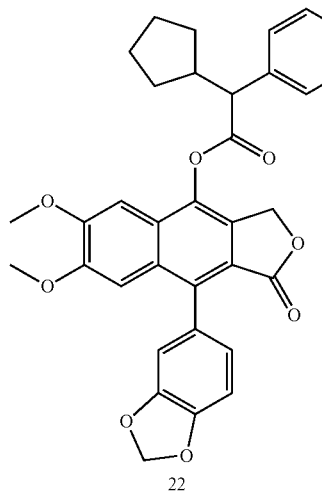

Reagents and conditions: a) α-phenylcyclopentaneacetic acid, DMAP (4-Dimethylaminopyridine), DCC (N,N'-Dicyclohexylcarbodiimide), DCM (Dichloromethane), 0° C. overnight.

Synthesis of 9-(benzo[d][1,3]dioxol-5-yl)-6,7-dimethoxy-1-oxo-1,3-dihydronaphtho[2,3-c]furan-4-yl 2-cyclopentyl-2-phenylacetate (22)

To a 50 mL RBF, Diphyllin (200 mg, 5.26 mmol), 2-cyclopentyl-2-phenylacetic acid (107 mg, 5.26 mmol), DMAP (642 mg, 52.6 mmol) in 10 mL of DCM was cooled (at 0° C.). The reaction mixture was stirred for 30 min. and then DCC (119 mg, 5.78 mmol dissolved in cold DCM) was added dropwise. The reaction was stirred at RT overnight. The reaction was monitored using TLC (98:2, DCM:MeOH). After completion, the solid obtained was filtered off and the filtrate was diluted with DCM and washed with water twice. The combined organic layer was dried over Na2SO4 and concentrated under reduced pressure. The obtained solid was purified by column chromatography (DCM:MeOH, 98:2).

% Purity: 99%; LC-MS (ESI) m/z: 567 [M+H]$^+$ $^1$H-NMR (400 MHz, CDCl3): δ=7.55-7.53 (m, 2H), 7.42 (m, 2H), 7.35 (m, 2H), 7.05 (s, 1H), 6.96 (m, 1H), 6.80 (m, 2H), 6.66 (s, 1H), 6.06 (d, 1H, J=1.6 Hz), 6.04 (d, 1H, J=1.2 Hz), 5.07 (s, 2H), 3.76 (s, 3H), 3.52 (s, 3H), 2.89-2.79 (m, 1H), 2.20-2.14 (m, 1H), 1.78 (m, 1H), 1.71 (m, 4H), 1.65 (m, 4H).

Example 5

Synthesis of Compound of Formula IX (Numbered as 23 in Scheme 8)

Scheme 8

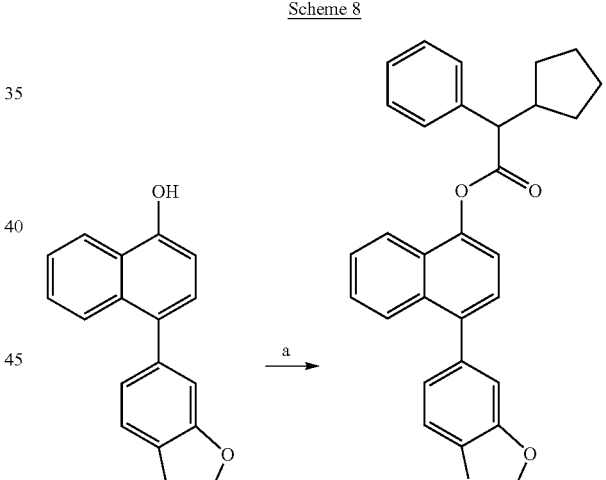

Reagents and conditions: a) α-phenylcyclopentaneacetic acid, DMAP (4-Dimethylaminopyridine), DCC (N,N'-Dicyclohexylcarbodiimide), DCM (Dichloromethane), 0° C. overnight.

Experimental:

Synthesis of 1-(benzo[d][1,3]dioxol-5-yl)naphthalen-4-yl 2-cyclopentyl-2-phenylacetate(23)

To a 50 mL RBF, 5 (200 mg, 7.5 mmol), 1-methyl-1H-pyrrole-2-carboxylic acid (93.6 mg, 7.5 mmol), DMAP (924 mg, 75 mmol) in 10 mL of DCM was cooled (at 0° C.). The reaction mixture was stirred for 30 min. and then DCC (171.6 mg, 8.33 mmol, dissolved in cold DCM) was added dropwise. The reaction was stirred at RT overnight. The reaction was monitored using TLC (98:2, DCM:MeOH).

After completion, the solid obtained was filtered off and the filtrate was diluted with DCM and washed with water twice. The combined organic layer was dried over Na$_2$SO$_4$ and concentrated under reduced pressure.

The obtained solid was purified by column chromatography (DCM:MeOH, 98:2).

% Purity: 99%; LC-MS (ESI) m/z: 451 [M+H]$^+$ $^1$H NMR (400 MHz, CDCl3) δ: 7.91-7.83 (m, 1H), 7.53 (d, J=7.0 Hz, 3H), 7.48 (d, J=7.4 Hz, 1H), 7.46-7.38 (m, 6H), 7.33 (d, J=7.7 Hz, 1H), 7.15 (d, J=7.7 Hz, 1H), 6.91 (dd, J=2.3, 6.7 Hz, 3H), 6.04 (s, 2H), 3.74 (d, J=11.2 Hz, 1H), 2.81 (d, J=9.4 Hz, 1H), 1.92 (d, J=9.9 Hz, 1H), 1.81-1.65 (m, 1H), 1.63-1.47 (m, 1H), 1.29 (d, J=25.2 Hz, 3H).

Example 6

Synthesis of Compound of Formula X (Numbered as 24 in Scheme 9)

Synthesis 1-(benzo[d][1,3]dioxol-5-yl)naphthalen-4-yl 1-methyl-1H-pyrrole-2-carboxylate (24)

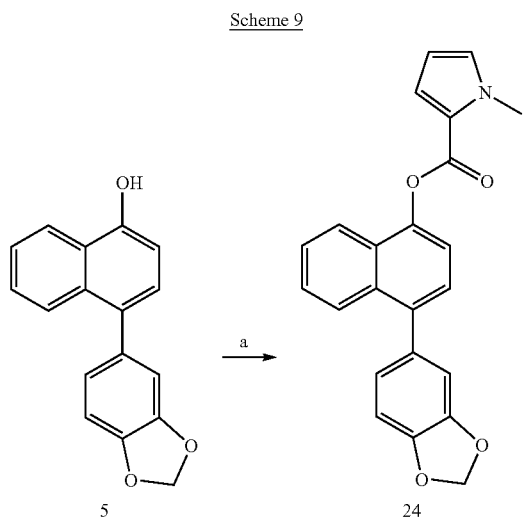

Scheme 9

Reagents and condtions: a) 1-methyl-2-pyrrolecarboxylic acid, DMAP, DCC, DCM, 0° C. overnight.

Experimental:

Synthesis 1-(benzo[d][1,3]dioxol-5-yl)naphthalen-4-yl 1-methyl-1H-pyrrole-2-carboxylate (24)

To a 50 mL RBF, 5 (200 mg, 7.5 mmol), 2-cyclopentyl-2-phenylacetic acid (154.5 mg, 7.5 mmol), DMAP (924 mg, 75 mmol) in 10 mL of DCM was cooled (at 0° C.). The reaction mixture was stirred for 30 min. and then DCC (171.6 mg, 8.33 mmol, dissolved in cold DCM) was added dropwise. The reaction was stirred at RT overnight. The reaction was monitored using TLC (98:2, DCM:MeOH). After completion, the solid obtained was filtered off and the filtrate was diluted with DCM and washed with water twice. The combined organic layer was dried over Na$_2$SO$_4$ and concentrated under reduced pressure. The obtained solid was purified by column chromatography (DCM:MeOH, 98:2).

$^1$H NMR (400 MHz, CDCl$_3$) δ: 8.08-8.00 (m, 1H), 7.98-7.90 (in, 1H), 7.55-7.42 (m, 2H), 7.46-7.37 (m, 2H), 7.35 (d, J=7.7 Hz, 1H), 7.01-6.90 (m, 4H), 6.29 (dd, J=2.5, 4.0 Hz, 1H), 6.05 (s, 2H), 4.00 (s, 3H).

% Purity: 99%; LC-MS (ESI) m/z: 372 [M+H]$^+$

Example 7

Synthesis of Compound of Formula XI (Numbered as 31 in Scheme 11)

Synthesis of (3S,4R,5R)-2-(1-(benzo[d][1,3]dioxol-5-yl)naphthalen-4-yloxy)-tetrahydro-2H-pyran-3,4,5-triol (31)

Scheme 10

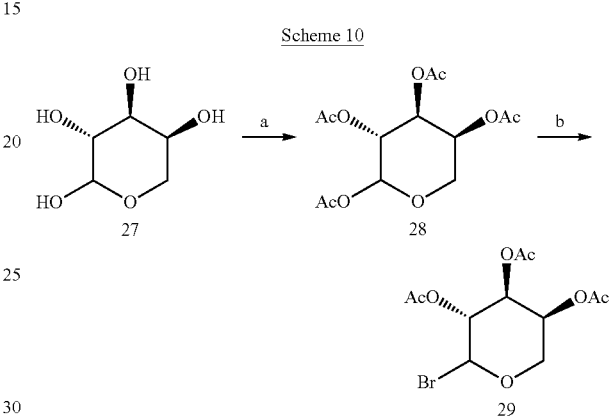

Reagents and conditions: a) Ac$_2$O, pyridine; b) HBr•AcOH, DCM (Dichloromethane);

Experimental:

Synthesis of Tetra-O-acetyl-L-Arabinose (28)

To a 500-mL three-neck RBF equipped with guard-tube and stopper, were added 27 (40.0 g, 0.266 mol), pyridine (200 mL) and cooled it at 0° C. Acetic anhydride (200 mL) was added dropwise to the above mixture at 0° C. The resulting reaction mixture was stirred at 0° C. for 5 h. After consumption of starting materials, as judged by TLC (5:5, EtOAc:Hexane), reaction mixture was poured into ice water (500 mL) and ether was added (200 mL). Organic layer was separated and aqueous layer was extracted with ether (2×250 mL). Organic layers were combined and washed with saturated cupric salt solution till free from pyridine. The organic layer was dried over anhydrous sodium sulfate, filtered and concentrated to give sticky solid compound 28.

$^1$H-NMR (300 MHz, CDCl3): δ=6.27 (d, III, J=3.6 Hz), 5.70 (t, 1H, J=9 Hz), 5.06 (m, 2H), 3.97 (dd, 1H, J=6.0, 1 1.1 Hz), 3.72 (t, 1H, J=1 1.0 Hz), 2.18 (s, 3H), 2.07 (s, 6H), 2.03 (s, 3H).

Synthesis of 2 Bromo 3,4,5-Tri-O-acetyl-a-L-Arabinose (29)

1 L-RBF with guard tube was charged 28 (20.0 g, 62.9 mmol) and dichloromethane (500 mL) and mixture was cooled to 0° C. in ice bath. To the above cold solution was added hydrogen bromide (33% in acetic acid; 46 mL) with constant stirring during 1 h and reaction mixture was further stirred at room temperature for 1 h. After completion of reaction as judged by TLC (4:6, EtOAc:Hexane), reaction mixture was washed with ice water (1×500 mL), 1% NaHCO$_3$ solution (1×500 mL), 10% NaHCO$_3$ solution (2×500 mL) and finally by brine solution (1×500 mL). Organic layer was dried over anhydrous sodium sulfate, filtered and concentrated under reduced pressure to obtained white solid of 29.

¹H-NMR (300 MHz, CDCl₃): δ=6.59 (d, 1H, J=3.9 Hz), 5.60 (t, 1H, J=9.9 Hz), 5.05-5.03 (m, 1H), 4.77 (dd, 1H, J=3.9, 9.6 Hz), 4.07 (dd, 1H, J=6.3, 11.4 Hz), 3.88 (t, 1H, J=11.1 Hz), 2.10 (s, 3H), 2.06 (s, 6H).

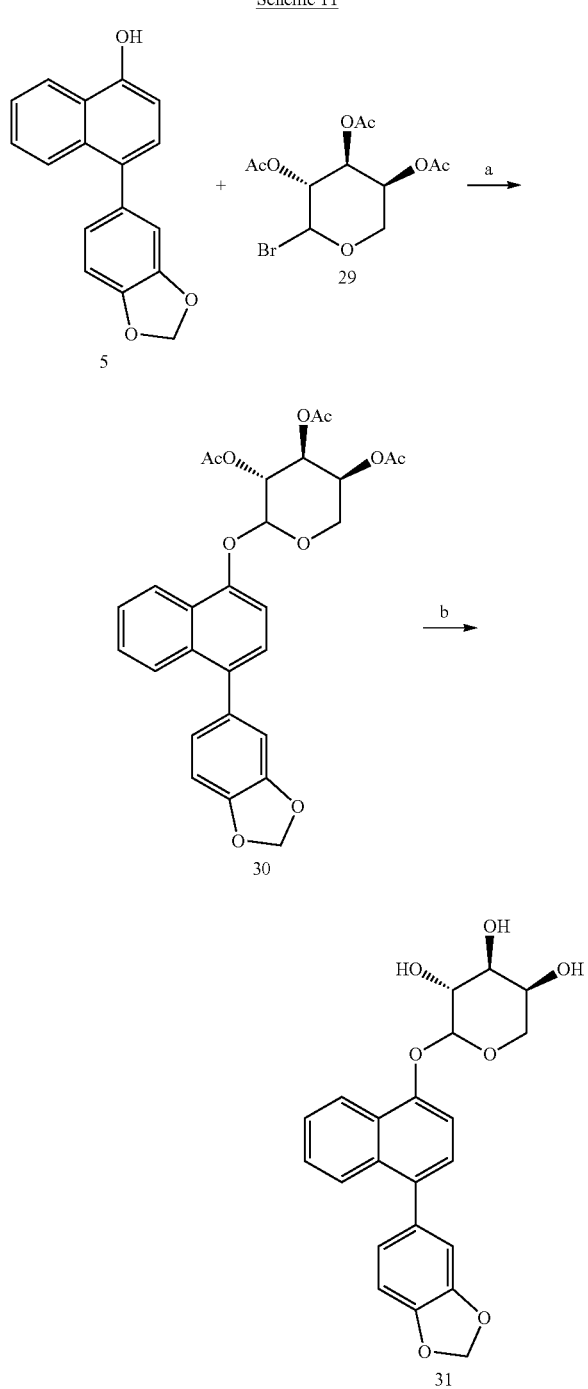

Reagents and conditions: a) Bu₄NBr, 2M NaOH, DCM (Dichloromethane), RT; b) K₂CO₃ MeOH, RT.

Synthesis of (3S,4R,5R)-2-(1-(benzo[d][1,3]dioxol-5-yl)naphthalen-4-yloxy)-tetrahydro-2H-pyran-3,4,5-triacetate (30)

To a 50 mL RBF, 5 (0.4 g, 1.5 mmol), 29 (0.826 g, 3.0 mmol) and tetrabutyl ammonium bromide (0.9 g, 1.5 mmol) were taken in dichloromethane (20 mL) with stirring. To this suspension was added 2M NaOH (3 mL) solution and stirring was continued for 2 h at room temperature. After the completion of reaction as judged by TLC (4:6, EtOAc:Hexane), the reaction mixture was extracted with dichloromethane (4×20 mL). The combined organic layer washed with 10% NaOH solution (3×15 mL) followed by water (2×10 mL) and dried over anhydrous sodium sulfate. Inorganic salts were filtered off; filtrate was concentrated under reduced pressure and crude mass which was purified by column chromatography using EtOAc:Hexane (40:60) as eluent to 30 as white solid.

Synthesis of (3S,4R,5R)-2-(1-(benzo[d][1,3]dioxol-5-yl)naphthalen-4-yloxy)-tetrahydro-2H-pyran-3,4,5-triol (31)

To a solution of 30 (0.416 g, 0.797 mmol) in methanol (20 mL) was added solid anhydrous K₂CO₃ (0.440 g 3.188 mmol) and reaction mixture was stirred at room temperature for 30 min. After completion of reaction as judged by TLC (5:95, MeOH:EtOAc), methanol was removed under reduced pressure, water was added and extracted with CH₂Cl₂ (2×25 mL). Organic layer was dried over anhydrous sodium sulfate, filtered and concentrated to get 31 as white fluffy solid.

¹H-NMR (400 MHz, CDCl3): δ=8.43 (m, 1H), 7.81 (m, 1H), 7.54-7.48 (m, 2H), 7.31 (d, 1H, J=7.6 Hz), 7.14 (d. 1H, J=8.0 Hz), 6.94 (m, 3H), 6.03 (s, 2H), 5.37 (d, 1H, J=5.2 Hz), 5.10 (d, 1H, J=6 Hz), 4.89 (d, 1H, J=5.2 Hz), 4.68 (d, 1H, J=4.4 Hz). 3.86 (m, 3H), 3.61 (m, 2H).

Example 8

Synthesis of Compound of Formula XII (Numbered as 40 in Scheme 13)

Synthesis of N-(1-(benzo[d][1,3]dioxol-5-yl)naphthalen-4-yl)furan-2-carboxamide

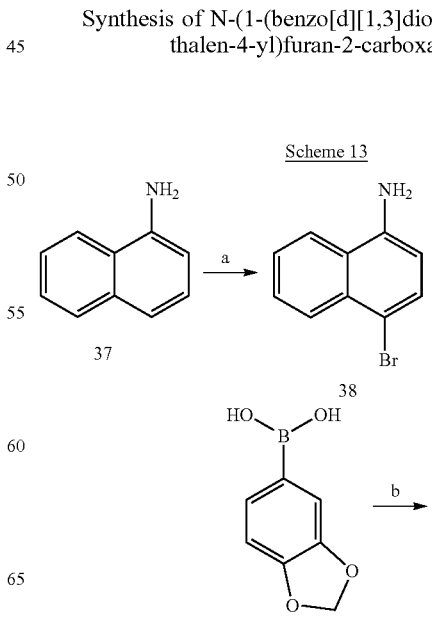

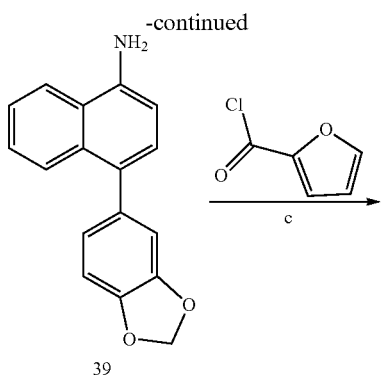

39

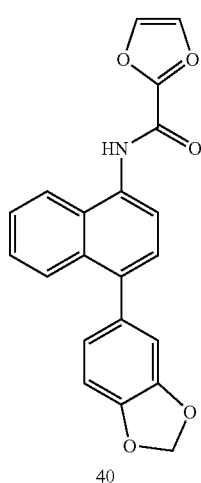

40

Reagents and conditions: a) NBS, DCM, 0° C., 1 hr; b) Tetrakis palladium (0), Na₂CO₃, H₂O, DME (Dimethoxyethane), reflux, 12 hrs; c) furan-2-carbonyl chloride, Triethylamine, DCM, rt, 12 hrs

Synthesis of 4-bromonaphthalen-1-amine (38)

Single neck RBF (500 mL) equipped with magnetic stirrer and guard tube was charged with naphthylamine (37, 10 g, 0.069 mol) and DCM (300 mL). To this solution was added N-Bromosuccinimide (12.43 gm, 0.0698 mol) portionwise with constant stirring over half an hour at 0° C. and stirring was further continued for 1 h at room temperature. During this time all the starting materials was consumed as confirmed by TLC (3:7, EtOAc:Hexane). Reaction mixture was added in cold water (150 mL). The reaction mixture was extracted with dichloromethane (3×200 mL). Organic layer was dried over anhydrous sodium sulphate and concentrated under reduced pressure. The crude mass was purified by column chromatography over silica gel using ethyl acetate (5-20%) in hexane as eluent to afford 38 as a white solid (Yield=3.5 gm).

Synthesis of 4-(benzo[d][1,3]dioxol-5-yl)naphthalen-1-amine (39)

Single necked RBF (250 mL) equipped with magnetic stirrer, condenser and guard tube was charged with 4-bromonaphthalen-1-amine (38, 0.5 g, 2.90 mmol) and 3, 4 (methylenedioxy) phenylboronic acid (0.578 gm, 3.48 mmol) in DME (7 mL). To this solution was added sodium carbonate (0.615 gm, 5.80 mmol) dissolved in water (2.5 mL). Reaction mixture was stirred at rt for 10 minutes and then added tetrakis palladium (0) (0.168 gm, 0.145 mmol). Reaction mixture was refluxed for 12 hrs. During this time all the starting materials was consumed as confirmed by TLC (2:8, EtOAc:Hexane). Reaction mixture was added in water (100 mL). The reaction mixture was extracted with ethyl acetate (3×100 mL). Organic layer was dried over anhydrous sodium sulphate and concentrated under reduced pressure. The crude mass was purified by column chromatography over silica gel using ethyl acetate (5-20%) in hexane as eluent to afford 39 as a white solid (Yield=0.5 gm).

Synthesis of N-(1-(benzo[d][1,3]dioxol-5-yl)naphthalen-4-yl)furan-2-carboxamide (40)

Single neck RBF (500 mL) equipped with magnetic stirrer and guard tube was charged with 4-(benzo[d][1,3]dioxol-5-yl)naphthalen-1-amine (39, 0.2 g, 0.76 mmol), trimethylamine (0.22 mL, 1.52 mmol) and DCM (10 mL). To this solution was added furan-2-carbonyl chloride (0.11 mL, 1.14 mmol) dropwise with constant stirring over half an hour at 0° C. and stirring was further continued for 12 h at room temperature. During this time all the starting materials was consumed as confirmed by TLC (3:7, EtOAc:Hexane). Reaction mixture was added in cold water (100 mL). The reaction mixture was extracted with dichloromethane (2×100 mL). Organic layer was dried over anhydrous sodium sulphate and concentrated under reduced pressure. The crude mass was purified by column chromatography over silica gel using ethyl acetate (10-30%) in hexane as eluent to afford 40 as a white solid (Yield=0.1 gm).

$^{1}$H-NMR (400 MHz, DMSO): δ=8.54 (s, 1H), 8.13 (d, 1H, J=7.6 Hz), 7.98 (t, 2H, J=8.8 Hz), 7.61 (m, 2H), 7.50 (m, 2H), 7.26 (s, 1H), 6.96 (m, 3H), 6.63 (m, 1H), 6.05 (s, 2H).

Example 9

Synthesis of Compound of Formula XIII (Numbered as 36 in Scheme 12)

Synthesis of 5-(benzo[d][1,3]dioxol-5-yl)-8-(benzyloxy)quinoline hydrochloride

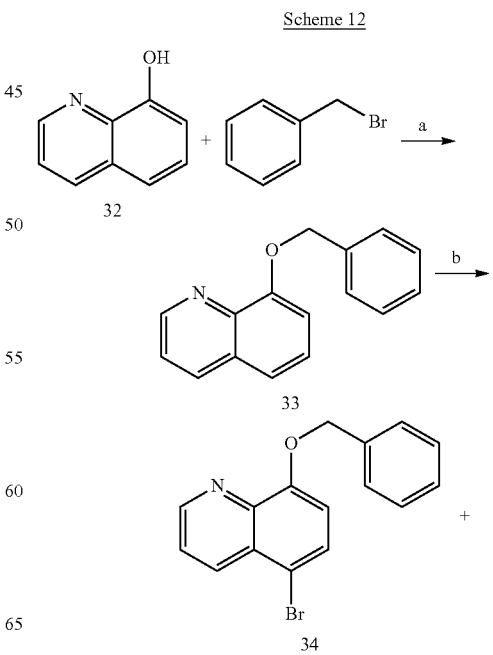

Scheme 12

45

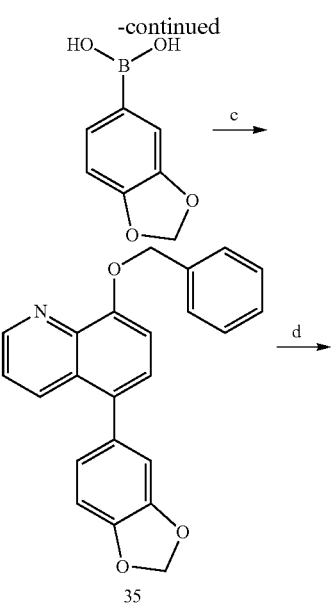

Reagents and conditions: a) K₂CO₃, DMF (Dimethylformamide), RT, 16 hrs; b) NBS, DCM, 0° C., 1 hr; c) Tetrakis palladium (0), Na₂CO₃, H₂O, DME (Dimethoxyethane), reflux, 12 hrs; d) MeOH•HCl, RT, 2 hrs Experimental:

Synthesis of 8-(benzyloxy)quinoline (33)

Three necked RBF (500 mL) equipped with dropping funnel, magnetic stirrer, and guard tube was charged with 8-Hydroxyquinolin (32, 5 g, 0.0344 mol), potassium carbonate (9.5 gm, 0.0688 mol) and DMF (100 mL). To this solution was added benzylbromide (6.13 mL, 0.0516 mol) dropwise with constant stirring over half an hour and stirring was further continued for 12 h at room temperature. During this time all the starting materials was consumed as confirmed by TLC (3:9, EtOAc:Hexane). Reaction mixture was added in cold water (250 mL). The reaction mixture was extracted with ethyl acetate (3×100 mL). All the organic layer combine and washed with water (3×100 mL). Organic layer was dried over anhydrous sodium sulphate and concentrated under reduced pressure. The crude mass was purified by column chromatography over silica gel using ethyl acetate (5-10%) in hexane as eluent to afford 33 as a white solid (Yield=5.2 gm).

46

Synthesis of 8-(benzyloxy)-5-bromoquinoline (34)

Single necked RBF (250 mL) equipped with magnetic stirrer, and guard tube was charged with 8-benzyloxyquinolin (33, 4 g, 0.016 mol) in DCM (100 mL). To this solution was added N-Bromosuccinimide (3.02 gm, 0.016 mol) portiowise with constant stirring over half an hour at 10° C. and stirring was further continued for 1 h at room temperature. During this time all the starting materials was consumed as confirmed by TLC (2:8, EtOAc:Hexane). Reaction mixture was added in cold water (150 mL). The reaction mixture was extracted with dichloromethane (3×100 mL). Organic layer was dried over anhydrous sodium sulphate and concentrated under reduced pressure. The crude mass was purified by column chromatography over silica gel using ethyl acetate (5-10%) in hexane as eluent to afford 34 as a white solid (Yield=3.9 gm).

Synthesis of 5-(benzo[d][1,3]dioxol-5-yl)-8-(benzyloxy)quinoline (35)

Single necked RBF (250 mL) equipped with magnetic stirrer, condenser and guard tube was charged with 8-(benzyloxy)-5-bromoquinoline (34, 1 g, 0.00318 mol) and 3, 4 (methylenedioxy) phenylboronic acid (0.79 gm, 0.00477 mol) in DME (20 mL). To this solution was added sodium carbonate (0.673 gm, 0.00636 mol) dissolved in water (3.2 mL). Reaction mixture was stirred at rt for 10 minutes and then added tetrakis palladium (0) (0.183 gm, 0.000159 mol). Reaction mixture was refluxed for 12 hrs. During this time all the starting materials was consumed as confirmed by TLC (3:7, EtOAc:Hexane). Reaction mixture was added in water (100 mL). The reaction mixture was extracted with ethyl acetate (3×100 mL). Organic layer was dried over anhydrous sodium sulphate and concentrated under reduced pressure. The crude mass was purified by column chromatography over silica gel using ethyl acetate (10-20%) in hexane as eluent to afford 35 as a white solid (Yield=0.94 gm).

Synthesis of 5-(benzo[d][1,3]dioxol-5-yl)-8-(benzyloxy)quinoline hydrochloride (36)

Single necked RBF (250 mL) equipped with magnetic stirrer and guard tube was charged with 5-(benzo[d][1,3] dioxol-5-yl)-8-(benzyloxy)quino line (35, 0.2 g) in dry DCM (10 mL). To this solution was added methanolic HCl at 0° C. Reaction mixture was stirred for 2 hrs at 0° C. Reaction mixture was monitored with TLC. The reaction mixture was concentrated under reduced pressure. The crude compound was crystalized using ethyl acetate and pet ether to afford 36 as a white solid (Yield=0.1 gm).

¹H-NMR (400 MHz, DMSO): δ=9.1 1 (d, 1H, J=4.4 Hz), 8.74 (d, 1H, J=8.4 Hz), 7.93 (m, 1H), 7.63 (m, 4H), 7.41 (m, 3H), 7.14 (m, 2H), 7.06 (m, 1H), 6.12 (s, 2H). 5.51 (s, 2H).

Example 10

Synthesis of Compound of Formula XIV
(Numbered as 41 in Scheme 14)

Synthesis of
4-phenylnaphthalen-N,N-Di-methylsulphonamide

Scheme 14

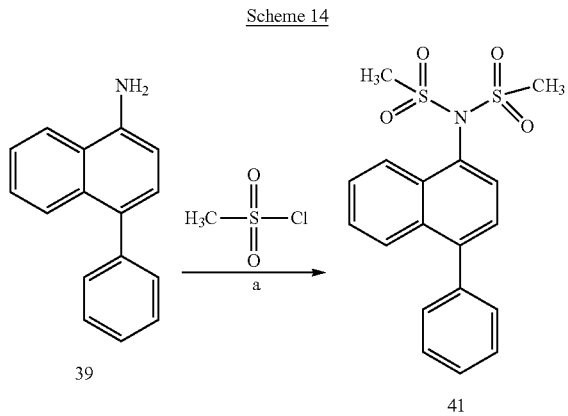

Reagents and conditions: a) Triethylamine, DCM, 0° C., 1 hr, RT for 2 hr

Experimental

Synthesis of
4-phenylnaphthalen-N,N-Di-methylsulphonamide.
(Comp. 41)

Single neck RBF (100 mL) equipped with magnetic stirrer and guard tube was charged with 4-phenylnaphthalen-1-amine (39, 0.1 g, 0.45 mmol), trimethylamine (0.5 mL, 0.90 mmol) and DCM (10 mL). To this solution was added methane sulphonyl chloride (0.5 mL, 0.67 mmol) dropwise with constant stirring over half an hour at 0° C. and stirring was further continued for 2 h at room temperature. During this time all the starting materials was consumed as confirmed by TLC (1:9, EtOAc:Hexane). Reaction mixture was added in cold water (100 mL). The reaction mixture was extracted with dichloromethane (2×100 mL). Organic layer was dried over anhydrous sodium sulphate and concentrated under reduced pressure. The crude mass was purified by column chromatography over silica gel using ethyl acetate (5-20%) in hexane as eluent to afford 41 as a white solid (Yield=0.15 gm).

$^1$H-NMR (400 MHz, DMSO): δ–8.15 (d, 1H, J–8.4 Hz), 7.94 (d, 1H, J–8.4 Hz), 7.68 (m, 1H), 7.60 (m, 1H), 7.51 (m, 7H), 3.56 (s, 6H).

Example 11

Cancer Cell Assays
In Vitro Antiproliferative Assay (MTT Assay)

MTT assay is a simple and sensitive assay where, metabolic reducing activity of the cells is measured. The increase of this activity in time is taken as a parameter of cell growth. If treatment with a drug impairs this increase, the action may be a consequence of growth inhibition, cell killing or both. The compounds of Formula V to XIV of the present invention, standard cytotoxic drug (e.g. Cisplatin) were tested at different concentrations (1, 0.1, 0.01, 0.001 mM) using breast and prostate cancer cell lines. All cell lines were cultured in a 37° C. incubator with a 5% $CO_2$ environment. Compounds were dissolved in DMSO with a concentration of 0.1M (stock solution). Cells were seeded into 96-well plates at suitable plating efficiency.

Following Plating Efficiencies were Standardized for MTT Assay:

TABLE 1

| Cell lines | Name of the cell line | Plating efficiency (No. of cells/well or per 200 μl) |
|---|---|---|
| Breast | MCF7 | 7500 |
|  | MDAMB231 | 10000 |
| Prostate | PC3 | 10000 |
|  | DU145 | 5000 |

The MTT procedure followed was as follows. Briefly, the cells were plated in 96 well plate as per predetermined plating efficiency (Table 1) The plates were then incubated for 24 hrs in 5% $CO_2$ atmosphere at 37° C. Appropriate concentrations of the drugs were then added to the plate and further incubation was carried out for 48 hrs (in 5% $CO_2$ atmosphere at 37° C.). The assay plate was then centrifuged twice at 3000 rpm for 3 mins and supernatant was then discarded. 100 ul of MTT solution (0.5 mg/ml) was then added to each well of the plate and it was further incubated for 4 hrs (in 5% $CO_2$ atmosphere at 37° C.) Following 4 hr incubation, the plate was then centrifuged twice, and supernatant was aspirated off very carefully. 200 ul of DMSO was then added to each well to solubilize. MTT crystals and mixed well by shaking the plate. XY graph of log Percent viability was then plotted against log drug concentration. 1050 (Drug concentration inhibiting the 50% of cell population) was then calculated by regression analysis.

Soft Agar Assay

The Soft Agar Colony-formation Assay is an anchorage-independent growth assay in soft agar, which is one of the most stringent assays for detecting malignant transformation of cells. For this assay, malignant cells are cultured with appropriate controls in soft agar medium for 1-2 weeks. Following this incubation period, formed colonies can either be analyzed morphologically using cell stain and quantifying the number of colonies formed. The results of the assay are comparable to those obtained after injecting tumorigenic cells into nude mice and is regarded as the "gold standard" for testing the tumorigenicity of cells in vitro (one of the important features of cancer stem cells, CSCs).

Briefly, for Soft Agar Assay a mixture of 50 ul of 2× medium (taken appropriately as per cell line) and 50 ul of 1.2% Bacto Agar were plated on to each well of 96 well micro titer assay plate. 10 ul of cells (Of specific plating efficiency pre-standardized for respective cell line) were mixed with 20 ul of 2× medium and 30 ul of 0.8% of Bacto Agar and 1.6 ul of drug (of appropriate concentration) in a vial and transferred to the solidified pre-layers of the assay plates. The cells were then allowed to grow and form colonies at 37° C. and 5% CO2 for 1 week. An intermittent feeding with 50 ul of appropriate 2× medium was performed after 3 days of experimental set up. 16 ul of Alamar Blue (1.5 mg/ml) was then added to all the wells to quantify the developed colonies. The plates were incubated for 24 hrs at 37° C. Absorbance was then measured at 630 nm. XY graph of log Percent viability was then plotted against log drug concentration. IC50 (Drug concentration inhibiting the 50% of cell population) was then calculated by regression analysis.

Following Plating Efficiencies Were Standardized for Soft Agar Assay:

TABLE 2

| Cell lines | Name of the cell line | Plating efficiency (No. of cells/well) |
|---|---|---|
| Breast | MDAMB231 | 7500 |
| Prostate | PC3 | 5000 |

Stem Cell Assays:

In Vitro Sphere-Forming Assay:

Sphere assay measures the ability of Cancer Stein Cells to form spheres in specially designed serum-free medium. We have used this assay to measure the killing efficiency of the test compounds as compared to the standard chemotherapeutic drug, Cisplatin.

Materials and Reagents:50× B27 Supplement (Life Technologies, Invitrogen, Catalog No.: 17502-044), Fibroblast Growth Factor (FGF) (Sigma-Aldrich, Catlog No.: F029125), Epidermal Growth Factor (EGF) (Sigma-Aldrich, Catlog No.: E9644), Insulin (Sigma, Catlog No.: 19278), Dulbecco's Modified Eagle Medium/F12 (HiMedia Catlog No.: AL139-6), Dulbecco's Phosphate Buffered Saline (HiMedia Catlog No.: TL1006), Trypan Blue (TC193), Prostate Epithelial Media (LONZA, Catlog No.: CC-3166) MEGM (LONZA, Catlog No.: CC-3051), Heparin (Sigma, Catlog No.: H3393), Penstrep (HiMedia, Catlog No.: A002)

Mammosphere Media Preparation (For 100 mL): 1 g methyl cellulose autoclaved with magnetic stirrer Plain media (MEBM), 100 mL added and dissolved under magnetic stirring. After complete dissolution, add: FGF-80 μL, EGF-40 μL, Penstrep-1 mL, Heparin-400 μL.

Prostosphere Media Preparation (For 100 mL):1 g methyl cellulose autoclaved with magnetic stirrer, Plain media (Prostate Epithelial Basal Medium), 100 mL added and dissolved, under magnetic stirring. After complete dissolution, add: Insulin-40 μL, B27-2 mL, EGF-80 μL, Penstrep-1 ml.

Procedure: —The cells were trypsinised and made into single-cell suspension by passing through cell strainers (100 μl and 40 μl, respectively), The cells were diluted at the concentration of 2000 cells/100 μL and suspended in either Mammosphere (for breast cell lines) or Prostosphere (for prostate cell lines). 100 μL of this suspension was added into each well of 96-well suspension plates and incubated at 37° C., 5% $CO_2$ for 24 hrs. Appropriate concentrations of the drugs (2 μL) were added into respective wells with 100 μL of stem cell culture medium. Plates were incubated at 37° C., 5% $CO_2$ for 72 hrs. After incubation 2.5 μL of the respective drug concentration and 50 μL of stem cell culture medium were added into each well and the plates were further incubated at 37° C., 5% $CO_2$ for 72 hrs. 3 μL of the respective drug concentration was added with 50 μL of stem cell culture medium again after incubation and plates were incubated again for 72 hrs at 37° C., 5% $CO_2$. Number of primary spheres formed for each concentration was counted. A comparative graph of number of spheres formed was plotted against the concentration and the growth curve was compared with the positive control.

Normal Cell Assays:

It is very important that the sensitivity of a cytotoxic drug towards malignant and normal cells is different. In the first place, the clinical use of drugs with a preferential toxicity towards malignant cells is preferred.

In order to test the activity of cytotoxic drugs towards normal cells, we performed MTT Assay for these cytotoxic drugs using lymphocytes obtained from a healthy donor.

Human lymphocytes can be readily isolated from peripheral blood. centrifuged at low speeds for 30 mins. Briefly, diluted defibrinated fresh blood was overlaid gradually on HiSeP LSM1077 and centrifuged at low speed for 30 mins. The lymphocyte layer (the buffy coat) (Fig) was carefully removed in a new collection tube. The buffy coat was given another wash, by the diluent buffer, to reduce the platelet contamination. The supernatant was discarded, and the pellet was resuspended in diluent buffer. The viability was checked by Haemocytometer. Cells with Viability and Purity of 95% and more were considered for the assay. MTT assay was performed with these cells as described above with plating efficiency of 0.7 million/ml.

Example 12

Results of Activity of Formula V

TABLE 3

MTT Results of Formula V for Breast Cell lines IC50 in micromolar

| Sr. No | Cell line | Cisplatin | Formula V |
|---|---|---|---|
| 1. | MDAMB231 | 32.68 | 4.61 |

Table 3 indicates that activity of Formula V on breast cancer cell line is higher compared to standard chemotherapeutic drug Cisplatin in MTT assay.

TABLE 4

MTT Results of FORMULA V for Prostate Cell lines IC50 in micromolar

| Sr. No | Cell line | Cisplatin | Formula V |
|---|---|---|---|
| 1 | PC3 | 27.99 | 6.19 |

The results indicate that activity of Formula V on prostate cancer cell line is higher compared to standard chemotherapeutic drug Cisplatin in MTT assay.

TABLE 5

Soft Agar Assay Results of Formula V for Breast Cell lines IC50 in micromolar

| Sr. No | Cell line | Cisplatin | Formula V |
|---|---|---|---|
| 1. | MDAMB231 | 41.7 | 3.45 |

Table 5 indicates the anticancer activity exhibited by Formula V is on breast cancer cell line MDAMB231 is higher than standard chemotherapeutic drug Cisplatin in soft Agar Assay.

TABLE 6

Soft Agar Assay Results of Formula V for Prostate Cell lines IC50 in micromolar

| Sr. No | Cell line | Cisplatin | Formula V |
|---|---|---|---|
| 1 | PC3 | 20.56 | 10.6 |

Table 6 indicates the anticancer activity of Formula V is higher on prostate cancer cell line in soft Agar Assay

TABLE 7

3D sphere count of MDAMB231 in Mammosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 18(±2) | 31(±3) | 35(±2) | 42(±3) | 50(±3) | 85(±3) | 76(±4) |
| FORMULA V | 0(±0) | 7(±2) | 12(±1) | 24(±3) | 40(±3) | 85(±3) | 76(±4) |

Table 7 indicates Formula V is effective on spheres of MDAMB231 compared to standard chemotherapeutic drug Cisplatin.

TABLE 8

3D sphere count of PC3 in Prostosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 25(±3) | 32(±2) | 40(±3) | 47(±5) | 58(±4) | 77(±5) | 65(±4) |
| FORMULA V | 0(±0) | 21(±4) | 36(±3) | 40(±5) | 50(±5) | 77(±5) | 65(±4) |

Table 8 indicates that Formula V is more effective on spheres of PC3 compared to standard chemotherapeutic drug Cisplatin.

Example 13

Results of Activity of Formula VI

TABLE 9

MTT Results of Formula VI for Breast Cell lines IC50 in micromolar

| Sr. No | Cell line | Cisplatin | Formula VI |
|---|---|---|---|
| 1. | MDAMB231 | 32.68 | 10.09 |

Table 9 indicates that activity of Formula VI on breast cancer cell line is higher compared to standard chemotherapeutic drug Cisplatin in MTT assay.

TABLE 10

MTT Results of Formula VI for Prostate Cell lines IC50 in micromolar

| Sr. No | Cell line | Cisplatin | Formula VI |
|---|---|---|---|
| 1 | PC3 | 27.99 | 5.65 |

Table 10. indicates that activity of FORMULA VI on Prostrate cancer cell line is higher compared to standard chemotherapeutic drug Cisplatin in MTT assay.

Results of MTT assay indicates that compound of Formula VI exhibits higher anticancer activity on breast and prostate Cancer cell lines compared to standard chemo therapeutic drug Cisplatin.

TABLE 11

Soft Agar Assay Results of Formula VI for Breast Cell lines IC50 in micromolar

| Sr. No | Cell line | Cisplatin | Formula VI |
|---|---|---|---|
| 1. | MDAMB231 | 24.79 | 14.22 |

Table 11 indicates the anticancer activity of Formula VI is higher on breast cancer cell line MDAMB231 compared to standard chemotherapeutic drug Cisplatin in soft Agar Assay.

TABLE 12

Soft Agar Assay Results of Formula VI for Prostate Cell lines IC50 in micromolar

| Sr. No | Cell line | Cisplatin | Formula VI |
|---|---|---|---|
| 1 | PC3 | 21.30 | 3.25 |

Table 12 indicates the anticancer activity of Formula. VI is higher on prostate cancer cell line PC3 compared to standard chemotherapeutic drug Cisplatin in soft Agar Assay The results Indicates that Formula VI exhibits higher anticancer activity on breast and prostate Cancer cell lines compared to standard chemotherapeutic drug Cisplatin in Soft Agar Assay.

TABLE 13

3D sphere count of MDAMB231 in Mammosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 18(±2) | 31(±3) | 35(±2) | 42(±3) | 50(±3) | 85(±3) | 76(±4) |
| FORMULA VI | 0(±0) | 7(±2) | 24(±3) | 36(±2) | 44(±3) | 85(±3) | 76(±4) |

Table 13 indicates that Formula VI is more effective on spheres of MDAMB231 compared to standard chemotherapeutic drug Cisplatin.

TABLE 14

3D sphere count of PC3 in Prostosphere media at plating efficiency of 2000 cells/well (n = 6 ± S.D)

| | Drug Conc in uM | | | | | GC(Growth Control) | GCD (Growth Control With DMSO) |
|---|---|---|---|---|---|---|---|
| | 250 | 25 | 2.5 | 0.25 | 0.025 | | |
| Cisplatin | 25(±3) | 32(±2) | 40(±3) | 47(±5) | 58(±4) | 77(±5) | 65(±4) |
| Formula VI | 0(±0) | 21(±2) | 30(±2) | 28(±2) | 40(±3) | 77(±5) | 65(±4) |

Table 14 indicates that Formula VI is more effective on spheres of PC3 compared to standard chemotherapeutic drug Cisplatin.

Example 14

Results of Activity of Formula VII

TABLE 15

MTT Results of Formula VII for Breast Cancer Cell lines IC50 in micromolar

| Sr. No | Cell line | Cisplatin | FORMULA VII |
|---|---|---|---|
| 1. | MCF-7 | 29.57 | 2.78 |
| 2. | MDAMB231 | 38.46 | 2.04 |

Table 15 indicates that activity of Formula VII on breast cancer cell lines is higher compared to standard chemotherapeutic drug Cisplatin in MTT assay.

TABLE 16

MTT Results Formula VII for Prostate Cancer Cell lines IC50 in micromolar

| Sr. No | Cell line | Cisplatin | MSP008-7 (FORMULA VII) |
|---|---|---|---|
| 1. | PC3 | 29.02 | 6.32 |
| 2. | DU145 | 23.86 | 3.57 |

Table 16 indicates that activity of Formula VII on prostate cancer cell lines is higher compared to standard chemotherapeutic drug Cisplatin in MTT assay.

TABLE 17

Soft Agar Assay Results of Formula VII for Breast Cell lines IC50 in micromolar

| Sr. No | Cell line | Cisplatin | Formula VII |
|---|---|---|---|
| 1. | MDAMB231 | 24.79 | 7.91 |

Table 17 indicates the anticancer activity of FORMULA VII is higher on breast cancer cell line MDAMB231 compared to standard chemotherapeutic drug Cisplatin in soft Agar Assay.

TABLE 18

Soft Agar Assay Results of Formula VII for Prostate Cell lines IC50 in micromolar

| Sr. No | Cell line | Cisplatin | Formula VII |
|---|---|---|---|
| 1 | PC3 | 21.30 | 0.36 |

Table 18 results indicate the anticancer activity of Formula VII is higher on prostate cancer cell line PC3 compared to standard chemotherapeutic drug Cisplatin in soft Agar Assay.

In Vitro Sphere-Forming Assay

TABLE 19

3D sphere count of MDAMB231 in Mammosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 23(±5) | 38(±8) | 51(±5) | 69(±7) | 89(±4) | 86(±6) | 78(±2) |
| FORMULA VII | 0(±0) | 40(±3) | 40(±7) | 46(±7) | 47(±4) | 86(±6) | 78(±2) |

Table 19 indicates the that Formula VII is more effective on spheres of MDAMB231 compared to standard chemotherapeutic drug Cisplatin.

TABLE 20

3D sphere count of PC3 in Prostosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 30(±5) | 31(±5) | 41(±4) | 49(±7) | 47(±4) | 68(±8) | 62(±2) |
| FORMULA VII | 0(±0) | 9(±2) | 23(±3) | 31(±5) | 64(±8) | 68(±8) | 62(±2) |

Table 20 indicates that Formula VII is more effective on spheres of PC3 compared to standard chemotherapeutic drug Cisplatin.

Example 15

Results of Activity Formula VIII

TABLE 21

MTT Results of Formula VIII for Breast Cell lines IC50 in micromolar

| Sr. No | Cell line | Cisplatin | Formula VIII |
|---|---|---|---|
| 1. | MCF-7 | 29.57 | 1.05 |
| 2. | MDAMB231 | 38.46 | 3.14 |

Table 21 indicates that activity of FORMULA VIII on breast cancer cell lines is higher compared to standard therapeutic drug Cisplatin in MTT assay.

TABLE 22

MTT Results of Formula VIII for Prostate Cell lines IC50 in micromolar

| Sr. No | Cell line | Cisplatin | Formula VIII |
|---|---|---|---|
| 1. | PC3 | 29.02 | 3.91 |
| 2. | DU145 | 23.86 | 4.28 |

Table 22 indicates that activity of Formula VIII on prostate cancer cell lines is higher compared to standard therapeutic drug Cisplatin in MTT assay.

TABLE 23

Soft Agar Assay Results of Formula VIII for Breast Cell lines IC50 in micromolar

| Sr. No | Cell line | Cisplatin | Formula VIII |
|---|---|---|---|
| 1. | MDAMB231 | 24.79 | 1.32 |

Table 23 indicates the anticancer activity of Formula VIII is higher on breast cancer cell line MDAMB231 compared to standard therapeutic drug Cisplatin in soft Agar Assay.

TABLE 24

Soft Agar Assay Results of Formula VIII for Prostate Cell lines IC50 in micromolar

| Sr. No | Cell line | Cisplatin | Formula VIII |
|---|---|---|---|
| 1 | PC3 | 21.30 | 1.96 |

Table 24 indicates the anticancer activity of Formula VIII is higher on prostate cancer cell line PC3 compared to standard therapeutic drug Cisplatin in soft Agar Assay.

TABLE 25

3D sphere count of MDAMB231 in Mammosphere media at plating efficiency of 2000 cells/well (n = 6 ± S.D)

| | Drug Conc in uM | | | | | GC (Growth Control) | GCD(Growth Control With DMSO) |
|---|---|---|---|---|---|---|---|
| | 250 | 25 | 2.5 | 0.25 | 0.025 | | |
| Cisplatin | 23(±5) | 38(±8) | 51(±5) | 69(±7) | 89(±4) | 86(±6) | 78(±2) |
| Formula VIII | 0(±0) | 8(±2) | 13(±2) | 29(±4) | 36(±3) | 86(±6) | 78(±2) |

Table 25 indicates the that Formula VIII is more effective on spheres of MDAMB231 compared to standard therapeutic drug Cisplatin

TABLE 26

3D sphere count of PC3 in Prostosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 30(±5) | 31(±5) | 41(±4) | 49(±7) | 47(±4) | 68(±8) | 62(±2) |
| Formula VIII | 0(±0) | 8(±2) | 13(±3) | 24(±3) | 29(±3) | 68(±8) | 62(±2) |

Table 26 indicates that Formula VIII is more effective on spheres of PC3 compared to standard chemotherapeutic drug Cisplatin

Example 16

Results of Activity of Formula IX

TABLE 27

MTT Results of Formula IX for Breast Cell lines IC50 in micromolar

| Sr. No. | Cell line | Cisplatin | FORMULA IX |
|---|---|---|---|
| 1. | MCF-7 | 29.57 | 5.24 |
| 2. | MDAMB231 | 38.46 | 5.26 |

Table 27 indicates that activity of FORMULA IX on breast cancer cell lines is higher compared to standard chemotherapeutic drug Cisplatin in MTT assay.

TABLE 28

MTT Results of Formula IX for Prostate Cell lines IC50 in micromolar

| Sr. No | Cell line | Cisplatin | Formula IX |
|---|---|---|---|
| 1. | PC3 | 29.02 | 5.62 |
| 2. | DU145 | 23.86 | 8.91 |

Table 28 indicates that activity of Formula IX on prostate cancer cell lines is higher compared to standard chemotherapeutic drug Cisplatin in MTT assay.

TABLE 29

Soft Agar Assay Results of Formula IX for Breast Cell lines IC50 in micromolar

| Sr. No | Cell line | Cisplatin | Formula IX |
|---|---|---|---|
| 1. | MDAMB231 | 24.79 | 2.12 |

Table 29 indicates the anticancer activity of Formula IX is higher on breast cancer cell line MDAMB231 compared to standard chemotherapeutic drug Cisplatin in soft Agar Assay.

TABLE 30

Soft Agar Assay Results of Formula IX for Prostate Cell lines IC50 in micromolar

| Sr. No | Cell line | Cisplatin | Formula IX |
|---|---|---|---|
| 1 | PC3 | 21.30 | 4.81 |

Table 30 indicates the anticancer activity of Formula IX is higher on prostate cancer cell line PC3 compared to standard chemotherapeutic drug Cisplatin in soft Agar Assay.

TABLE 31

3D sphere count of MDAMB231 in Mammosphere media at plating efficiency of 2000 cells/well (n = 6 ± S.D)

| | Drug Conc in uM | | | | | GC (Growth Control) | GCD(Growth Control With DMSO) |
|---|---|---|---|---|---|---|---|
| | 250 | 25 | 2.5 | 0.25 | 0.025 | | |
| Cisplatin | 31(±4) | 37(±4) | 43(±2) | 48(±2) | 62(±6) | 82(±4) | 74(±3) |
| Formula IX | 0(±0) | 22(±3) | 26(±3) | 40(±5) | 52(±4) | 82(±4) | 74(±3) |

Table 31 indicates that Formula IX is more effective on spheres of MDAMB231 compared to standard chemotherapeutic drug Cisplatin.

TABLE 32

3D sphere count of PC3 in Prostosphere media at plating efficiency of 2000 cells/well (n = 6 ± S.D)

| | Dilution (from stock of 0.1M) Final conc | | | | | | |
|---|---|---|---|---|---|---|---|
| | 10<br>250 μM | 100<br>25 μM | 1000<br>2.5 μM | 10,000<br>0.25 μM | 100,000<br>0.025 μM | GC | GCD |
| Cisplatin | 22(±4) | 33(±3) | 46(±2) | 55(±5) | 62(±5) | 68(±2) | 56(±2) |
| Formula IX | 0(±0) | 31(±3) | 37(±5) | 44(±4) | 60(±7) | 68(±2) | 56(±2) |

Table 32 indicates that Formula IX is more effective on spheres of PC3 compared to standard chemotherapeutic drug Cisplatin.

Example 17

Results of Activity of FORMULA X

TABLE 33

MTT Results of Formula X for Breast Cell lines IC50 in micromolar

| Sr. No | Cell line | Cisplatin | Formula X |
|---|---|---|---|
| 1. | MCF-7 | 32.35 | 3.46 |
| 2. | MDAMB231 | 36.98 | 3.16 |

Table 33 indicates that activity of Formula X on breast cancer cell lines is higher compared to standard chemotherapeutic drug Cisplatin in MTT assay.

TABLE 34

MTT Results of Formula X for Prostate Cell lines IC50 in micromolar

| Sr. No. | Cell line | Cisplatin | Formula X |
|---|---|---|---|
| 1. | PC3 | 40.73 | 2.6 |
| 2. | DU145 | 42.95 | 3.28 |

Table 34 indicates that activity of Formula X on prostate cancer cell lines is higher compared to standard chemotherapeutic drug Cisplatin in MTT assay.

TABLE 35

Soft Agar Assay Results of Formula X for Breast Cell lines IC50 in micromolar

| Sr. No | Cell line | Cisplatin | MSP008-44(FORMULA X) |
|---|---|---|---|
| 1. | MDAMB231 | 37.33 | 2.07 |

Table 35 indicates the anticancer activity of Formula X is higher on breast cancer cell line MDAMB231 compared to standard chemotherapeutic drug Cisplatin in soft Agar Assay.

TABLE 36

Soft Agar Assay Results of Formula X for Prostate Cell lines IC50 in micromolar

| Sr. No | Cell line | Cisplatin | Formula X |
|---|---|---|---|
| 1 | PC3 | 23.77 | 2.38 |

Table 36 indicates the anticancer activity of Formula X is higher on prostate cancer cell line PC3 compared to standard chemotherapeutic drug Cisplatin in soft Agar Assay.

In Vitro Sphere-Forming Assay

TABLE 37

3D sphere count of MDAMB231 in Mammosphere media at plating efficiency of 2000 cells/well (n = 6 ± S.D)

| | Drug Conc in uM | | | | | |
|---|---|---|---|---|---|---|
| | 250 | 25 | 2.5 | 0.25 | 0.025 | GC(Growth Control) | GCD(Growth Control With DMSO) |
| Cisplatin | 31(±4) | 37(±4) | 43(±2) | 48(±2) | 62(±6) | 82(±4) | 74(±3) |
| Formula X | 0(±0) | 24(±3) | 28(±3) | 37(±4) | 39(±4) | 82(±4) | 74(±3) |

Table 37 indicates that Formula X is more effective on spheres of MDAMB231 compared to standard chemotherapeutic drug Cisplatin.

Example 18

Results of Activity of Formula XI

TABLE 38

MTT Results of Formula XI for Breast Cell lines IC50 in micromolar

| Sr. No | Cell line | Cisplatin | Formula XI |
|---|---|---|---|
| 1. | MCF-7 | 32.35 | 4.36 |
| 2. | MDAMB231 | 36.98 | 9.77 |

Table 38 indicates that activity of Formula XI on breast cancer cell lines is higher compared to standard chemotherapeutic drug Cisplatin in MTT assay.

TABLE 39

MTT Results of Formula XI for Prostate Cell lines IC50 in micromolar

| Sr. No | Cell line | Cisplatin | Formula XI |
|---|---|---|---|
| 1. | PC3 | 40.73 | 4.16 |
| 2. | DU145 | 42.95 | 10.23 |

Table 39 indicates that activity of FORMULA XI on prostate cancer cell lines is higher compared to standard chemotherapeutic drug Cisplatin in MTT assay.

TABLE 40

Soft Agar Assay Results of Formula XI for Breast Cell lines IC50 in micromolar

| Sr. No | Cell line | Cisplatin | Formula XI |
|---|---|---|---|
| 1. | MDAMB231 | 37.33 | 2.08 |

Table 40 indicates the anticancer activity of Formula XI is higher on breast cancer cell line MDAMB231 compared to standard chemotherapeutic drug Cisplatin in soft Agar Assay.

TABLE 41

Soft Agar Assay Results of Formula XI for Prostate Cell lines IC50 in micromolar

| Sr. No | Cell line | Cisplatin | Formula XI |
|---|---|---|---|
| 1 | PC3 | 23.77 | 18.84 |

Table 41 indicates the anticancer activity of Formula XI is higher on prostate cancer cell line PC3 compared to standard chemotherapeutic drug Cisplatin in soft Agar Assay.

Example 19

Results of Activity of Formula XII

TABLE 42

MTT Results of Formula XII for Breast Cell lines IC50 in micromolar

| Sr. No | Cell line | Cisplatin | Formula XII |
|---|---|---|---|
| 1. | MCF-7 | 32.96 | 4.95 |
| 2. | MDAMB231 | 32.73 | 3.37 |

Table 42 indicates that activity of Formula XII on breast cancer cell lines is higher compared to standard chemotherapeutic drug Cisplatin in MTT assay.

TABLE 43

MTT Results of Formula XII for Prostate Cell lines IC50 in micromolar

| Sr. No | Cell line | Cisplatin | Formula XII |
|---|---|---|---|
| 1. | PC3 | 35.81 | 19.63 |
| 2. | DU145 | 34.43 | 9.82 |

Table 43 indicates that activity of Formula XII on prostate cancer cell lines is higher compared to standard chemotherapeutic drug Cisplatin in MTT assay.

TABLE 44

Soft Agar Assay Results of Formula XII for Breast Cell lines IC50 in micromolar

| Sr. No | Cell line | Cisplatin | Formula XII |
|---|---|---|---|
| 1. | MDAMB231 | 23.93 | 2.14 |

Table 44 indicates the anticancer activity of Formula XII is higher on breast cancer cell line MDAMB231 compared to standard chemotherapeutic drug Cisplatin in soft Agar Assay.

TABLE 45

Soft Agar Assay Results of Formula XII for Prostate Cell lines IC50 in micromolar

| Sr. No | Cell line | Cisplatin | Formula XII |
|---|---|---|---|
| 1 | PC3 | 21.88 | 3.36 |

Table 45 indicates the anticancer activity of Formula XII is higher on prostate cancer cell line PC3 compared to standard chemotherapeutic drug Cisplatin in soft Agar Assay.

In Vitro Sphere-Forming Assay

TABLE 46

3D sphere count of MDAMB231 in Mammosphere media at plating efficiency of 2000 cells/well (n = 6 ± S.D)

| | Drug Conc in uM | | | | | GC (Growth Control) | GCD(Growth Control With DMSO) |
|---|---|---|---|---|---|---|---|
| | 250 | 25 | 2.5 | 0.25 | 0.025 | | |
| Cisplatin | 26(±3) | 35(±2) | 46(±3) | 58(±3) | 67(±2) | 72(±3) | 64(±2) |
| Formula XII | 0(±0) | 8(±1) | 17(±2) | 27(±2) | 31(±2) | 72(±3) | 64(±2) |

Table 46 indicates that Formula XII is more effective on spheres of MDAMB231 compared to standard chemotherapeutic drug Cisplatin.

TABLE 47

3D sphere count of PC3 in Prostosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 21(±2) | 32(±3) | 39(±2) | 42(±3) | 45(±2) | 80(±5) | 76(±4) |
| Formula XII | 0(±0) | 15(±2) | 23(±2) | 28(±3) | 37(±3) | 80(±5) | 76(±4) |

Table 47 indicates that Formula XII is more effective on spheres of PC3 compared to standard chemotherapeutic drug Cisplatin.

Example 20

Results of Activity of Formula XIII

TABLE 48

MTT Results Formula XIII for Breast Cell lines IC50 in micromolar

| Sr. No | Cell line | Cisplatin | Formula XIII |
|---|---|---|---|
| 1. | MDAMB231 | 35.48 | 8.00 |

Table 48 indicates that activity of Formula XIII on breast cancer cell lines is higher compared to standard chemotherapeutic drug Cisplatin in MTT assay.

TABLE 49

MTT Results of Formula XIII for Prostate Cell lines IC50 in micromolar

| Sr. No | Cell line | Cisplatin | Formula XIII |
|---|---|---|---|
| 1. | PC3 | 36.39 | 4.33 |
| 2. | DU145 | 35.48 | 4.06 |

Table 49 indicates that activity of Formula XIII on prostate cancer cell lines is higher compared to standard chemotherapeutic drug Cisplatin in MTT assay.

TABLE 50

Soft Agar Assay Results of Formula XIII for Breast Cell lines IC50 in micromolar

| Sr. No | Cell line | Cisplatin | Formula XIII |
|---|---|---|---|
| 1. | MDAMB231 | 23.93 | 2.68 |

Table 50 indicates the anticancer activity of Formula XIII is higher on breast cancer cell line MDAMB231 compared to standard chemotherapeutic drug Cisplatin in soft Agar Assay.

TABLE 51

Soft Agar Assay Results of Formula XIII for
Prostate Cell lines IC50 in micromolar

| Sr. No | Cell line | Cisplatin | Formula XIII |
|---|---|---|---|
| 1 | PC3 | 21.88 | 6.32 |

Table 51 indicates the anticancer activity of Formula XIII is higher on prostate cancer cell line PC3 compared to standard chemotherapeutic drug Cisplatin in soft Agar Assay.

In Vitro Sphere-Forming Assay

TABLE 52

3D sphere count of MDAMB231 in Mammosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 26(±3) | 35(±2) | 46(±3) | 58(±3) | 67(±2) | 72(±3) | 64(±2) |
| Formula XIII | 0(±0) | 13(±2) | 27(±2) | 36(±3) | 45(±2) | 72(±3) | 64(±2) |

Table 52 indicates that Formula XIII is more effective on spheres of MDAMB231 compared to standard chemotherapeutic drug Cisplatin.

TABLE 53

3D sphere count of PC3 in Prostosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 21(±2) | 32(±3) | 39(±2) | 42(±3) | 45(±2) | 80(±5) | 76(±4) |
| FORMULA XIII | 0(±0) | 14(±1) | 27(±3) | 39(±5) | 41(±7) | 80(±5) | 76(±4) |

Table 53 indicates that Formula XIII is more effective on spheres of PC3 compared to standard chemotherapeutic drug Cisplatin.

Example 21

Results of Activity of Formula XIV

TABLE 54

Soft Agar Assay Results of Formula XIV
on Breast Cell lines IC50 in micromolar

| Sr. No | Cell line | Cisplatin | Formula XIV |
|---|---|---|---|
| 1. | MDAMB231 | 24.79 | 3.12 |

Table 54 indicates the anticancer activity of Formula XIV is higher on breast cancer cell line MDAMB231 compared to standard chemotherapeutic drug Cisplatin in soft Agar Assay.

TABLE 55

3D sphere count of MDAMB231 in Mammosphere media at plating efficiency of 2000 cells/well (n = 6 ± S.D)

| | Drug Conc in uM | | | | | GC (Growth Control) | GCD(Growth Control With DMSO) |
|---|---|---|---|---|---|---|---|
| | 250 | 25 | 2.5 | 0.25 | 0.025 | | |
| Cisplatin | 26(±3) | 35(±2) | 46(±3) | 58(±3) | 67(±2) | 72(±3) | 64(±2) |
| Formula XIV | 0(±0) | 22(±3) | 28(±3) | 35(±2) | 38(±5) | 72(±3) | 64(±2) |

Table 55. indicates that Formula XIV is more effective on spheres of MDAMB231 compared to standard chemotherapeutic drug Cisplatin.

TABLE 56

3D sphere count of PC3 in Prostosphere media at plating efficiency of 2000 cells/well (n = 6 ± S.D)

| | Drug Conc in uM | | | | | GC(Growth Control) | GCD(Growth Control With DMSO) |
|---|---|---|---|---|---|---|---|
| | 250 | 25 | 2.5 | 0.25 | 0.025 | | |
| Cisplatin | 21(±2) | 32(±3) | 39(±2) | 42(±3) | 45(±2) | 80(±5) | 76(±4) |
| Formula XIV | 0(±0) | 13(±1) | 20(±2) | 29(±5) | 36(±2) | 80(±5) | 76(±4) |

Table 56 indicates that Formula XIV is more effective on spheres of PC3 compared to standard chemotherapeutic drug Cisplatin.

What is claimed is:

1. A compound of Formula IV:

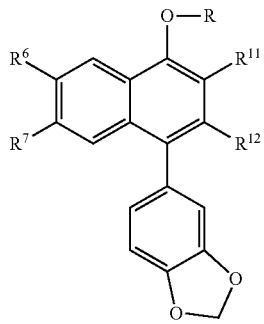

$R^6$ and $R^7$ each independently is selected from —H, or alkoxy;

R is selected from:

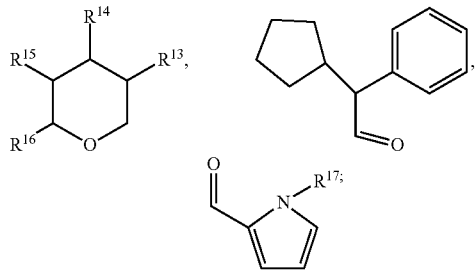

$R^{13}$ is —OH;
$R^{14}$ is selected from alkoxy, or —OH;
$R^{15}$ is selected from alkoxy, or —OH;
$R^{16}$ is —H;
$R^{17}$ is alkyl;

$R^{11}$ and $R^{12}$ each independently is selected from —H, substituted or unsubstituted 5-membered lactone ring, —C(O)O-alkyl;

when R is

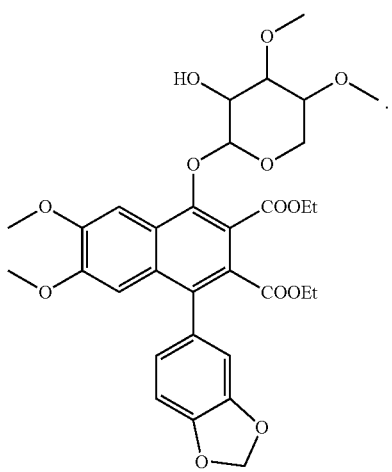

$R^{11}$ and $R^{12}$ are not together as lactone; and
when $R^{13}$ is —OH and, $R^{14}$ and $R^{15}$ are -alkoxy; then $R^{16}$ is —H; $R^6$, $R^7$, $R^{11}$ and $R^{12}$ are not —H.

2. The compound as claimed in claim 1, wherein the compound is compound of Formula VI:

3. The compound as claimed in claim 1, wherein the compound is compound of Formula VII:

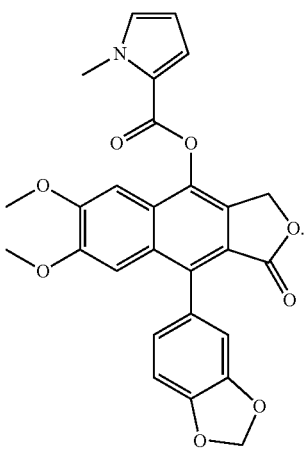 [SMILES: COc1cc2c(OC(=O)c3cccn3C)c3c(c(-c4ccc5c(c4)OCO5)c2cc1OC)C(=O)OC3]

4. The compound as claimed in claim 1, wherein the compound is compound of Formula VIII:

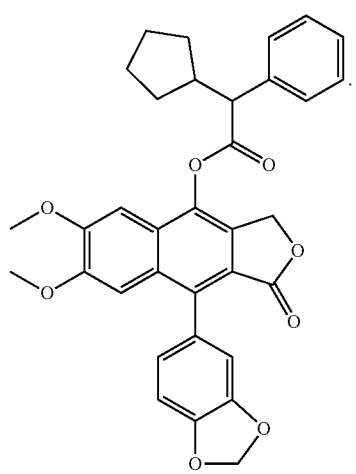 [SMILES: COc1cc2c(OC(=O)C(c3ccccc3)C3CCCC3)c3c(c(-c4ccc5c(c4)OCO5)c2cc1OC)C(=O)OC3]

5. The compound as claimed in claim 1, wherein the compound is compound of Formula IX:

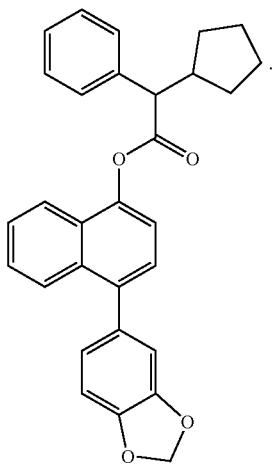 [SMILES: O=C(Oc1ccc(-c2ccc3c(c2)OCO3)c2ccccc12)C(c1ccccc1)C1CCCC1]

6. The compound as claimed in claim 1, wherein the compound is compound of Formula X:

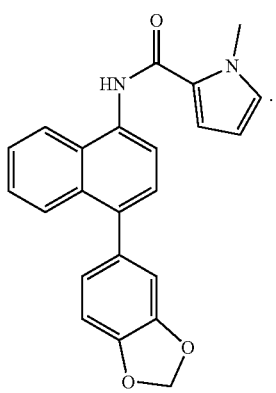 [SMILES: Cn1cccc1C(=O)Nc1ccc(-c2ccc3c(c2)OCO3)c2ccccc12]

7. The compound as claimed in claim 1, wherein the compound is compound of Formula XI:

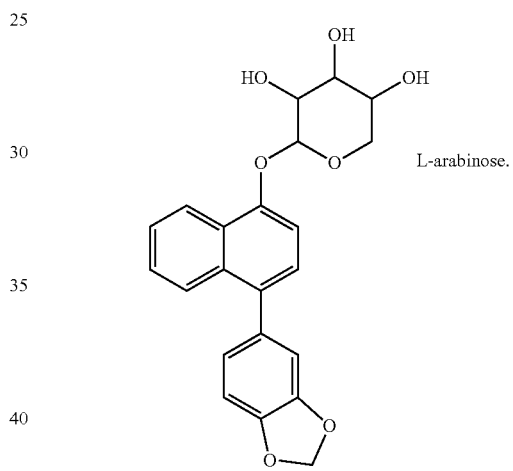

8. The compound as claimed in claim 1 for use in the treatment of cancer.

9. The compound as claimed in claim 8, wherein the cancer is breast, oral, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach cancer.

10. The compound as claimed in claim 8, wherein the cancer is breast or prostate.

11. A pharmaceutical composition comprising the compound as claimed in claim 1 and a pharmaceutically acceptable excipient including carrier, adjuvant, vehicle or mixtures thereof.

* * * * *